(12) United States Patent
Zhang et al.

(10) Patent No.: US 8,993,804 B2
(45) Date of Patent: Mar. 31, 2015

(54) HIGHLY ACTIVE MULTIDENTATE CATALYSTS FOR EFFICIENT ALKYNE METATHESIS

(71) Applicant: The Regents of the University of Colorado, a body corporate, Denver, CO (US)

(72) Inventors: Wei Zhang, Superior, CO (US); Jyothish Kuthanapillil, Boulder, CO (US); Qi Wang, Qingdao (CN)

(73) Assignee: The Regents of the University of Colorado, a body corporate, Denver, CO (US)

( * ) Notice: Subject to any disclaimer, the term of this patent is extended or adjusted under 35 U.S.C. 154(b) by 43 days.

(21) Appl. No.: 13/791,410

(22) Filed: Mar. 8, 2013

(65) Prior Publication Data

US 2013/0261295 A1    Oct. 3, 2013

Related U.S. Application Data

(60) Provisional application No. 61/608,939, filed on Mar. 9, 2012, provisional application No. 61/640,059, filed on Apr. 30, 2012.

(51) Int. Cl.

| | | |
|---|---|---|
| C07C 211/00 | (2006.01) |
| C07C 215/50 | (2006.01) |
| B01J 31/22 | (2006.01) |
| C07C 41/30 | (2006.01) |
| C07C 45/72 | (2006.01) |
| C07D 333/08 | (2006.01) |
| C07D 213/127 | (2006.01) |
| C07D 487/22 | (2006.01) |
| C07C 37/48 | (2006.01) |
| C07B 37/00 | (2006.01) |
| C07C 6/02 | (2006.01) |
| C07F 7/00 | (2006.01) |
| C07C 17/269 | (2006.01) |
| C07F 11/00 | (2006.01) |
| C07C 215/76 | (2006.01) |
| C07C 215/90 | (2006.01) |
| C07D 333/18 | (2006.01) |

(52) U.S. Cl.
CPC ............ *C07C 215/50* (2013.01); *B01J 31/2295* (2013.01); *C07C 41/30* (2013.01); *C07C 45/72* (2013.01); *C07D 333/08* (2013.01); *C07D 213/127* (2013.01); *C07D 487/22* (2013.01); *C07C 37/48* (2013.01); *C07B 37/00* (2013.01); *C07C 6/02* (2013.01); *C07F 7/00* (2013.01); *C07C 17/269* (2013.01); *C07F 11/00* (2013.01); *C07C 215/76* (2013.01); *C07C 215/90* (2013.01); *C07D 333/18* (2013.01)
USPC ........................................................ 564/282

(58) Field of Classification Search
None
See application file for complete search history.

(56) References Cited

PUBLICATIONS

Giannini et al. (J. Am. Chem. Soc., 1999, 121(12), 2784).*

*Primary Examiner* — Rosalynd Keys
*Assistant Examiner* — Jenifer C Sawyer
(74) *Attorney, Agent, or Firm* — Saul Ewing, LLP; Kathryn Doyle; Domingos Silva

(57) ABSTRACT

The invention relates to highly active and selective catalysts for alkyne metathesis. In one aspect, the invention includes a multidentate organic ligand wherein one substrate-binding site of the metal center is blocked. In another aspect, the invention includes N-quaternized or silane-based multidentate organic ligands, capable of binding to metals. In yet another aspect, the invention includes N-quaternized or silane-based multidentate catalysts. The catalysts of the invention show high robustness, strong resistance to small alkyne polymerization and significantly enhanced catalytic activity compared to their corresponding non-quaternized or non-silane-based multidentate catalyst analogs.

10 Claims, 53 Drawing Sheets

Figure 1
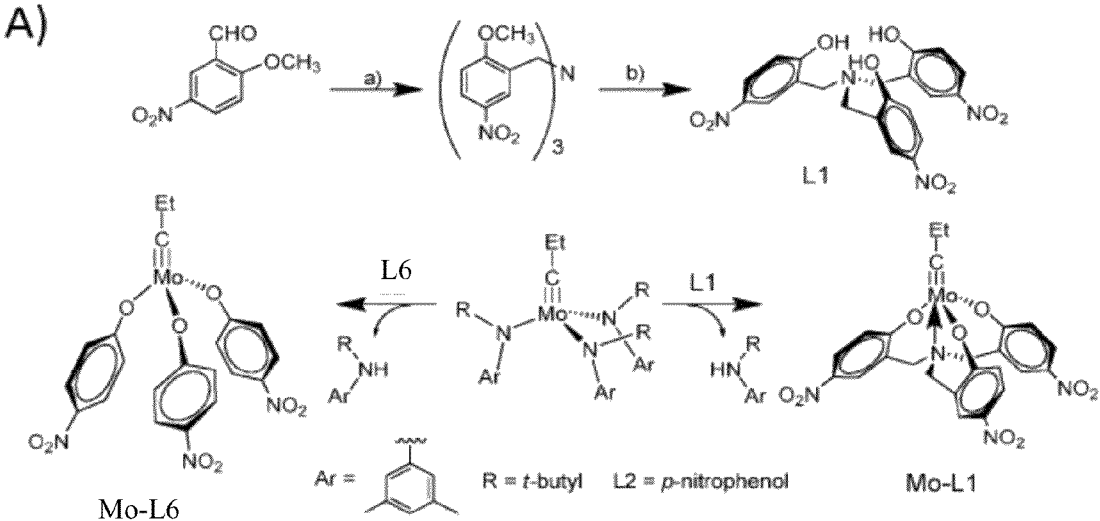
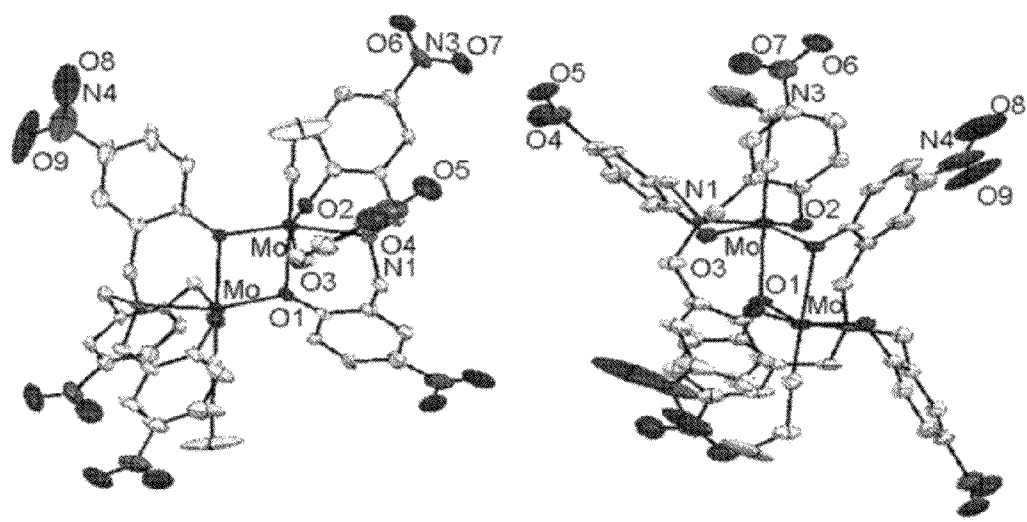

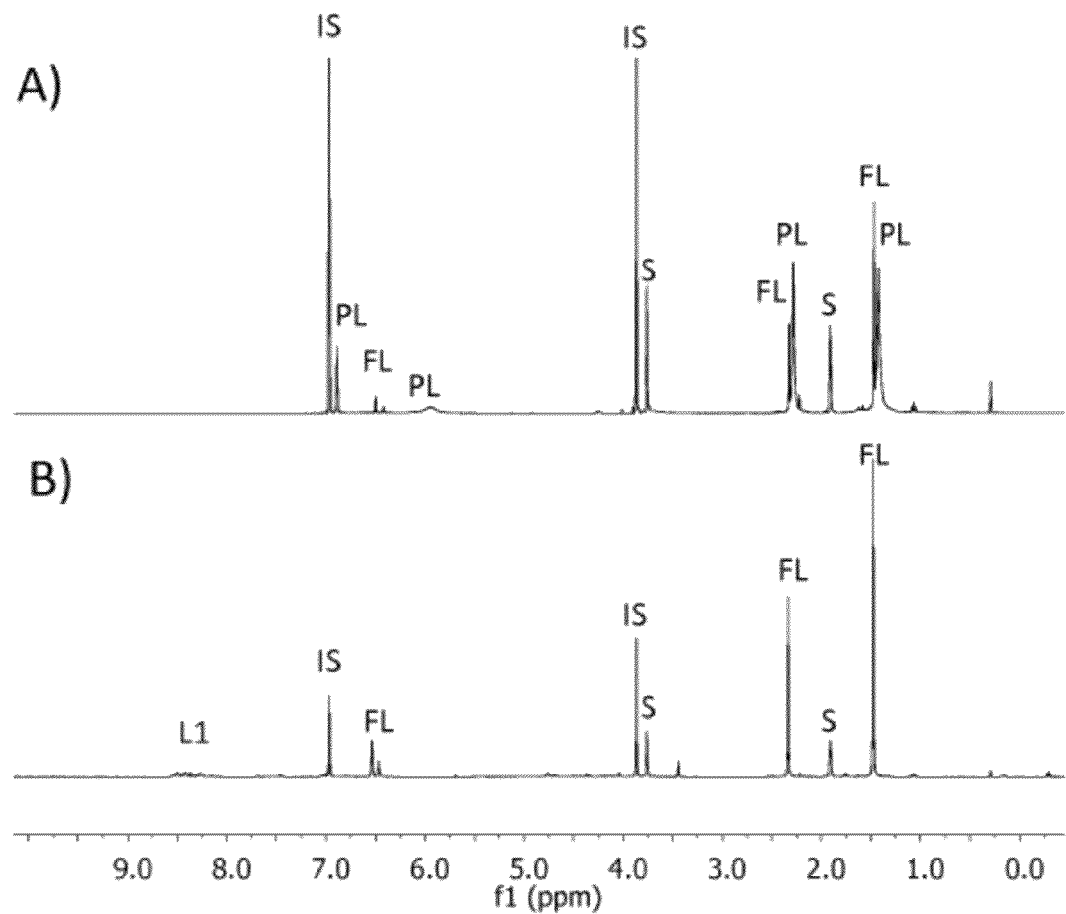

Figure 7
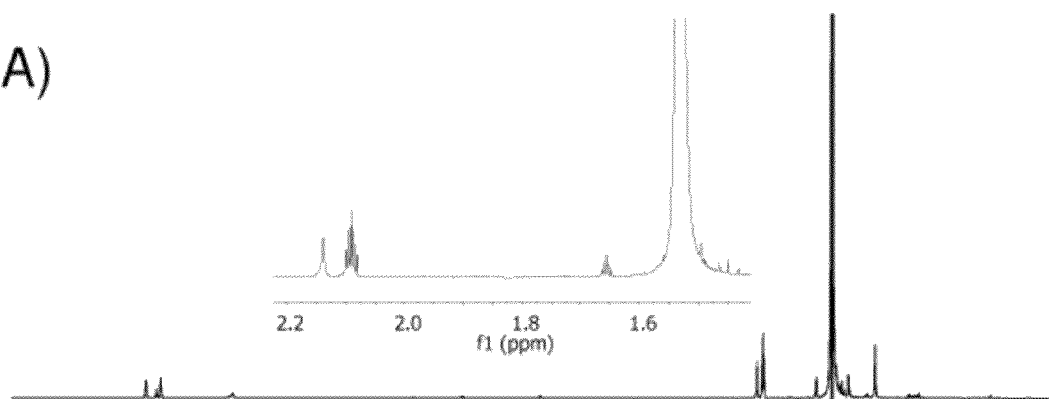
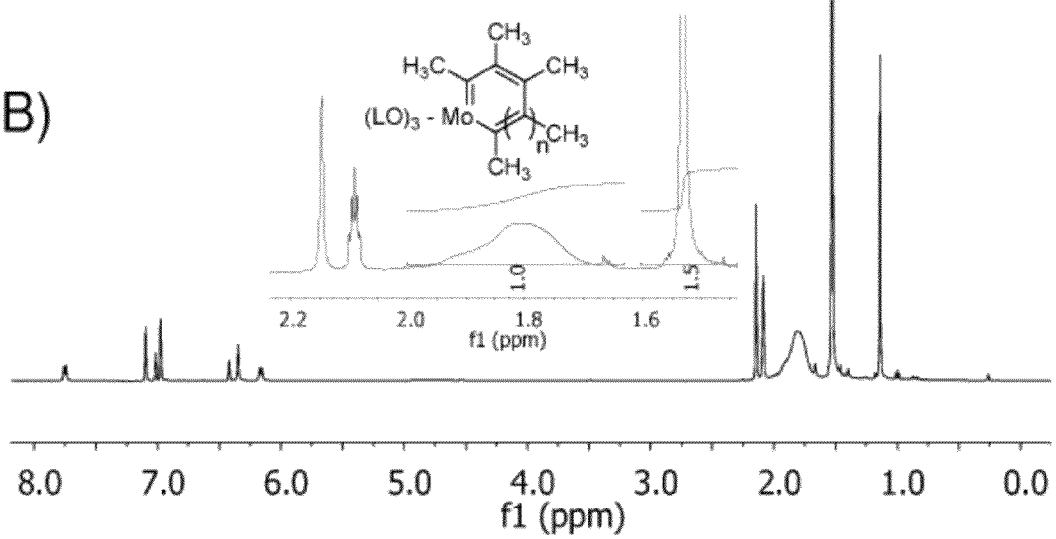

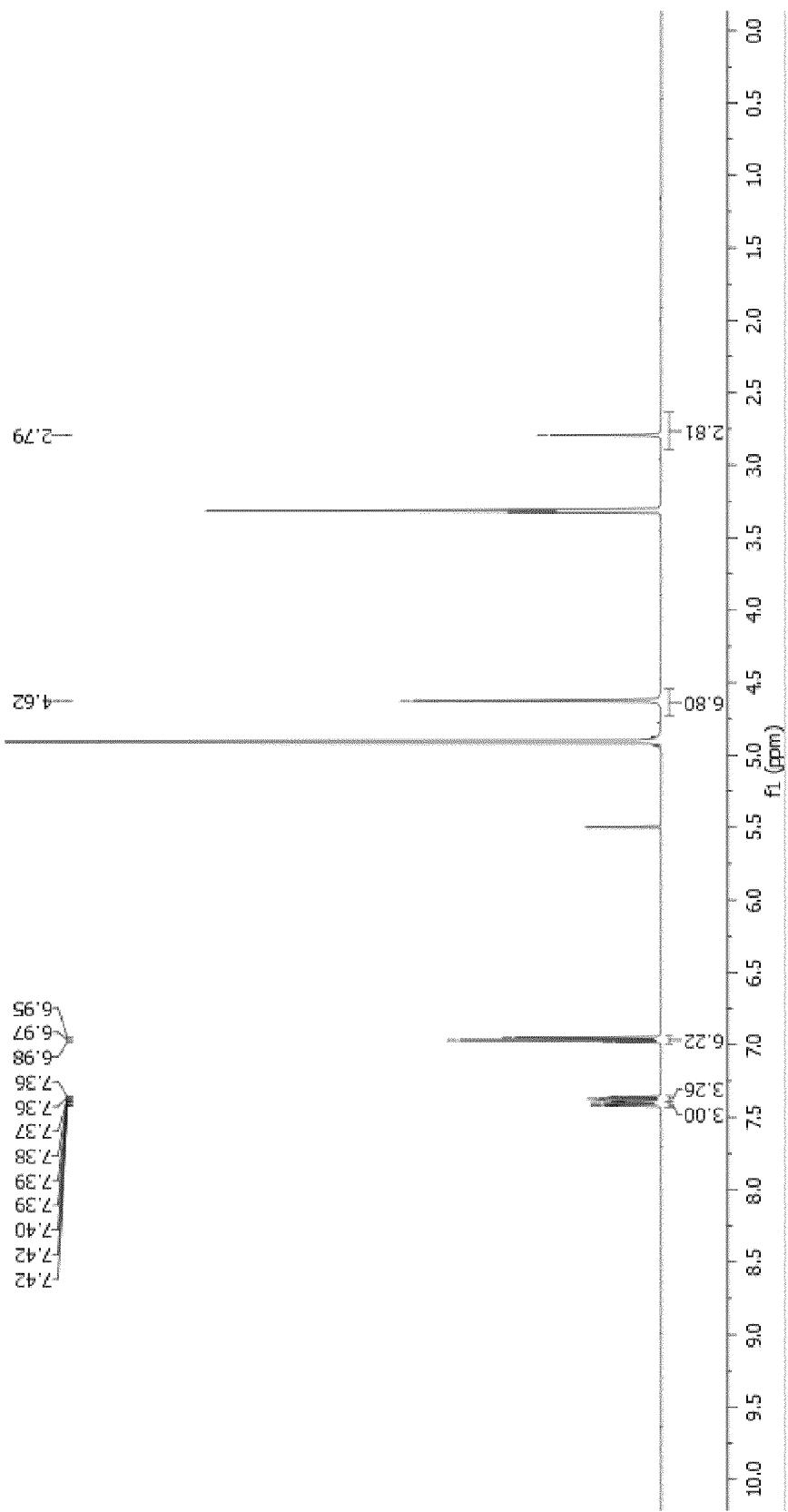

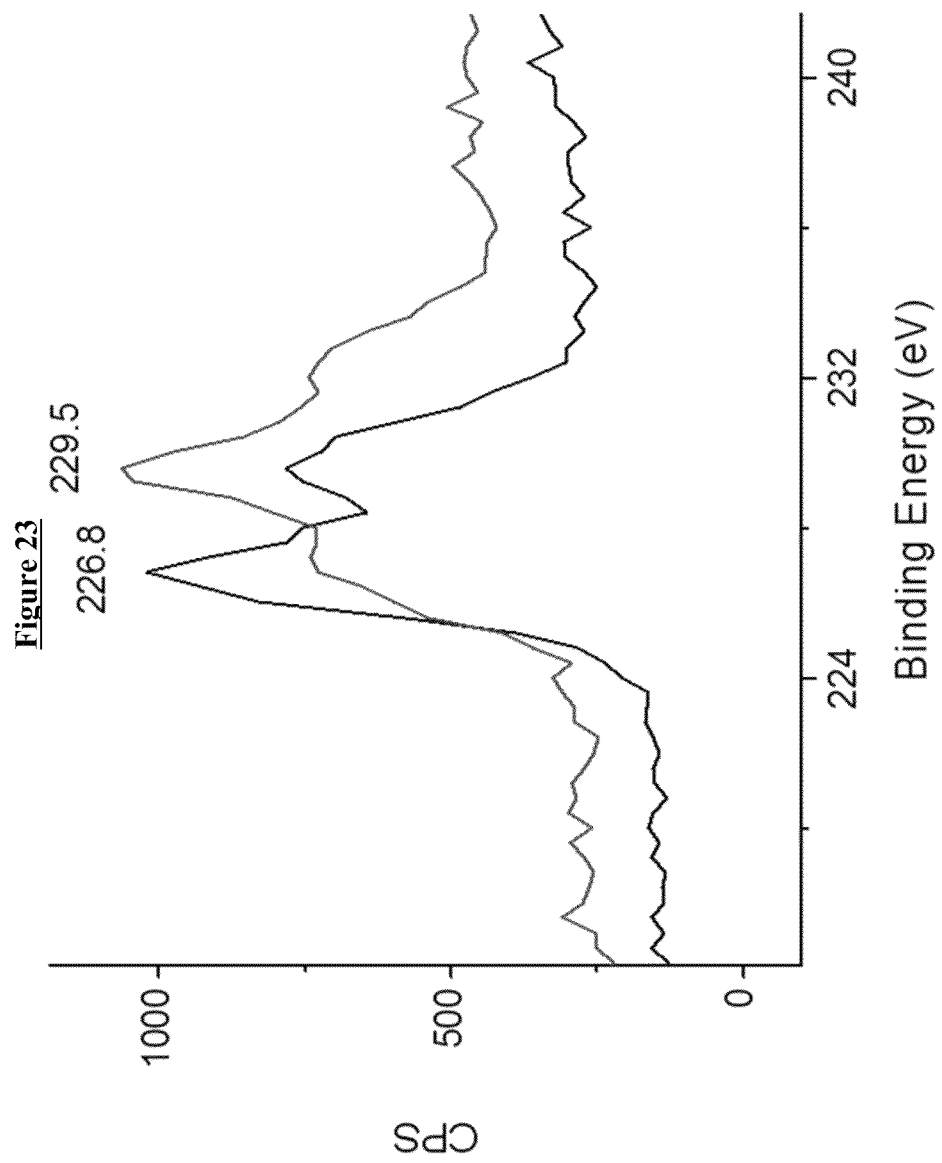

HIGHLY ACTIVE MULTIDENTATE CATALYSTS FOR EFFICIENT ALKYNE METATHESIS

CROSS-REFERENCE TO RELATED APPLICATIONS

The present application claims priority under 35 U.S.C. §119(e) to U.S. Provisional Applications No. 61/608,939, filed Mar. 9, 2012, and No. 61/640,059, filed Apr. 30, 2012, all of which applications are hereby incorporated by reference in their entireties herein.

STATEMENT REGARDING FEDERALLY SPONSORED RESEARCH OR DEVELOPMENT

This invention was made with government support under grant number DMR1055705 awarded by the National Science Foundation. The government has certain rights in the invention.

BACKGROUND OF THE INVENTION

There has been significantly growing interest in recent years in the transition metal-catalyzed metathesis of alkenes and alkynes (Trnka & Grubbs, 2001, Acc. Chem. Res. 34:18; Schrock & Czekelius, 2007, Adv. Synth. Catal. 349:55; Fürstner & Davies, 2005, Chem. Commun. 2307; Zhang & Moore, 2007, Adv. Synth. Catal. 349:93; Mori, 2007, Adv. Synth. Catal. 349:121; Astruc, 2005, New J. Chem. 29:42.). The synthetic potential of the latter, however, is much less explored even after it was used to prepare arylene ethynylene polymers (Bunz, 2001, Acc. Chem. Res. 34:998; Mang & Moore, 2004, Macromolecules 37:3973; Fischer & Nuckolls, 2010, Angew. Chem. 122: 7415; 2010, Angew. Chem. Int. Ed. 49:7257) and macrocycles (Zhang & Moore, 2006, Angew. Chem. 118:4524; 2006, Angew. Chem. Int. Ed. 45:4416; Zhang & Moore, 2005, J. Am. Chem. Soc. 127:11863; Zhang & Moore, 2004, J. Am. Chem. Soc. 126:12796; Ge et al., 2000, Angew. Chem. 112:3753; 2000, Angew. Chem. Int. Ed. 39:3607; Johnson II et al., 2007, Org. Lett. 9:3725; Jiang & Tew, 2008, Org. Lett. 10:4393), and in natural product synthesis (Fürstner & Davies, 2005, Chem. Commun. 2307; Micoine & Fürstner, 2010, J. Am. Chem. Soc. 132:14064).

Typically, the metal-alkylidyne catalysts for alkyne metathesis contain a metal-carbon triple bond and alkoxide/phenoxide/siloxide/amide ligands (Schrock, 2002, Chem. Rev. 102:145), and their catalytic activity can be tuned through judicious ligand design. Coordination of small molecules, in particular 2-butyne (a common metathesis byproduct), to the hexavalent Mo-alkylidyne complex, is an interfering reaction that leads to undesired alkyne polymerization (through the ring expansion mechanism, requiring two open substrate-binding sites) as well as nonproductive reaction pathways.

Polyhedral oligomeric silsesquioxane (POSS) and silica are the only reported ligands so far that can overcome this long-standing problem (Weissman et al., 2006, Angew. Chem. 118:599; 2006, Angew. Chem. Int. Ed. 45:585, Cho et al., 2006, J. Am. Chem. Soc. 128:14742; Gauvin et al., 2007, Dalton Trans. 3127). However, the siloxane-based approach lacks tunability in the catalyst structure, thus making it difficult to study the structure-activity relationship of the catalyst and tune its activity.

There is a need in the art for the identification of a novel ligand that can be used to generate highly active and selective catalysts for alkyne metathesis. The activity of these ligands should be tunable as to afford good metathesis activity and functional group tolerance. The present invention fulfills these needs.

BRIEF DESCRIPTION OF THE INVENTION

The invention includes a compound of formula (I), or a salt thereof:

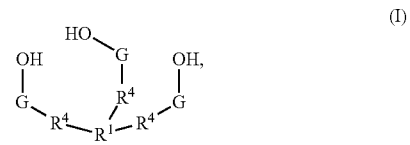

wherein
each G is independently alkyl, aryl or heteroaryl, wherein the alkyl, aryl or heteroaryl is optionally and independently substituted with at least one alkyl, halogen or electron-withdrawing substituent; $R^4$ is a single bond, heteroatom, or an optionally substituted $C_1$-$C_3$ alkyl; and, $R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and $A^-$ is an anion.

In one embodiment, $R^1$ is N and each G is independently substituted with at least one electron-withdrawing substituent. In another embodiment, $R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and $A^-$ is an anion.

In one embodiment, the compound of formula (I) is the compound of formula (II) or a salt thereof:

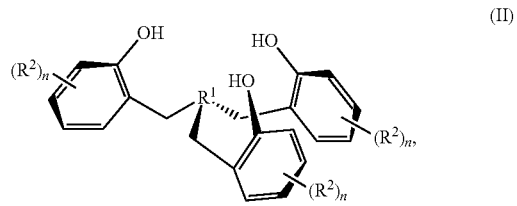

wherein:
$R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and $A^-$ is an anion; each occurrence of n is independently 0, 1, 2, 3 or 4; each occurrence of $R^2$ is independently alkyl, halogen or an electron-withdrawing group; with the proviso that, if $R^1$ is selected from the group consisting of N and P, at least one occurrence of n is not zero, and at least one occurrence of $R^2$ is an electron-withdrawing group.

In one embodiment, the compound of formula (II) is the compound of formula (IIa) or a salt thereof:

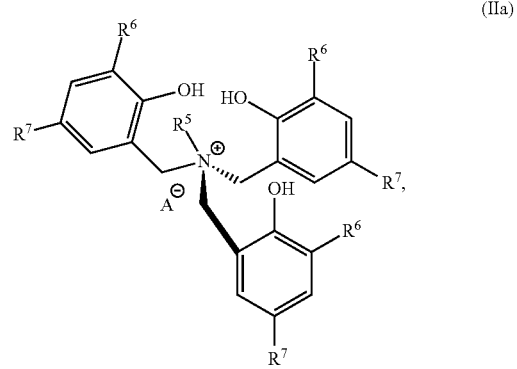

wherein
$R^5$ is alkyl, $R^6$ is hydrogen or alkyl, $R^7$ is hydrogen, halogen or $NO_2$, and $A^-$ is an anion.

In one embodiment, the compound of formula (II) is selected from the group consisting of:

ligand L1
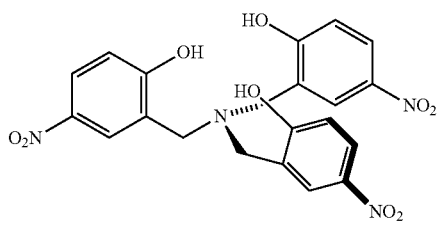

ligand L2
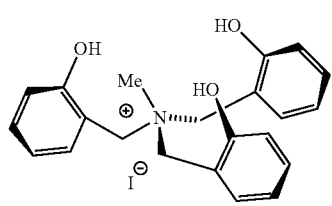

ligand L3
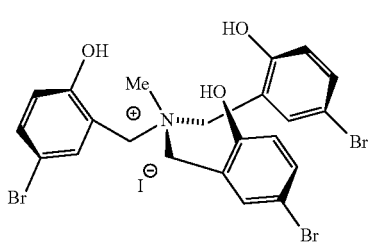

ligand L4
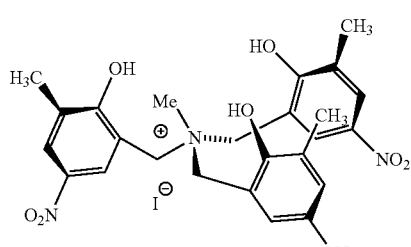

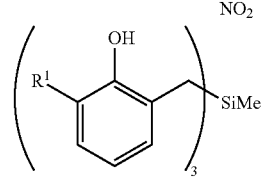

L7a: $R^1$ = H
L7b: $R^1$ = Me
L7c: $R^1$ = i-Pr

The invention also includes a compound of formula (III) or a salt thereof:

(III)
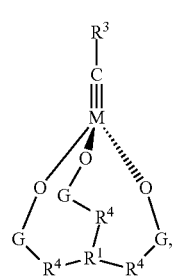

wherein:
each G is independently alkyl, aryl or heteroaryl, wherein the alkyl, aryl or heteroaryl is optionally and independently substituted with alkyl, halogen or electron-withdrawing substituents; $R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and $A^-$ is an anion; $R^3$ is selected from the group consisting of alkyl, alkyl(aryl) and aryl, all of which are optionally substituted; $R^4$ is a single bond, heteroatom, or an optionally substituted $C_1$-$C_3$ alkyl chain; and, M is a metal.

In one embodiment, M is a transition metal. In another embodiment, M is selected from the group consisting of Mo, W, Re and Ta. In yet another embodiment, $R^1$ is N and each G is independently substituted with at least one electron-withdrawing substituent. In yet another embodiment, $R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and $A^-$ is an anion. In yet another embodiment, G is phenyl, naphthyl or anthracenyl.

In one embodiment, the compound of formula (III) is the compound of formula (IV) or a salt thereof:

(IV)
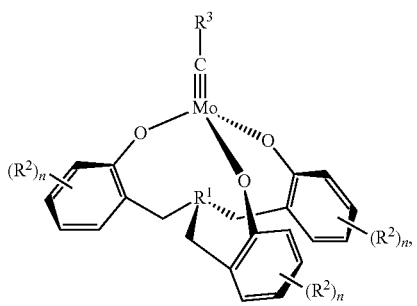

wherein:
each occurrence of n is independently 0, 1, 2, 3, or 4; $R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and K is an anion; each occurrence of $R^2$ is independently selected from the group consisting of alkyl, alkoxy, halogen, nitro, cyano, trifluoromethyl, trichloromethyl, carboxy, formyl, lower alkanoyl, carboxyamido and aryl lower alkanoyl; $R^3$ is alkyl, alkyl(aryl) or aryl, all of which are optionally substituted; and M is selected from the group consisting of Mo, W, Re and Ta, with the proviso that, if $R^1$ is selected from the group consisting of N and P, at least one occurrence of n is not zero.

In one embodiment, $R^1$ is $N^+H(A^-)$ or $N^+(R)(A^-)$, R is optionally substituted alkyl or aryl, and $A^-$ is an anion.

In one embodiment, the compound of formula (III) is selected from the group consisting of:

1
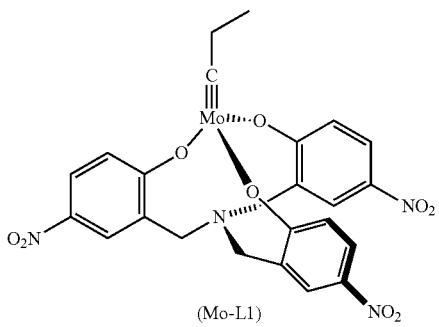

(Mo-L1)

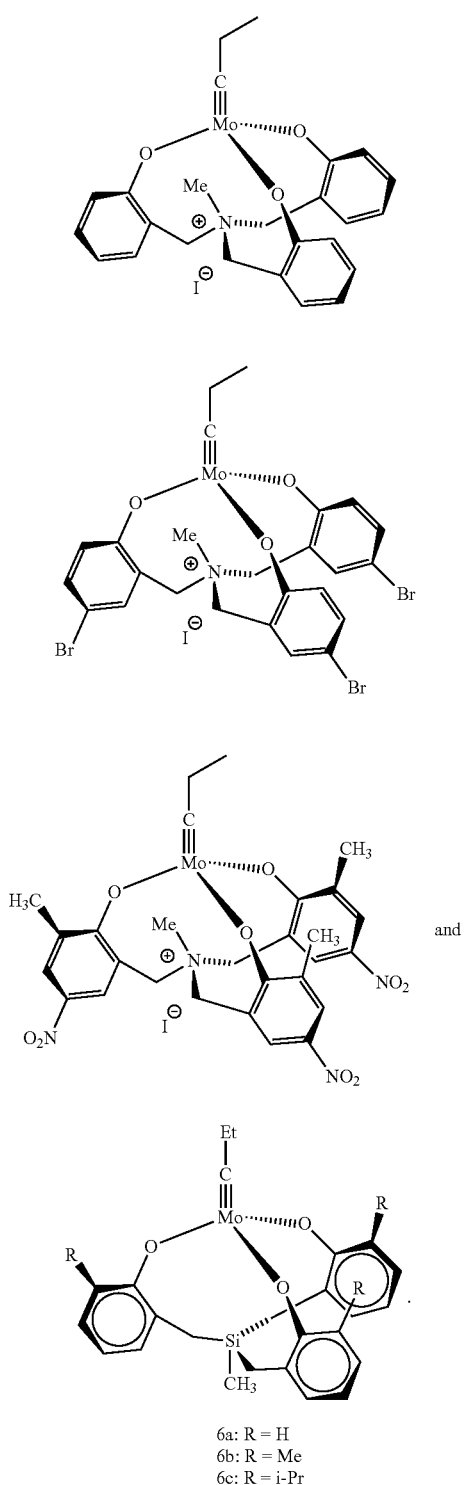

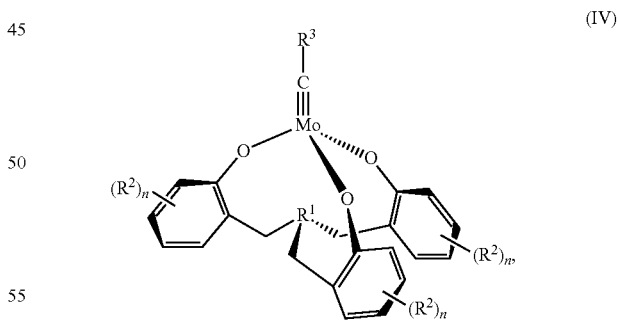

wherein: $R^1$ is selected from the group consisting of N, $N^+H$ ($A^-$), $N^+R(A^-)$, B, P, CH, CR, SiR and a 1,3,5-trivalent phenyl moiety, wherein R is optionally substituted alkyl or aryl, and K is an anion; each occurrence of n is independently 0, 1, 2, 3 or 4; each occurrence of $R^2$ is independently alkyl, halogen or an electron-withdrawing group; $R^3$ is alkyl, alkyl(aryl) or aryl, all of which are optionally substituted; M is selected from the group consisting of Mo, W. Re and Ta, with the proviso that, if $R^1$ is selected from the group consisting of N and P, at least one occurrence of n is not zero, and at least one occurrence of $R^2$ is an electron-withdrawing group.

The invention also includes a method of preparing an alkyne-containing metathesis product. The method comprises contacting a first alkyne-containing substrate with a second alkyne-containing substrate in the presence of a compound of formula (IV) or a salt thereof, whereby the metathesis product of the first and second alkyne-containing substrates is formed:

(IV)

wherein:
each occurrence of n is independently 0, 1, 2, 3, or 4; $R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and $A^-$ is an anion; each occurrence of $R^2$ is independently selected from the group consisting of alkyl, halogen, nitro, cyano, trifluoromethyl, trichloromethyl, carboxy, formyl, lower alkanoyl, carboxyamido and aryl lower alkanoyl; $R^3$ is alkyl, alkyl (aryl) or aryl, all of which are optionally substituted; and M is The invention also includes a method of preparing a compound of formula (IV). The method comprises reacting a compound of formula (II) with a metal alkylidyne compound with exchangeable ligands:

selected from the group consisting of Mo, W. Re and Ta, with the proviso that, if $R^1$ is selected from the group consisting of N and P, at least one occurrence of n is not zero.

In one embodiment, the compound of formula (IV) is selected from the group consisting of:

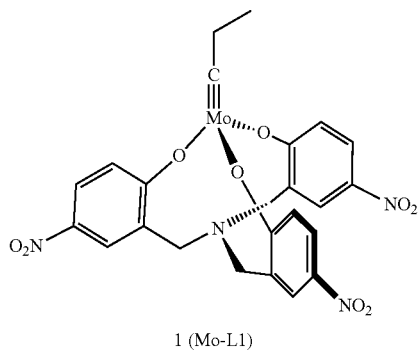

1 (Mo-L1)

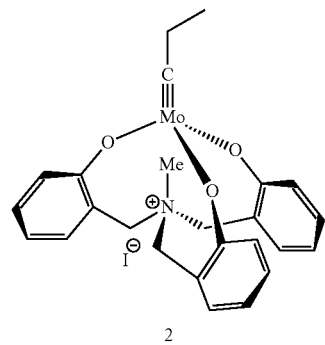

2

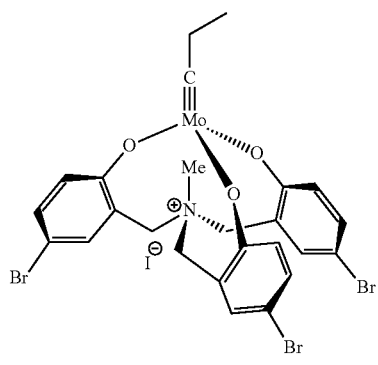

3

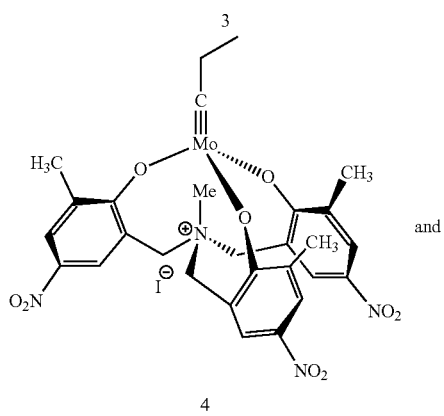

and

4

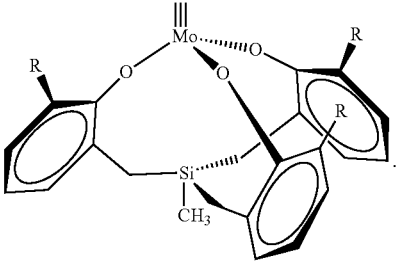

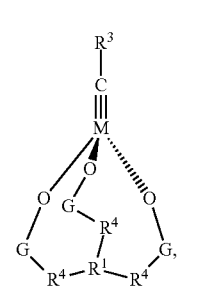

6a: R = H
6b: R = Me
6c: R = i-Pr

The invention also includes a kit for preparing a compound of formula (III), comprising a compound of formula (I) and a metal alkylidyne compound with exchangeable ligands,

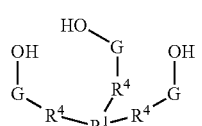

(I)

(III)

wherein: each G is independently alkyl, aryl or heteroaryl, wherein the alkyl, aryl or heteroaryl is optionally and independently substituted with alkyl, halogen or electron-withdrawing substituents; $R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and K is an anion; $R^3$ is selected from the group consisting of alkyl, alkyl(aryl) and aryl, all of which are optionally substituted; $R^4$ is a single bond, heteroatom, or an optionally substituted $C_1$-$C_3$ alkyl chain; and, M is a metal.

In one embodiment, the compound of formula (III) is a compound of formula (IV) or a salt thereof, and the compound of formula (I) is a compound of formula (II) or a salt thereof:

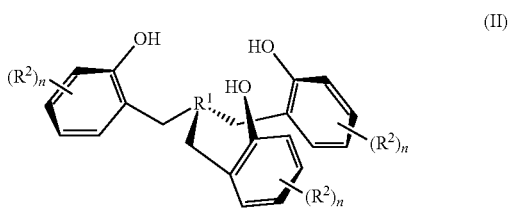

(II)

-continued (IV)

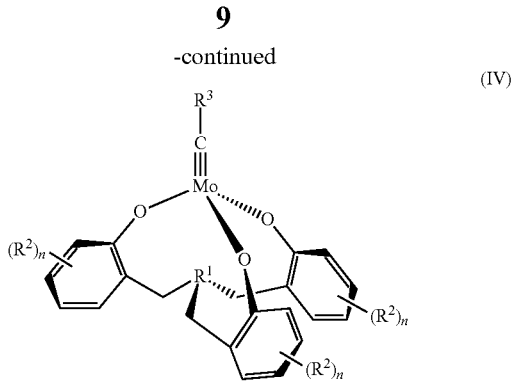

-wherein: $R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and K is an anion; each occurrence of n is independently 0, 1, 2, 3 or 4; each occurrence of $R^2$ is independently alkyl, halogen or an electron-withdrawing group; $R^3$ is alkyl, alkyl (aryl) or aryl, all of which are optionally substituted; and M is selected from the group consisting of Mo, W, Re and Ta, with the proviso that, if $R^1$ is selected from the group consisting of N and P, at least one occurrence of n is not zero, and at least one occurrence of $R^2$ is an electron-withdrawing group.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

FIG. 1, comprising FIGS. 1A-1B, is a scheme illustrating the synthesis and characterization of compounds of the invention. FIG. 1A: Synthesis of the multidentate ligand L1 and the generation of the alkyne metathesis catalyst from the trisamido Mo(VI) propylidyne precursor: (a) $NaBH(OAc)_3$, $NH_4OAc$, THF, RT, 69%; (b) LiI, quinoline, 170° C., 87%. FIG. 1B: Crystal structure of the Mo-L1 dimer complex from two different view angles.

FIGS. 3A-3B, illustrates the $^1H$ NMR spectra ($CD_3OD$, 500 MHz, FIG. 3A) and $^{13}C$ NMR spectra (DMSO-$d_6$, 100 MHz, FIG. 3B) of the ligand L1.

FIG. 4, comprising FIGS. 4A-4B, illustrates a $^1H$ NMR experiment in THF-$d_4$ showing the displacement of the ligands on the Mo-precursor complex with L1 before (FIG. 4A) and after (FIG. 4B) mixing with L1. IS=internal standard (1,4-dimethoxybenzene), PL=precursor ligand coordinated to Mo, FL=free precursor ligand, L1=multidentate ligand coordinated to Mo, S=solvent.

FIG. 5, comprising

FIG. 6, comprising

FIG. 7, comprising FIGS. 7A-7B, illustrates 2-butyne polymerization experiments in $d_8$-toluene using the catalyst, (FIG. 7A) Mo-L1; (FIG. 7B) Mo-L6. $^1H$ NMR was acquired after 24 h and 1 h respectively, for Mo-L1 and Mo-L6.

FIGS. 10A-10B, illustrates a metathesis reaction of entry 10 in Table 2 in $CCl_4$ at 70° C. using 3 mol % loading of Mo-L1. Reaction was monitored after 3 h (FIG. 10A) and 7 h (FIG. 10B) by $^1H$ NMR spectroscopy; P=Product, SM=Starting material.

FIGS. 11A-11B, illustrates a precipitation-driven cyclooligomerization of diyne monomer 12 in Table 2 in $CCl_4$ at 30° C. using 3 mol % loading of Mo-L1 catalyst. Reaction was monitored after 1 h (FIG. 11A) and 2 h (FIG. 11B) by $^1H$ NMR spectroscopy; P=Product, SM=Starting material.

FIG. 17, comprising

FIG. 18, comprising FIGS. 18A-18B, illustrates the $^1H$ NMR spectra ($CD_3OD$, 500 MHz, FIG. 18A) and $^{13}C$ NMR spectra ($CD_3OD$, 100 MHz, FIG. 18B) of the ligand L2.

FIG. 19, comprising

FIG. 20, comprising

FIG. 21, comprising FIG. 21A: catalyst precursor before mixing with L5. FIG. 21B: after mixing precursor with L5. FIG. 21C: catalyst precursor before mixing with L3. FIG. 21D: after mixing precursor with L3. IS=internal standard (1,4-dimethoxybenzene), PL=precursor amide ligand coordinated to Mo, FL=free aniline ligand, L5=multidentate ligand coordinated to Mo, S=solvent. L3 (multidentate ligand coordinated to Mo) could not be observed in the NMR.

FIG. 23 illustrates X-ray photoelectron spectroscopy data for the peak that corresponds to the binding energy of Mo 3d electrons in catalyst 5 (peak at 226.8 ev) and 2 (peak at 229.5 ev).

FIG. 24, comprising FIG. 24A: Kinetic study of catalysts 2-4 by alkyne metathesis of 1-nitro-4-propynylbenzene (2.5 mol % catalyst, 40° C., CCl$_4$). Square: catalyst 2; Circle: catalyst 3; Triangle: catalyst 4. FIG. 24B: Kinetic study of catalysts 2-4 by alkyne metathesis of 1-formyl-4-propynylbenzene (2.5 mol % catalyst, 40° C., CCl$_4$). Square: catalyst 2; circle: catalyst 3; triangle: catalyst 4. FIG. 24C: Kinetic study of catalysts 2-4 by alkyne metathesis of 3-propynylpyridine (2.5 mol % catalyst, 40° C., CCl$_4$). Square: catalyst 2; circle: catalyst 3; triangle: catalyst 4.

FIG. 27, comprising

FIG. 28, comprising

FIG. 29, comprising

FIG. 31, comprising

FIG. 32, comprising

FIGS. 33A-33C, is a series of graphs illustrating the conversion of 4-formylpropynylbenzene in the catalytic runs (3 mol % loading, 40° C.) at different time intervals after the generation of the catalysts. FIG. 33A: catalyst Mo-L6, stored at room temperature after its generation. FIG. 33B: catalyst 6b, stored at room temperature after its generation. FIG. 33C: catalyst 6b, stored at −30° C. after its generation.

FIG. 34, comprising FIG. 34A: L7b before mixing with catalyst precursor. FIG. 34B: Precursor before mixing with L7b. FIG. 34C: Precursor after mixing with L7b. IS=internal standard (1,4-dimethoxybenzene), PL=precursor ligand coordinated to Mo, FL=free precursor ligand, L7b=multidentate ligand coordinated to Mo.

DETAILED DESCRIPTION OF THE INVENTION

Figure 2:
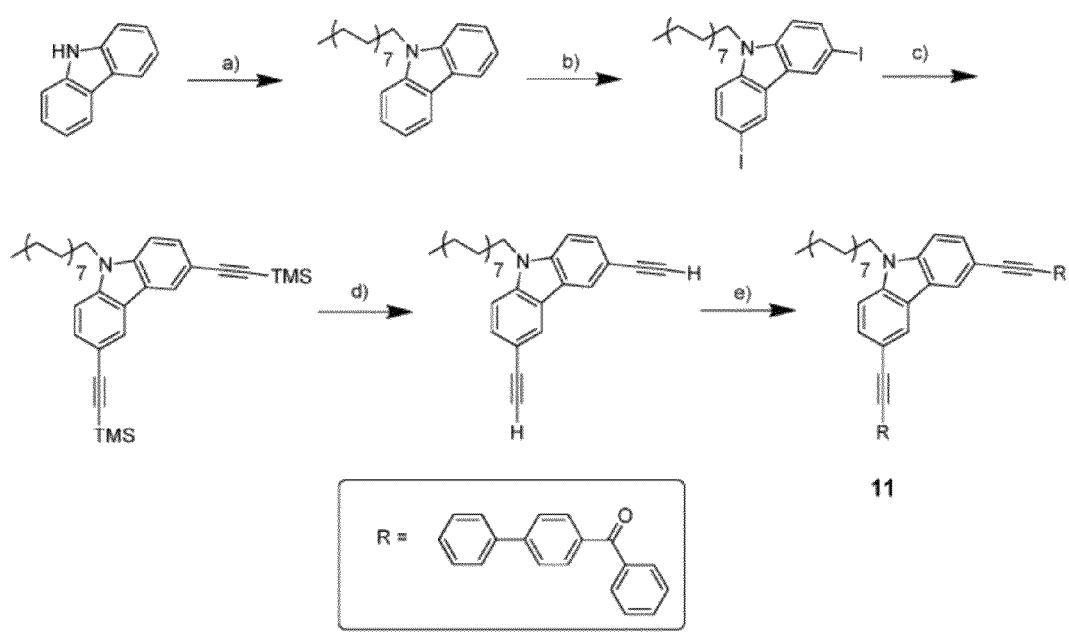
FIG. 2 is a scheme illustrating the synthesis of a diarylethynyl carbazole monomer. Conditions: (a) $CH_3(CH_2)_{15}Br$, NaH, THF-OMF, RT, 96%. (b) NIS, $CHCl_3$-AcOH, 93%. (c) (trimethylsilyl)acetylene, $Pd(PPh_3)_2Cl_2$, CuI, THF, piperidine, RT, 92%. (d) NaOH, $H_2O$-EtOH, RT, 96%. (e) RBr, $Pd(PPh_3)_2Cl_2$, CuI, THF, piperidine, 70° C., 57%.

The invention relates to highly active and selective catalysts for alkyne metathesis.

In one aspect, the invention includes a multidentate organic ligand wherein one substrate-binding site of the metal center is blocked, thus inhibiting undesired alkyne polymerization. Further, the metathesis activity and functional group tolerance of the catalysts may be structurally fine tuned by the introduction of customizable electron-withdrawing substituents.

In another aspect, the invention includes N-quaternized multidentate organic ligands, capable of binding to metals.

In yet another aspect, the invention includes N-quaternized multidentate catalysts, such as tris(arylmethyl)ammonium-coordinated Mo(VI) propylidyne catalysts. These catalysts show high robustness, strong resistance to small alkyne polymerization and significantly enhanced catalytic activity compared to their corresponding tris(arylmethyl)amine-based analogues.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, animal pharmacology, and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "RT" "or "rt" refers to room temperature.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "enantiomeric purity" of a given enantiomer over the opposite enantiomer indicates the excess % of the given enantiomer over the opposite enantiomer, by mole. For example, in a mixture comprising about 80% of a given enantiomer and about 20% of the opposite enantiomer, the enantiomeric purity of the given enantiomer is about 60%.

As used herein, the term "essentially free of" as applied to a given enantiomer in a mixture with the opposite enantiomer indicates that the enantiomeric purity of the given enantiomer is higher than about 80%, more preferably higher than about 90%, even more preferably higher than about 95%, even more preferably higher than about 97%, even more preferably higher than about 99%, even more preferably higher than about 99.5%, even more preferably higher than about 99.9%, even more preferably higher than about 99.95%, even more preferably higher than about 99.99%. Such purity determination may be made by any method known to those skilled in the art, such as chiral HPLC analysis or chiral electrophoresis analysis.

As used herein, the term "anion" refers to a negatively charged counterion such as chloride, bromide, iodide, or trifluoroacetate.

As used herein, the term "electron-withdrawing" as applied to a substituent or group refers to the ability of a substituent or group to draw electrons to itself more so than a hydrogen atom would if it occupied the same position in the molecule. This term is well understood by one skilled in the art and is discussed in Advanced Organic Chemistry, by J. March, 4th Ed. John Wiley and Sons, New York, N.Y. pp. 18-19 (1992), and the discussion therein is incorporated by reference. Non-limiting examples of electron withdrawing substituents include halo, especially fluoro, chloro, bromo, iodo; nitro; cyano; trifluoromethyl; trichloromethyl; carboxy; formyl; lower alkanoyl; carboxyamido; aryl; and aryl lower alkanoyl. In certain embodiments, electron withdrawing substituents are selected from the group consisting of nitro; cyano; trifluoromethyl; trichloromethyl; carboxy; formyl; lower alkanoyl; carboxyamido; and aryl lower alkanoyl. In other embodiments, electron withdrawing substituents are selected from the group consisting of $NO_2$, CN, $CF_3$, F, Cl and Br.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 3 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$—$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term "aryl" includes aromatic monocyclic or multicyclic, e.g., tricyclic, bicyclic, hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthracenyl, naphthyl and phenanthryl. Aryl groups can also be fused or bridged with aliphatic cyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl. pyrrolyl, and tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

Moreover, the alkyl, aryl and heteroaryl, groups described above can be "unsubstituted" or "substituted." The term "substituted" is intended to describe moieties having substituents replacing a hydrogen on at least one non-hydrogen atom, e.g. C, O or N, of a molecule. Such substituents can independently include, for example, at least one of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN). —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}(CR'R'')_{0-3}H$, $(CR'R'')_{0-3}S(O)_{0-3}R'$ (e.g., —$SO_3H$, —$OSO_3H$), $(CR'TR'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$ (substituted or unsubstituted phenyl), $(CR'R'')_{0-3}(C_3$-$C_8$ cycloalkyl), $(CR'R'')_{0-3}CO_2R'$ (e.g., —$CO_2H$), or $(CR'R'')_{0-3}OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group.

DESCRIPTION

The invention includes a multidentate organic ligand of the formula (I) or a salt thereof, wherein one substrate-binding site of the metal center is blocked thus inhibiting the undesired alkyne polymerization. Further, the metathesis activity and functional group tolerance of the ligand may be structurally tuned using customizable electron-withdrawing substituents.

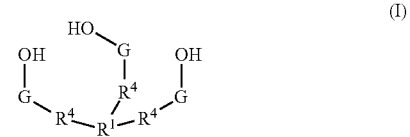

(I)

In one aspect, $R^1$ is a quaternized nitrogen group. As demonstrated herein, quaternization of the nitrogen group prevents the nitrogen atom from coordinating to the metal center, and thus increases the electrophilicity of the metal and the catalytic performance of the complex. The corresponding catalyst (wherein the ligand is bound to a Mo(VI) propylidyne group, in a non-limiting example) shows high robustness, strong resistance to small alkyne polymerization and significantly enhanced catalytic activity compared to their corresponding tris(arylmethyl)amine-based analogues.

In one embodiment, each G moiety of formula (I) is independently alkyl, aryl or heteroaryl, wherein the alkyl, aryl or heteroaryl is optionally and independently substituted with alkyl, halogen or electron-withdrawing substituents. In one embodiment, each G is independently substituted with at least one electron-withdrawing substituent. In another embodiment, each G is optionally substituted 1-4 times with electron withdrawing substituents. In yet another embodiment, the electron-withdrawing substituents are selected from the group consisting of nitro, cyano, trifluoromethyl, trichloromethyl, carboxy, formyl, lower alkanoyl, carboxyamido and aryl lower alkanoyl. In yet another embodiment, each G is independently selected from the group consisting of optionally substituted phenyl, naphthyl and anthracenyl. In yet another embodiment, G is an optionally substituted $C_1$-$C_3$ alkyl moiety. In yet another embodiment, G is optionally substituted phenyl. In yet another embodiment, G is —$C(CF_3)_2$— or —$CF_2$—.

In one embodiment, $R^4$ is a single bond, heteroatom, or an optionally substituted $C_1$-$C_3$ alkyl chain. In another embodiment, $R^4$ is —$CH_2$—.

In one embodiment, $R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl and aryl, and $A^-$ is an anion. In another embodiment, $R^1$ is N and each G is independently substituted with at least one electron-withdrawing substituent In one embodiment, the compound of formula (I) is a compound of formula (II) or a salt thereof:

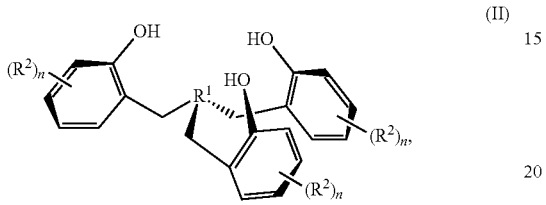

(II)

wherein:
$R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and $A^-$ is an anion;
each occurrence of n is independently 0, 1, 2, 3 or 4;
each occurrence of $R^2$ is independently alkyl, halogen or an electron-withdrawing group; with the proviso that, if $R^1$ is selected from the group consisting of N and P, at least one occurrence of n is not zero, and at least one occurrence of $R^2$ is an electron-withdrawing group.

In one embodiment, each $R^2$ substituent is alkyl or an electron-withdrawing substituent selected from the group consisting of nitro, cyano, trifluoromethyl, trichloromethyl, carboxy, formyl, lower alkanoyl, carboxyamido and aryl lower alkanoyl. In another embodiment, $R^2$ is methyl, isopropyl, or $NO_2$. In yet another embodiment, n=1-2 and each $R^2$ is independently alkyl, halogen or nitro. In yet another embodiment, wherein $R^1$ is $N^+R(A^-)$ or $N^+H(A^-)$, n is 0. In yet another embodiment, wherein $R^1$ is N or P, n is 1, 2, 3 or 4. In yet another embodiment, $R^1$ is N and each $R^2$ is an electron-withdrawing group selected from the group consisting of nitro, cyano, trifluoromethyl, trichloromethyl, carboxy, formyl, lower alkanoyl, carboxyamido and aryl lower alkanoyl.

In one embodiment, the compound of formula (II) is a compound of formula (IIa) or a salt thereof:

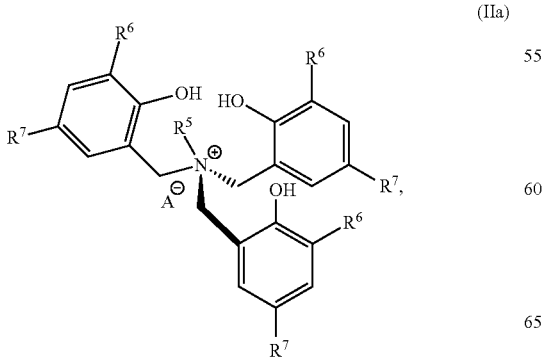

(IIa)

wherein
$R^5$ is alkyl, $R^6$ is hydrogen or alkyl, $R^7$ is hydrogen, halogen or $NO_2$, and $A^-$ is an anion.

In one embodiment, the compound of formula (II) is the ligand L1 or a salt thereof:

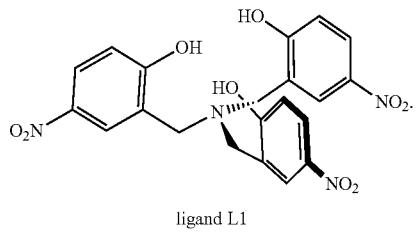

ligand L1

In one embodiment, the compound of formula (II) is selected from the group consisting of ligands L2-L4:

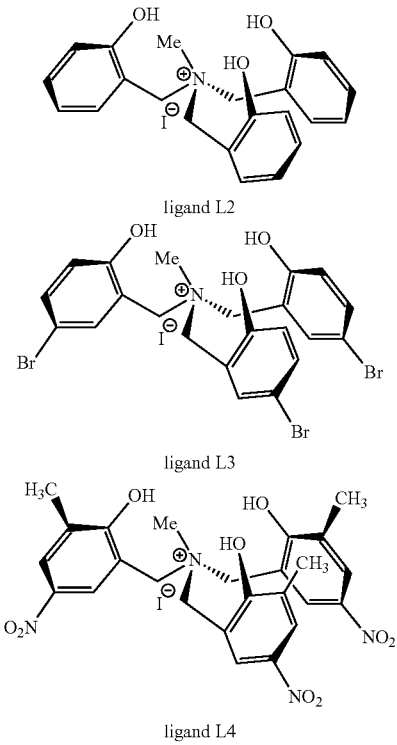

ligand L2 ligand L3 ligand L4

In one embodiment, the compound of formula (II) is selected from the group consisting of ligands L7a-L7c:

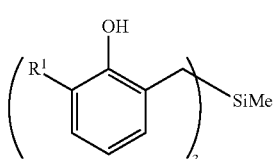

L7a: $R^1$ = H
L7b: $R^1$ = Me
L7c: $R^1$ = i-Pr

The compounds of the invention, such as the compounds of formula (I), are especially suitable for chelating metals, thereby affording compounds of the formula (III):

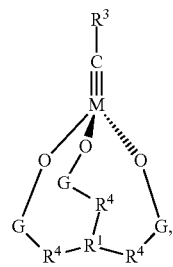

(III)

wherein:
each G moiety of formula (III) is independently an alkyl, aryl or heteroaryl moiety, which is optionally and independently substituted with at least one alkyl, halogen or electron-withdrawing substituent;

$R^1$ is selected from the group consisting of N, $N^+H(A^-)$, $N^+R(A^-)$, B, P, CH, CR, SiR and a 1,3,5-trivalent phenyl moiety, wherein R is optionally substituted alkyl or aryl, and $A^-$ is an anion;

$R^3$ is selected from the group consisting of alkyl, alkyl (aryl) and aryl, all of which are optionally substituted;

$R^4$ is a single bond, heteroatom, or an optionally substituted $C_1$-$C_3$ alkyl chain; and, M is a metal.

In one embodiment, G is selected from the group consisting of optionally substituted phenyl, naphthyl and anthracenyl. In another embodiment, $R^1$ is $N^+H(A^-)$ or $N^+(R)(A^-)$, wherein R is optionally substituted alkyl or aryl, and $A^-$ is an anion. In yet another embodiment, $R^1$ is $N^+(R)(A^-)$. In yet another embodiment, $R^4$ is —$CH_2$—. In yet another embodiment, $R^3$ is methyl, ethyl, propyl, benzyl or phenyl. In yet another embodiment, $R^3$ is ethyl.

In one embodiment, M is a transition metal. In another embodiment, M is selected from the group consisting of Mo, W, Re and Ta. In yet another embodiment, M is Mo.

In one embodiment, the compound of formula (III) is the compound of formula (IV) or a salt thereof:

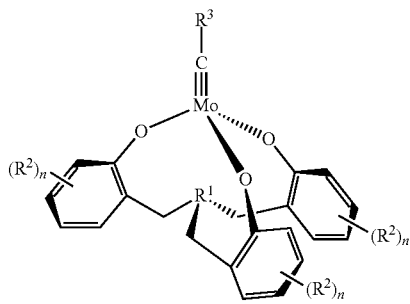

(IV)

wherein:
n is 0, 1, 2, 3, or 4;
each $R^2$ is independently selected from the group consisting of halogen, nitro, cyano, trifluoromethyl, trichloromethyl, carboxy, formyl, lower alkanoyl, carboxyamido and aryl lower alkanoyl;

$R^3$ is alkyl, alkyl(aryl) or aryl, all of which are optionally substituted; and M is selected from the group consisting of Mo, W, Re and Ta.

In one embodiment, $R^1$ is $N^+H(A^-)$ or $N^+(R)(A^-)$, R is optionally substituted alkyl or aryl, and $A^-$ is an anion. In another embodiment, $R^1$ is $N^+(R)(A^-)$. In yet another embodiment, each $R^2$ is independently alkyl, halogen, or $NO_2$. In yet another embodiment, $R^3$ is methyl, ethyl, propyl, benzyl or phenyl. In yet another embodiment, $R^3$ is ethyl. In yet another embodiment, M is Mo. In yet another embodiment, $A^-$ is chloride, bromide, or iodide.

In one embodiment, the compound of formula (IV) is the complex 1 (also known as Mo-L1) or a salt thereof:

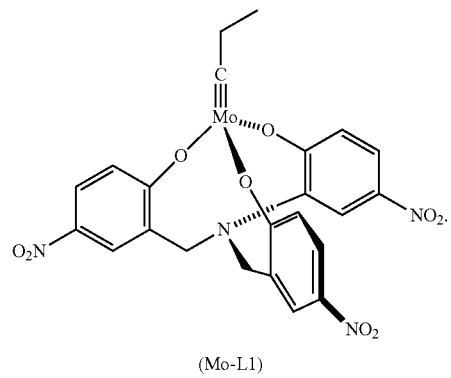

(Mo-L1)

Additional non-limiting examples of compounds of formula (IV) are the complexes provided below:

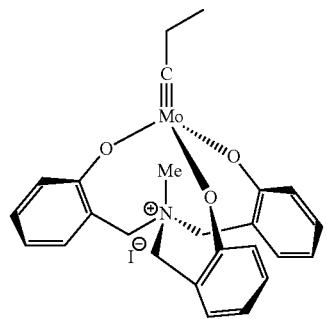

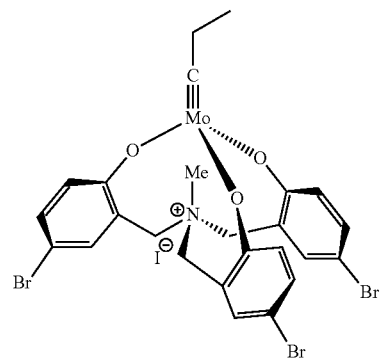

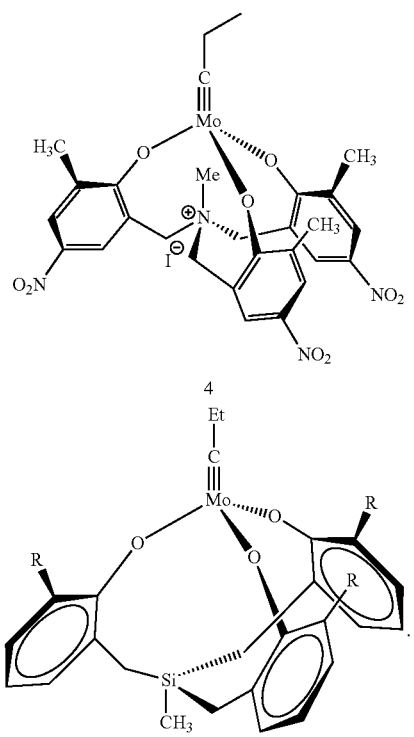

6a: R = H
6b: R = Me
6c: R = i-Pr

Without wishing to be limited by theory, the compounds of the invention take advantage of the favorable trigonal pyramid geometry of tri-substituted amines (Schrock, 1997, Acc. Chem. Soc 30:9), allowing the effective coordination of the three oxygen atoms to the metal center, with the three methylene units blocking one substrate-binding site of the metal center (FIG. 1A).

The single crystal X-ray structure of the Mo-L1 complex showed a phenoxide-bridged dimer of the complex with an octahedral coordination geometry around each Mo (FIG. 1B and Table 7). Interestingly, it was observed that the trigonal pyramid geometry of the triphenolamine ligand enables the coordination of the central nitrogen to the Mo, thus efficiently blocking one open binding site of the complex. In one aspect, these features make the compounds of formula (III), exemplified by the Mo-L1 catalyst, resistant to the interfering alkyne polymerization, and the strong chelating effect of the multidentate ligand can significantly enhance the catalyst stability and its activity.

Without wishing to be limited by theory, compared to those alkyne metathesis catalysts with monodentate ligands, the high catalytic activity and robustness of compounds of formula (III), particularly the Mo-L1 catalyst, can be attributed to two major factors: (i) stronger complexation offered by the multidentate ligand (entropy-favored) in comparison to a monodentate ligand, making the catalyst more robust and elongating its lifetime; and (ii) spatial blocking of one substrate-binding site of the metal-alkylidyne complex substantially inhibits the undesired alkyne polymerization, and also greatly minimizes the non-productive substrate binding, thus enabling the efficient metathesis of heterocycles containing donor moieties. In one aspect, high functional group tolerance, fast reaction rate and high stability represent three great advantages of Mo-L1 catalyst.

The invention also includes an alkyne metathesis catalyst prepared by a method comprising contacting a precursor compound with a compound of formula (I). In one embodiment, the compound of formula (I) is a compound of formula (II).

In one embodiment, the precursor compound is a metal alkylidyne compound having exchangeable ligands. In another embodiment, the precursor compound is the compound recited in Scheme 3 ([tris(N-tert-butyl-N-(3,5-dimethylphenyl)amido) Mo(VI) $R^3$-substituted methylidyne, or a salt theerof], wherein $R_3$ is alkyl, cycloalkyl or aryl, wherein the alkyl, cycloalkyl or aryl is optionally substituted.

Salts

The compounds described herein may form salts with acids or bases, and such salts are included in the present invention. The term "salts" embraces addition salts of free acids or free basis that are useful within the methods of the invention. Salts may possess properties such as high crystallinity, which have utility in the practice of the present invention, such as for example utility in process of synthesis or purification of compounds useful within the methods of the invention.

Suitable acceptable acid addition salts may be prepared from an inorganic acid or from an organic acid. Examples of inorganic acids include perchlorate, hydrochloric, hydrobromic, hydriodic, nitric, carbonic, sulfuric, and phosphoric acids. Appropriate organic acids may be selected from aliphatic, cycloaliphatic, aromatic, aralphatic, heterocyclic, carboxylic and sulfonic classes of organic acids, examples of which include formic, acetic, propionic, succinic, glycolic, gluconic, lactic, malic, tartaric, dibenzoyltartaric, dibenzyltartaric, benzoyltartaric, benzyltartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Synthesis

Ligands

In one aspect, provided herein is a method of making a compound of the formula (IIa) according to Scheme 1:

Scheme 1.

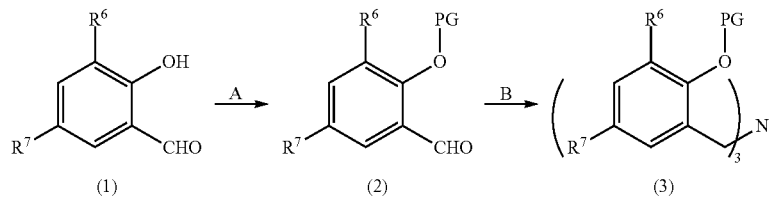

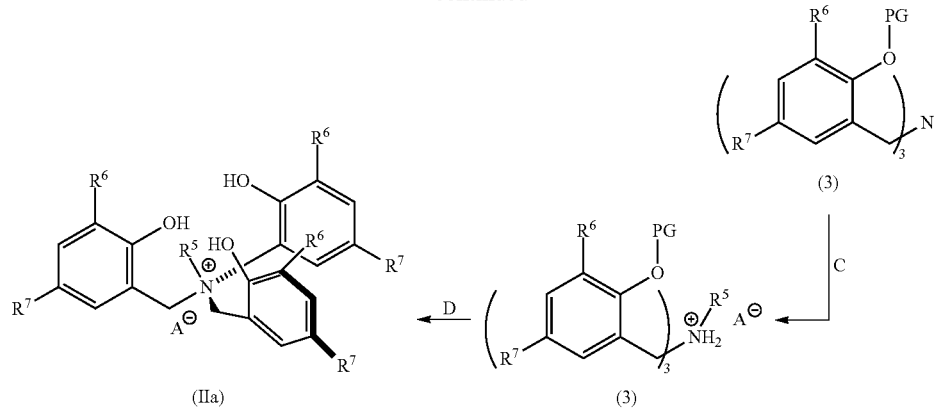

(IIa)

In one embodiment, step A comprises contacting the compound (1) with a hydroxy protecting reagent in a reaction mixture comprising a solvent and a base, such that the compound (2) is formed. Suitable hydroxy protecting reagents are known to those of skill in the art, and include silylating reagents, alkylating agents and acylating agents. In one embodiment, the hydroxy protecting reagent of step A is an alkylating agent. In another embodiment, the alkylating agent is a methylating agent. Non-limiting examples of methylating agents include methyl iodide and dimethyl sulfate. In an embodiment of step A, the hydroxy protecting reagent is methyl iodide.

In one embodiment, the solvent of step A comprises a polar organic solvent, a non-polar organic solvent or water. In another embodiment, the polar organic solvent is a polar, aprotic solvent. In yet another embodiment, the solvent of step A comprises the polar aprotic solvent DMF (dimethylformamide).

In one embodiment, the base of step A is selected from the group consisting of conjugate bases of acetic acid, carbonic acid, phosphoric acid and water. In another embodiment, the base of step A is selected from the group consisting of conjugate bases of carbonic acid. In yet another embodiment, the base of step A is potassium carbonate.

In one embodiment of the method, step B comprises contacting the compound (2) with a reaction mixture comprising a chemical reductant, an ammonium salt, and a solvent, such that the compound (3) is formed. Chemical reductants suitable for the reductive amination of aldehydes are known to those of skill in the art. In one embodiment, the chemical reductant is triacetoxy sodium borohydride. In another embodiment, the ammonium salt is ammonium acetate. In yet another embodiment, the solvent of step B comprises an aromatic solvent, and alcohol solvent, or an ethereal solvent. In yet another embodiment, the solvent of step B comprises THF (tetrahydrofuran).

In one embodiment, in step C the nitrogen can be quaternized with an alkylating agent. In one embodiment, the alkylating agent is a methylating agent. Non-limiting examples of methylating agents include methyl iodide and dimethyl sulfate.

In one embodiment, step D comprises contacting the compound (3) with a reaction mixture comprising a solvent and one or more deprotection reagents, such that the protecting group (PG) of the compound (2) is removed and the compound L1 is formed. Suitable deprotection reagents are known to those of skill in the art, and are selected according to the particular PG group to be removed. In one embodiment, the deprotection reagent of step C is LiI (lithium iodide). In another embodiment, the solvent of step C comprises an organic solvent. In yet another embodiment, the solvent of step C is quinoline.

In one aspect, provided herein is a method of making the ligand L1 according to Scheme 2:

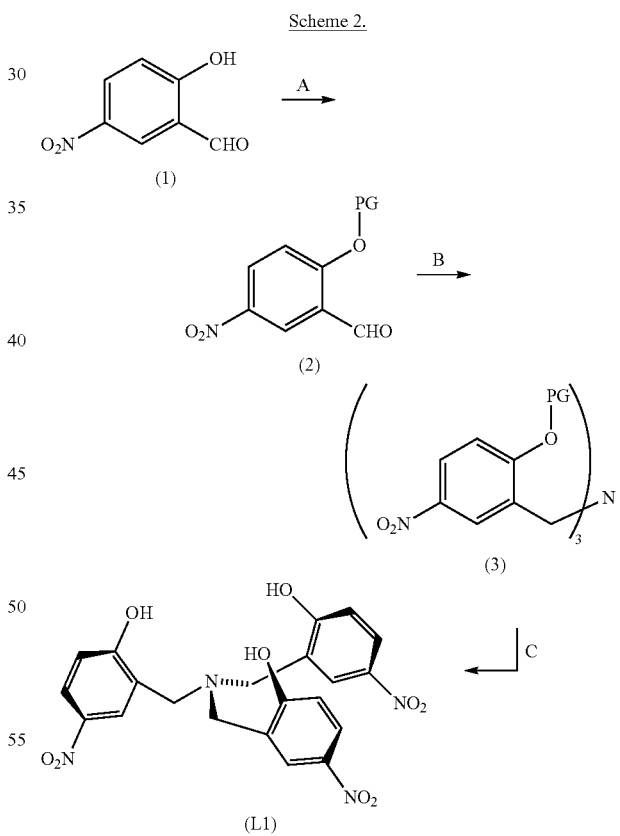

The synthesis of the multidentate triphenolamine ligand (L1) was achieved in good yield starting from the corresponding methyl protected salicyl aldehyde followed by reductive amination and deprotection.

Figure 14:
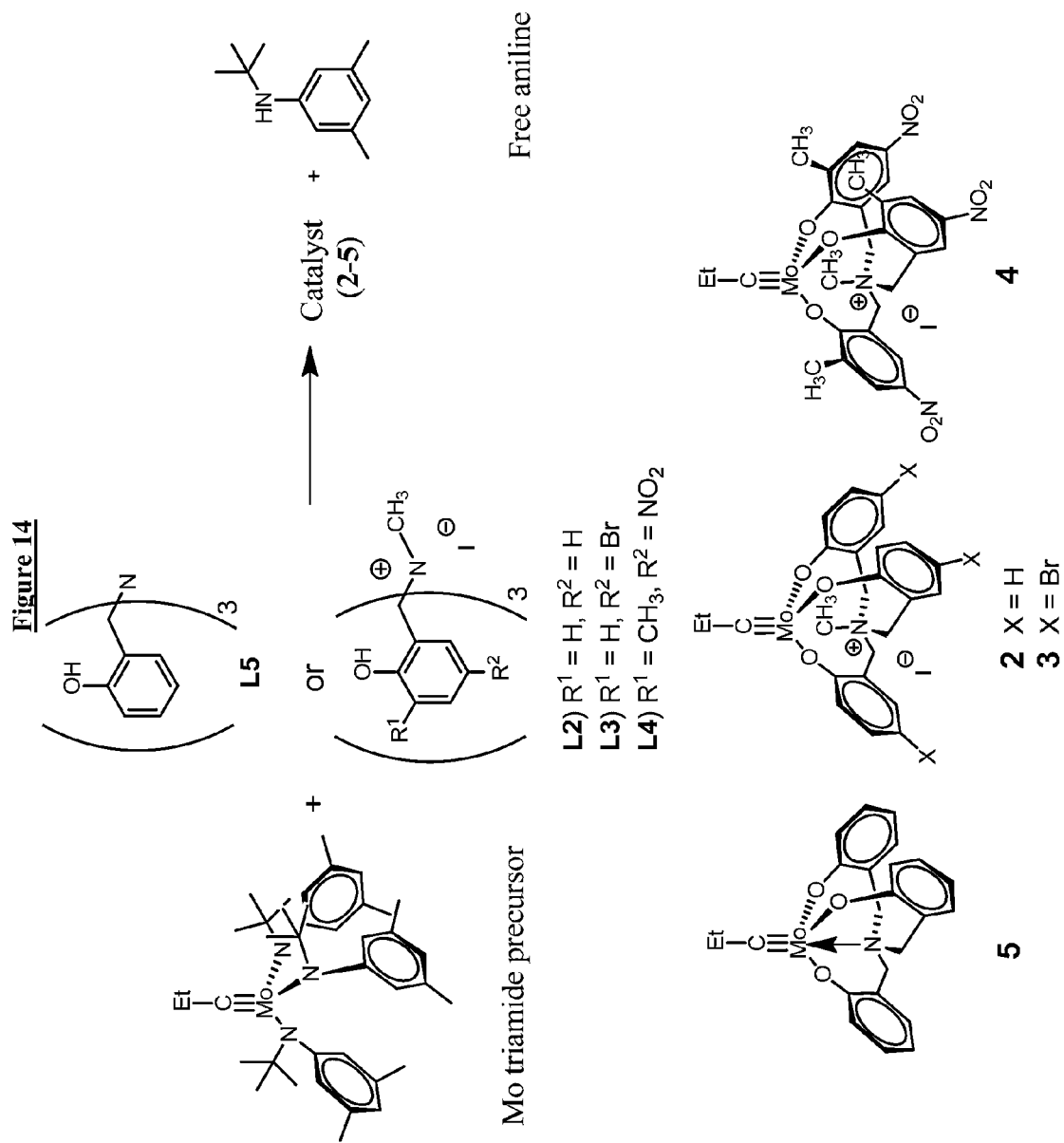
FIG. 14 illustrates generation of triphenolammonium Mo alkylidynes from Mo triamide precursor.
Figure 15:
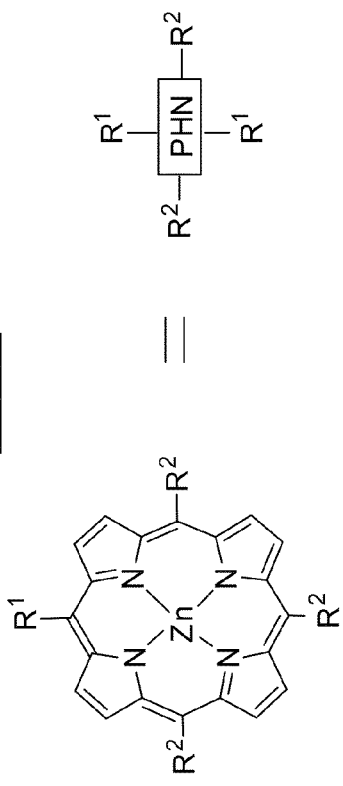
FIG. 15 illustrates generic structure of porphyrin substrates used for alkyne metathesis.

The synthesis of the multidentate ligands (FIG. 14, L2-L5) for catalysts 2-5 was accomplished in good yields starting from the corresponding methyl protected salicyl aldehyde.

Reductive amination and deprotection yielded the multidentate ligand L5, while for the ligands L2-L4 the nitrogen was quaternized with methyl iodide, before the deprotection. For the ligand L4, nitration using dilute $HNO_3$ was conducted after deprotection to provide the final ligand.

Methods of the Invention

The invention includes a method of preparing a catalytic complex, or a salt thereof, wherein the complex comprises a ligand of the invention.

Catalytic Complex

In one embodiment, the catalytic complex is prepared according to Scheme 3:

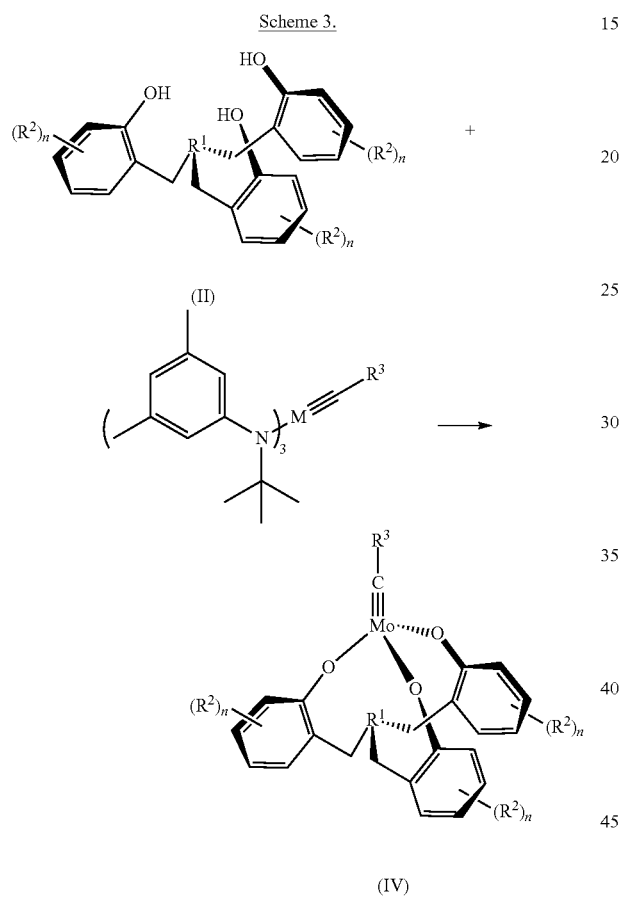

wherein M, $R^1$, $R^2$ and $R^3$ are as defined elsewhere herein. In one embodiment, M is Mo.

The multidentate alkyne metathesis catalyst Mo-L1 has been disclosed in DOI:10.1002/anie.201007559, the contents of which are incorporated herein by reference. A crystal of the Mo-L1 complex was obtained from a 1:1 mixture of the Mo(VI) propylidyne precursor and L1, using a solvent system comprising nitrobenzene and carbon tetrachloride. The crystal was obtained from the mixed solvents after the complex solution was left in the freezer for over two weeks. Due to the extremely poor solubility of the crystal in $CCl_4$, its catalytic activity could not be tested. In nitrobenzene the catalyst had much better solubility, but no metathesis reaction was observed.

Figure 5A:
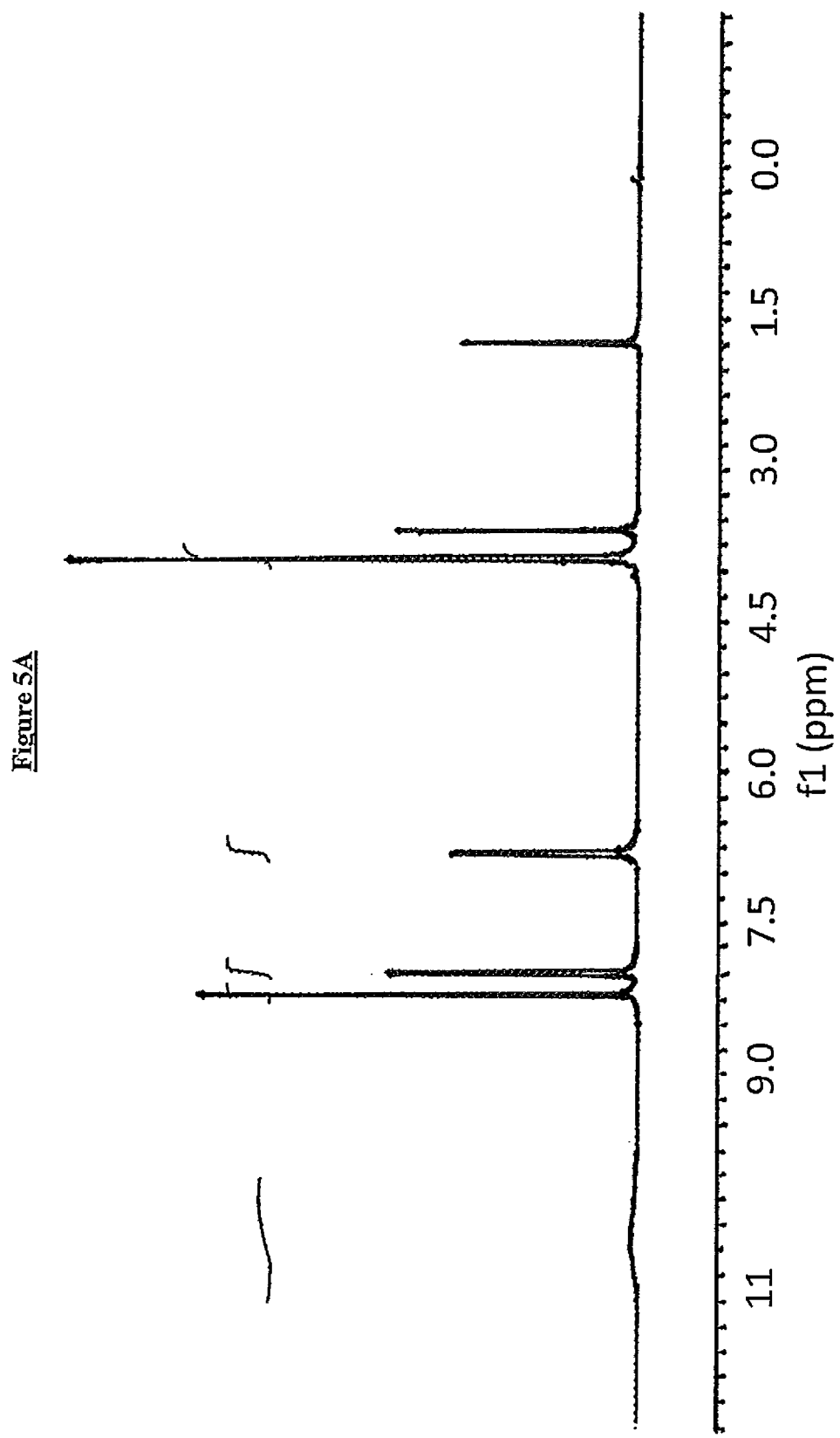
FIGS. 5A-5C, illustrates the $^1H$ NMR spectra (FIG. 5A), $^{13}C$ NMR spectra (FIG. 5B) and $^{15}N$ NMR spectra (FIG. 5C) of the $^{15}N$ labeled ligand L1 in THF-$d_4$.
Figure 5B:
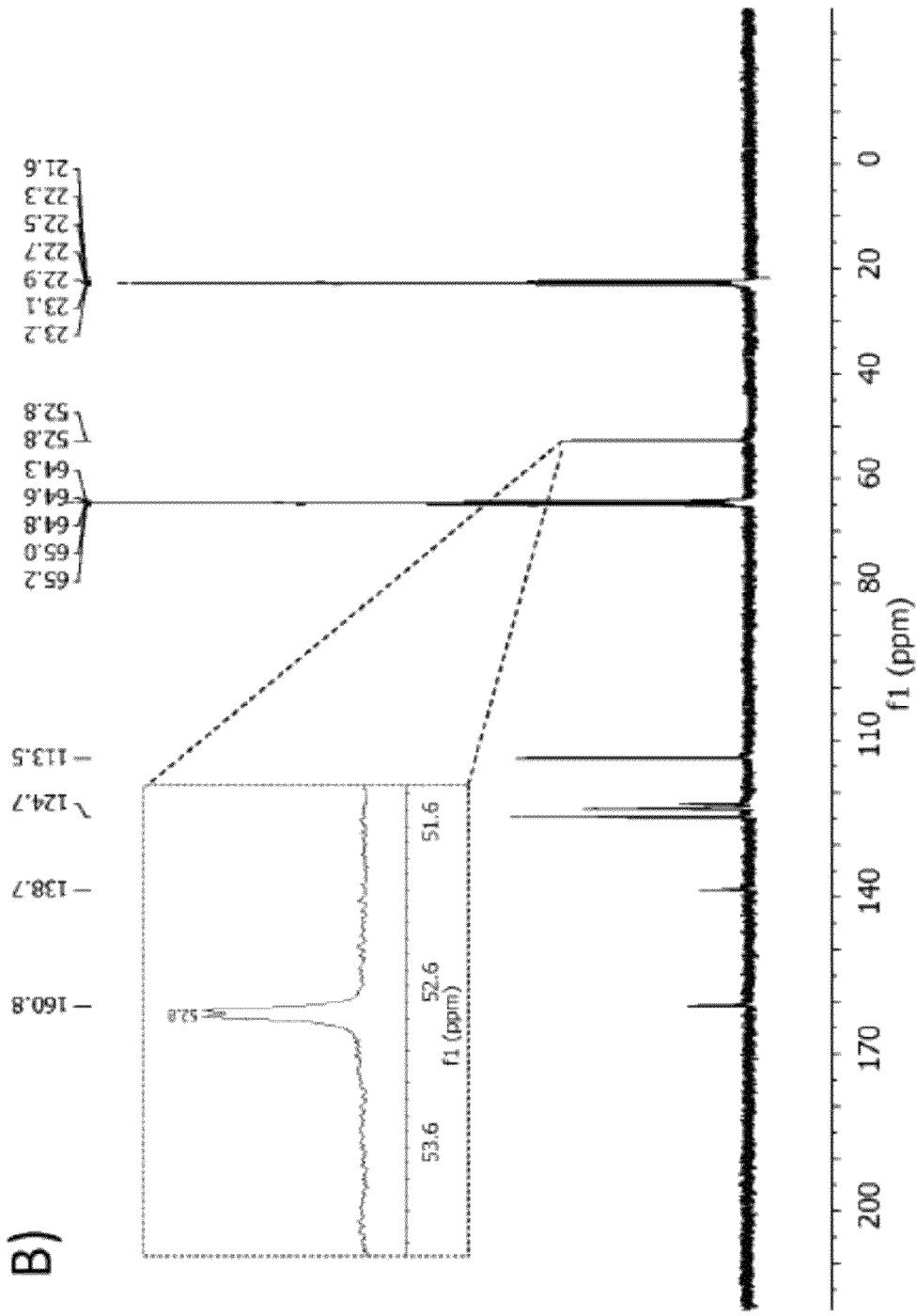
Figure 5C:
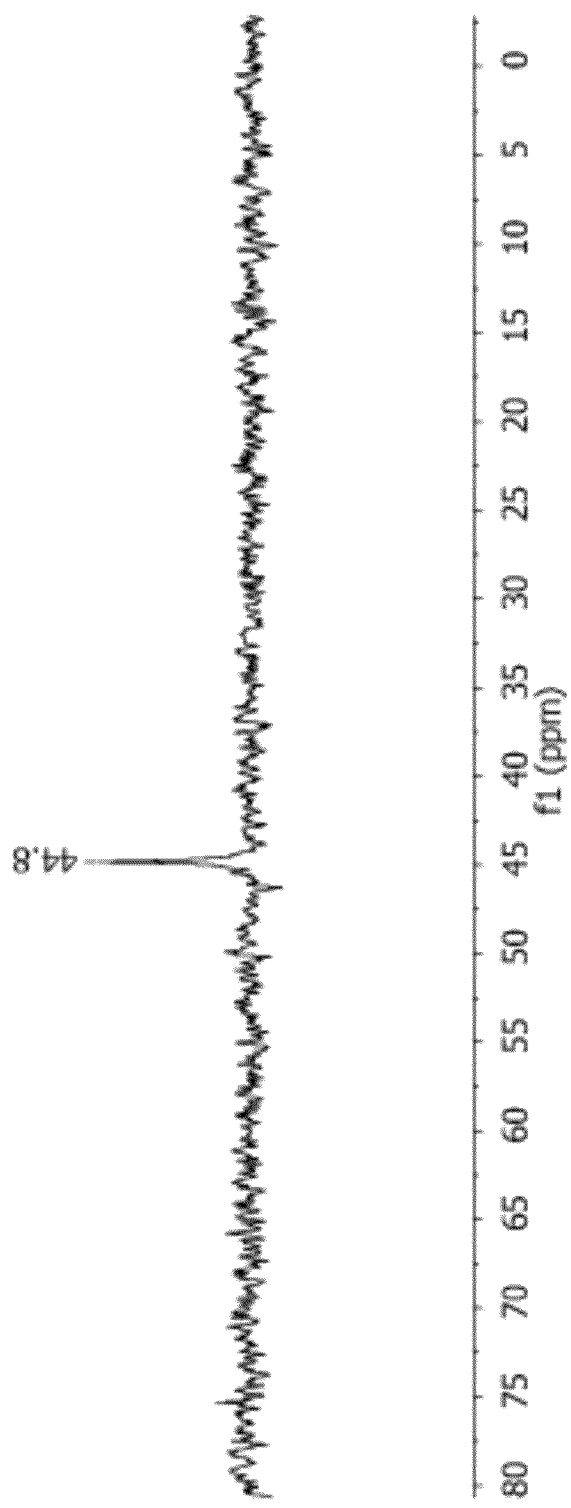
Figure 6A:
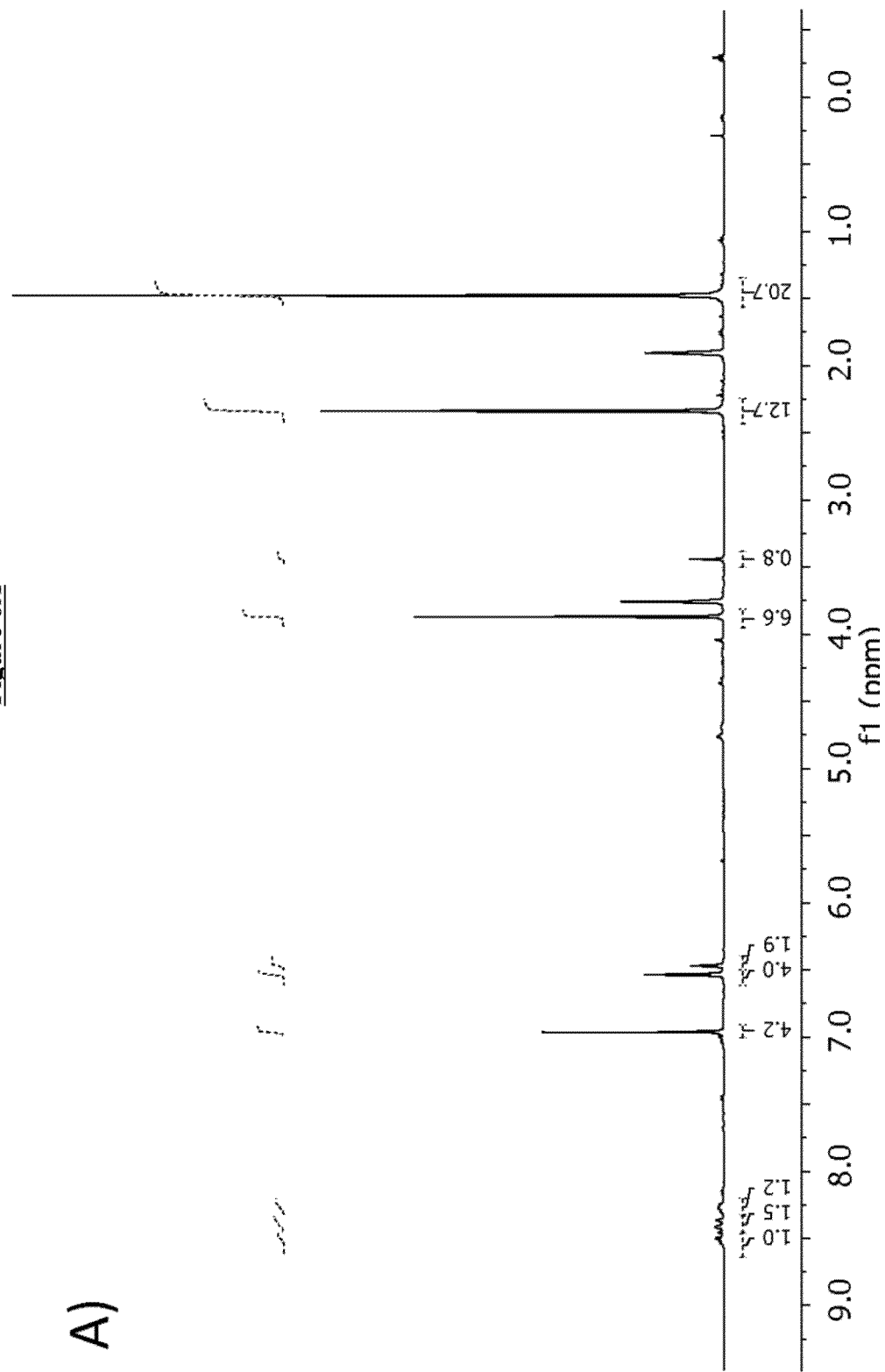
FIGS. 6A-6C, illustrates the $^1H$ NMR spectra (FIG. 6A), $^{13}C$ NMR spectra (FIG. 6B) and $^{15}N$ NMR spectra (FIG. 6C) of the Mo-L1 catalyst in THF-$d_4$.
Figure 6B:
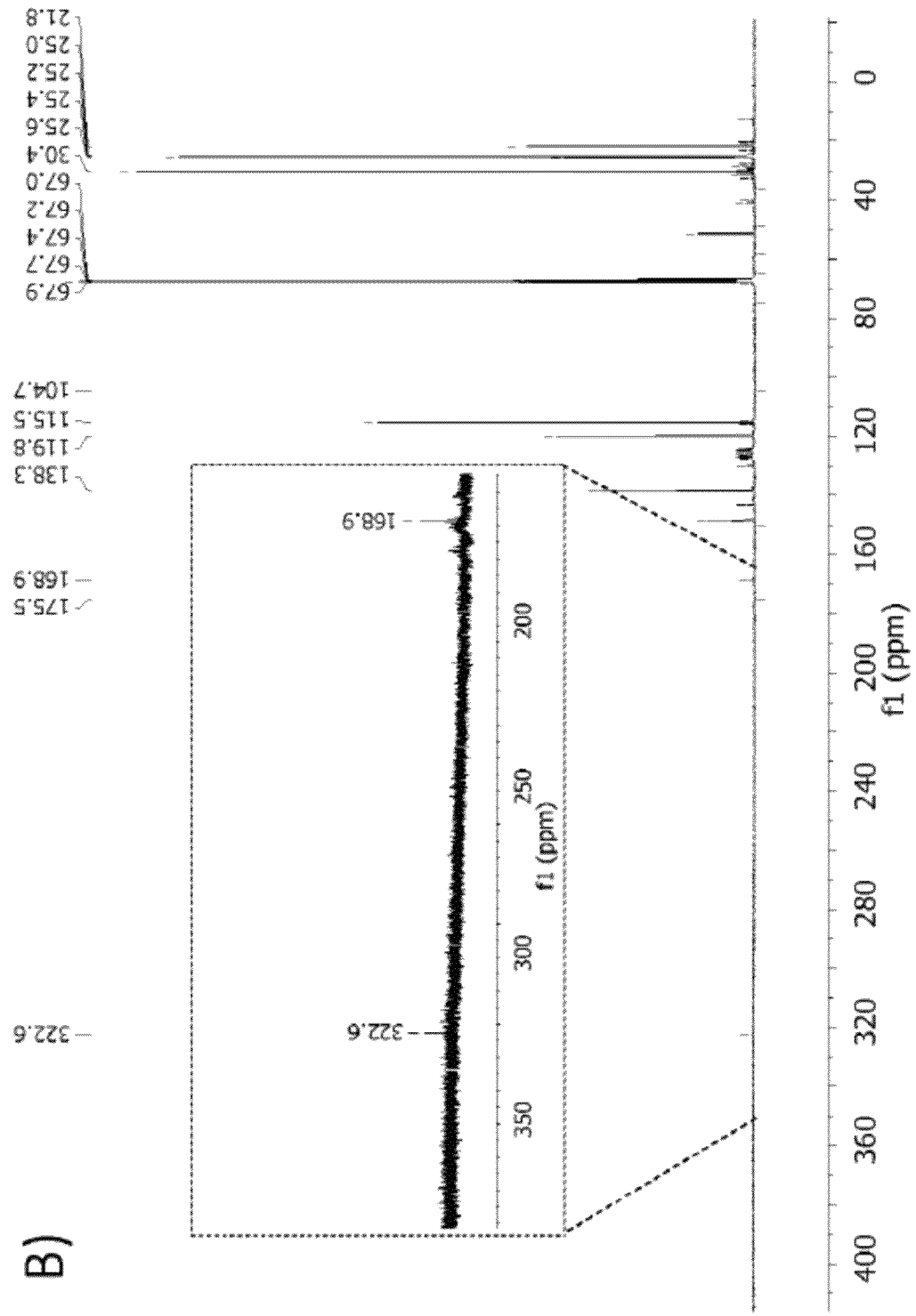
Figure 6C:
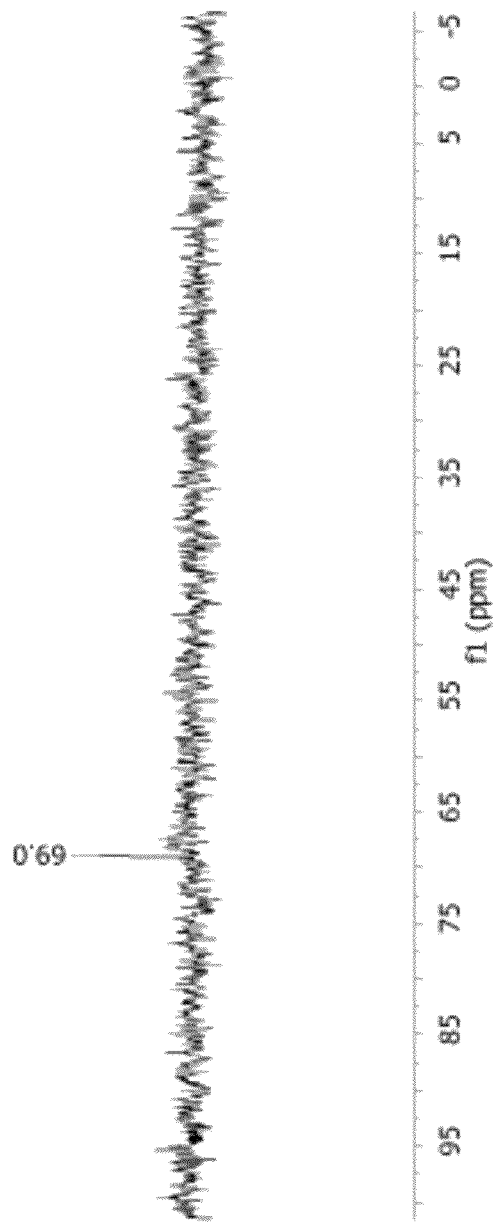
Figure 8:
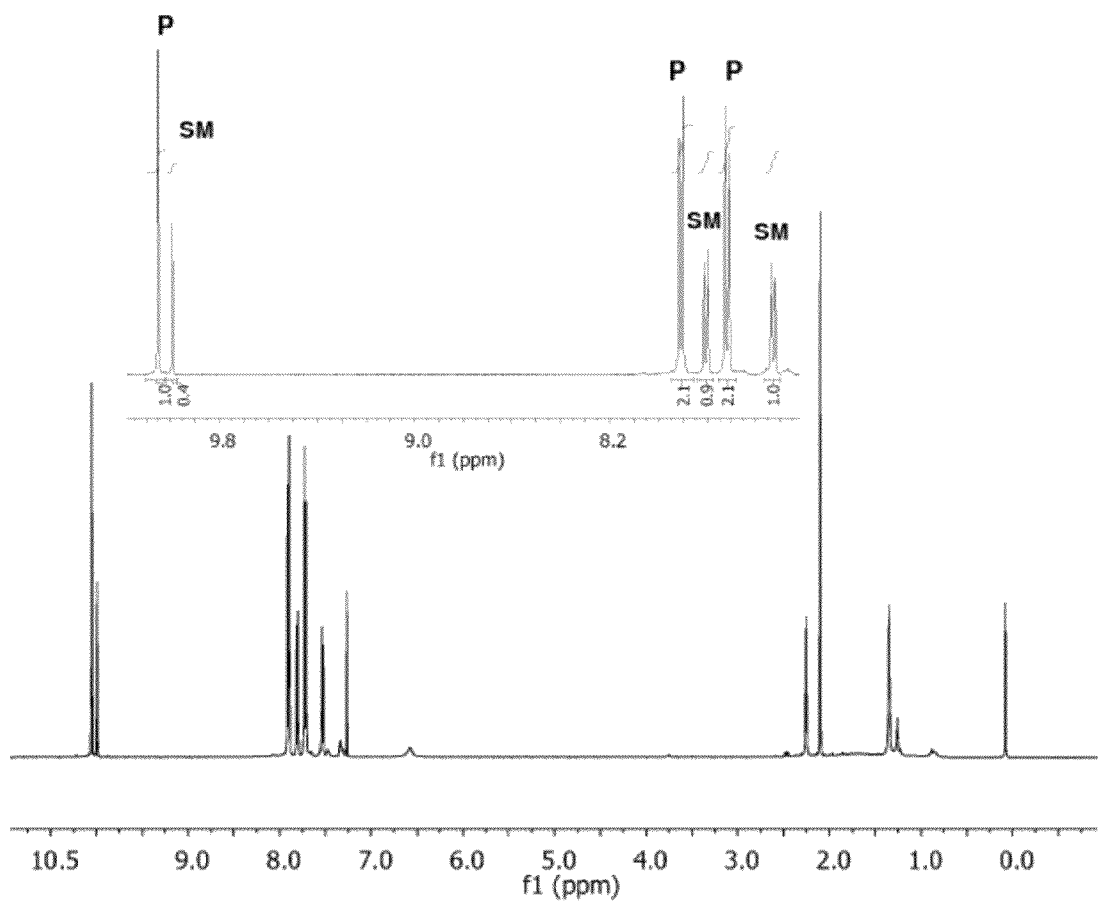
FIG. 8 illustrates a metathesis reaction of entry 3 in Table 1 in $CCl_4$ at 40° C. using 3 mol % loading of Mo-L1. Reaction mixture after 7 h was characterized by $^1H$ NMR spectroscopy; P=Product, SM=Starting material.
Figure 9:
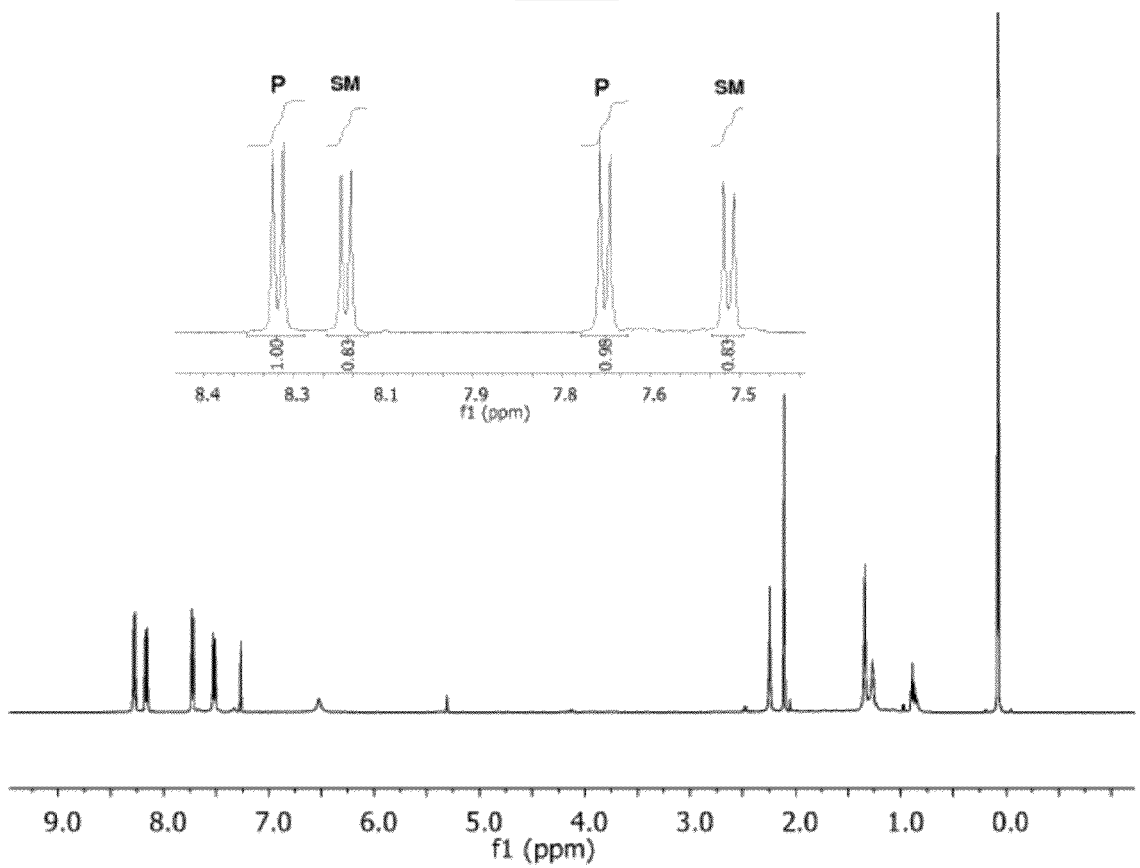
FIG. 9 illustrates a metathesis reaction of entry 4 in Table 1 in $CCl_4$ at 40° C. using 3 mol % loading of Mo-L1. Reaction mixture after 12 h was characterized by $^1H$ NMR spectroscopy; P=Product, SM=Starting material.

$^1$H NMR experiments using 1,4-dimethoxybenzene as an internal standard proved the quantitative displacement of the precursor ligands (FIG. 4) with L1 and the in situ generation of Mo-L1 catalyst in solution phase. In addition, the $^{13}$C NMR analysis of the trisamido Mo(VI) propylidyne precursor, before and after mixing with L1, showed a significant deshielding effect; the chemical shift of the carbyne carbon bonded to the Mo moved from 302.6 ppm to 322.6 ppm, further proving the displacement of anilide ligands on the Mo(VI) propylidyne precursor with L1 (FIGS. 5 and 6). Further, $^{15}$N NMR experiments using a $^{15}$N labeled sample of L1 gave insight into the coordination behavior of the central nitrogen atom to the Mo. The signal observed at 44.8 ppm for the $^{15}$N in the free ligand L1 shifted significantly to 69.0 ppm upon being mixed with the catalyst precursor, which indicates the coordination of the L1 nitrogen to the Mo center to form the multidentate metal complex (FIGS. 5 and 6).

Figure 22:
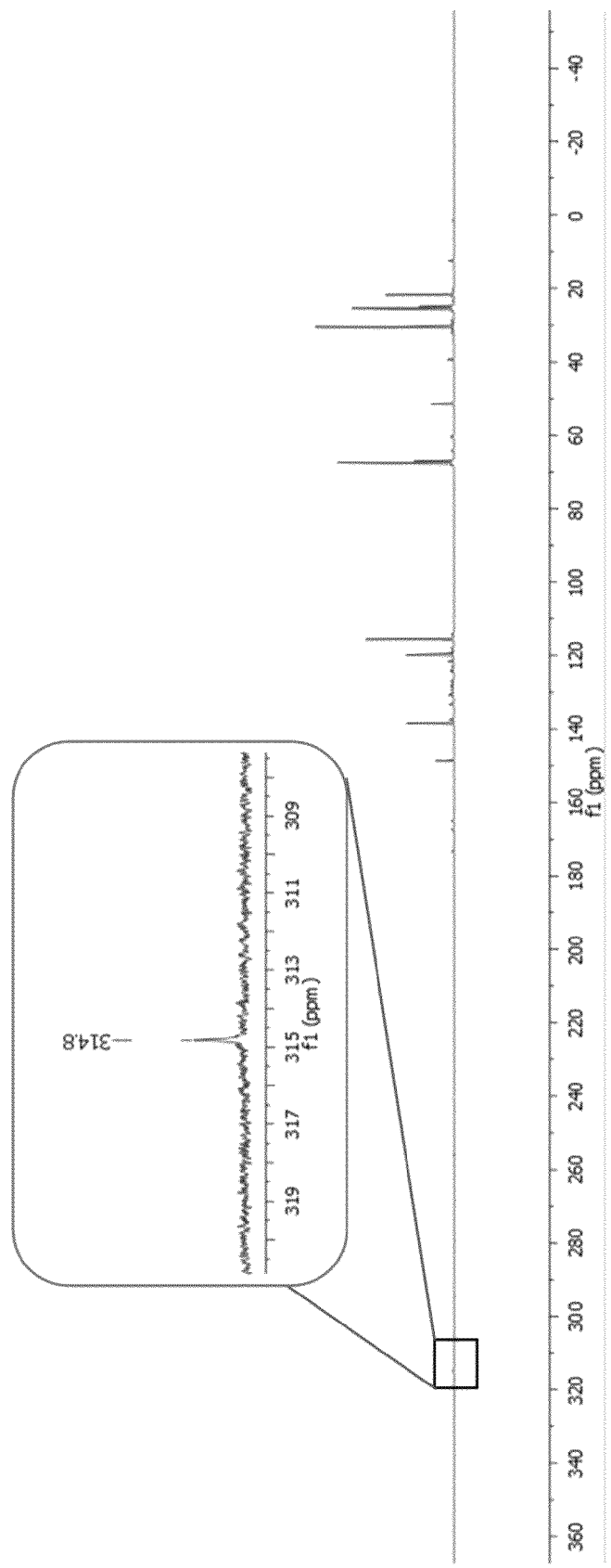
FIG. 22 illustrates the $^{13}C$ NMR spectrum of catalyst 5 in THF-$d_8$.

The catalysts 4-5 were generated in situ from a 1:1 mixture of the Mo(VI) propylidyne precursor (Zhang et al., 2003, Chem. Commun. 832) and the respective ligands in various solvents. The in situ generation of catalyst 5 and 3 was confirmed by $^1$H NMR expedments using 1,4-dimethoxybenzene as an internal standard, which showed a quantitative displacement of the precursor ligands by various tris(arylmethyl) amine ligands to form the multidentate metal complexes (FIG. 21). In addition, the $^{13}$C NMR analysis of the trisamido Mo(VI) propylidyne precursor, before and after mixing with the ligands, showed a significant deshielding effect; the chemical shift of the carbyne carbon bonded to the Mo moved from 302.6 ppm (Zhang et al., 2003, Chem. Commun. 832) to 314.8 ppm for catalyst 5 (FIG. 22), which also supported the successful generation of triol-coordinated Mo(VI) complex.

Alkyne Metathesis

In one aspect, provided herein is a method for performing alkyne metathesis, comprising contacting a first alkyne-containing substrate with a second alkyne-containing substrate in the presence of a compound having the formula (I), for example a compound of formula (IV), such that the metathesis product of the first and second alkyne-containing substrates is formed:

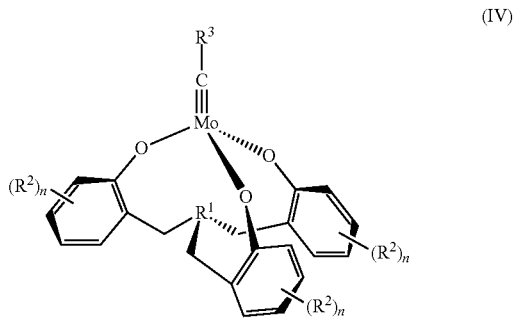

wherein M, $R^1$, $R^2$, $R^3$ and n are as defined elsewhere herein. The first alkyne-containing substrate and the second alkyne-containing substrate may be the same, or they may be different (e.g., cross-metathesis). Together, the first alkyne-containing substrate and the second alkyne-containing substrate can be understood to describe a single molecule with two or more alkyne moieties that are metathesized (e.g., cyclization). The first alkyne-containing substrate and the second alkyne-containing substrate may also include a monomeric species, and an oligomeric species that has been formed in an earlier metathesis iteration (e.g., polymerization).

The alkyne metathesis reactions can be performed in a number of solvents, including, but not limited to, carbon tetrachloride, dichloroethane, chloroform, toluene, chlorobenzene, 1,2-dichlorobenzene, 1,2,4-trichlorobenzene and THF, as well as mixtures thereof.

In one embodiment, the compound of formula (IV) is the catalytic complex Mo-L1:

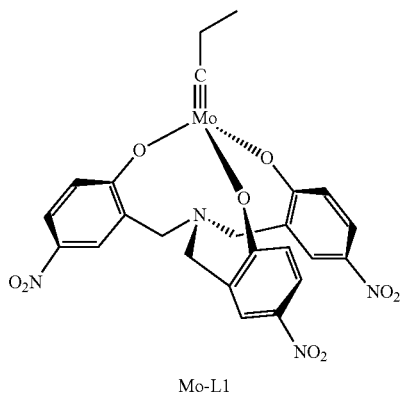

Mo-L1

The solvent compatibility of the Mo-L1 catalyst was tested with 4-propynylanisole as the substrate in a series of solvents (carbon tetrachloride, chloroform, toluene, chlorobenzene, 1,2-dichlorobenzene, 1,2,4-trichlorobenzene and THF, in closed system). The catalyst was metathesis active in all the above solvents (52-70% conversion), and the highest conversion was observed in carbon tetrachloride.

Table 1 summarizes some model experiments by using the in situ generated Mo-L1 catalyst system, with carbon tetrachloride as the solvent. The scope of the metathesis activity was probed with various substrates (i) containing electron donating/withdrawing substituents (ii) heterocyclic molecules, (iii) the ring closing alkyne metathesis (RCAM) of diynes to cycloalkyne and (iv) 1,4-diynes that are generally considered as difficult substrates, presumably due to the formation of undesired stable metal-diyne chelates (Huc et al., 2003, New J. Chem. 27:1412). Interestingly, Mo-L1 was compatible with all the different substrates tested, even those challenging ones containing nitro and aldehyde functional groups that are known to shut down the activity of some highly active alkyne metathesis catalysts (Heppekausen et al., 2010, J. Am. Chem. Soc. 132:11045; Bindl et al., 2009, J. Am. Chem. Soc. 131:9468; some tungsten alkylidynes react with carbonyl groups, see Freudenberger & Schrock, 1986, Organometallics 5:398; Pschirer & Bunz, 1999, Tetrahedron Lett. 40:2481).

All the metathesis products were obtained in good to excellent yields under ambient conditions. In one aspect, applying continuous vacuum to the reaction may further enhance the yields. In particular, the Mo-L1 catalyst gave the highest yield so far among the literature reports (Haberlag et al., 2010, Chem. Eur. J. 16:8868; Pschirer & Bunz, 1999, Tetrahedron Lett. 40:2481) for the metathesis of p-nitro substituted propynyl benzene, thus substantiating its high catalytic activity. Half-lives of less than 1 hour were generally observed for these model reactions, even with catalyst loading as low as 3 mol % (based on Mo). Successful metathesis of 1,4-diynes opens new possibilities for preparing cross-conjugated polymeric or cyclic molecules.

TABLE 1

| Entry | Substrate | Product | Yield (%) |
|---|---|---|---|
| 1) | H₃CO—⌬—≡— | H₃CO—⌬—≡—⌬—OCH₃ | 87[b] |
| 2) | Cl—⌬—≡— | Cl—⌬—≡—⌬—Cl | 80[b] |
| 3) | OHC—⌬—≡— | OHC—⌬—≡—⌬—CHO | 71[b] |
| 4) | O₂N—⌬—≡— | O₂N—⌬—≡—⌬—NO₂ | 55[b] |
| 5) | thiophene—≡— | thiophene—≡—thiophene | 74[b] |
| 6) | diyne diester | cyclic diyne diester | 93[b] |

TABLE 1-continued

| Entry | Substrate | Product | Yield (%) |
|---|---|---|---|
| 7) | 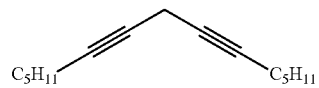 |  | 60[c] |
| 8) | 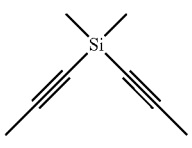 |  | 44 (45)[b/d] |

Reaction conditions: room temperature for entries 1-2, and 40° C. for entries 3-8, reaction times: 4-7 h for entries 1, 2, 5-8, and 7-12 h for entries 3-4. 3 mol % catalyst loading for all entries.
[b]In closed system (solvent CCl$_4$), with the reaction solution exposed to vacuum for 4-5 times to remove the metathesis byproduct 2-butyne.
[c]No removal of the byproduct alkyne, equilibrium conditions.
[d]The number in parenthesis indicates the isolated monoanisole silane.

Given the high functional group tolerance and metathesis activity of Mo-L1, the idea of utilizing the multidentate structural feature to inhibit small alkyne polymerization was tested with 2-butyne, the metathesis byproduct of propynyl substrates. Indeed, as hypothesized, even in the presence of a large excess of 2-butyne (>100 equiv), Mo-L1 did not show any polymerization (FIG. 7) even after 24 hours. However, the catalyst generated from the corresponding monodentate analogue 4-nitrophenol (Mo-L6) (FIG. 1A), showed a broad peak around 1.7-2.0 ppm (FIG. 7) within 1 h after exposure to 2-butyne, thus indicating significant polymerization occurred (Table 2, entry 9).

TABLE 2

| | | | Yield (%)[b] | |
|---|---|---|---|---|
| Entry | Substrate | Product | Mo—L$_1$ | Mo—L$_2$ |
| 9) | H$_3$C—≡—CH$_3$ | 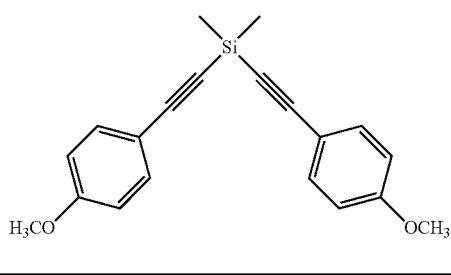 | NR | 40 |
| 10) | 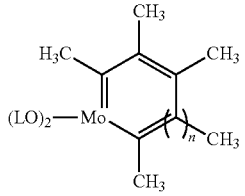 | 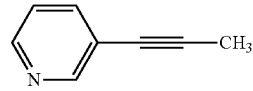 | 61 | NR |
| 11) | 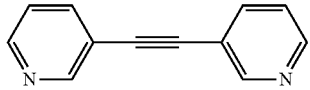 | 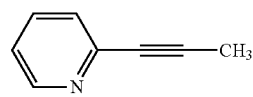 | 20 | NR |

TABLE 2-continued

| Entry | Substrate | Product | Yield (%)[b] Mo—L₁ | Mo—L₂ |
|---|---|---|---|---|
| 12) | 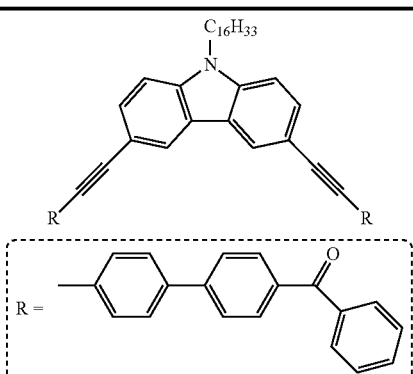 | 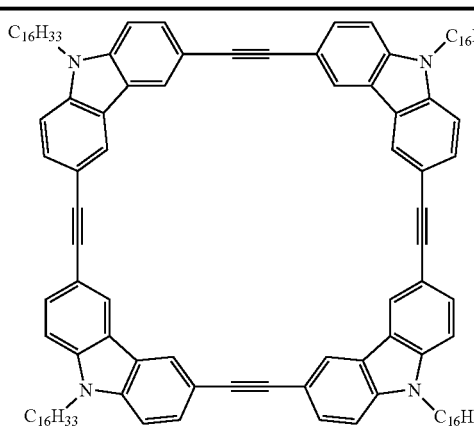 | 95 (2n)[c] | 84 (22h)[c] |

Reaction conditions: room temperature for entry 9, 70° C. for entries 10, 11 and 15, 30° C. for entry 12, reaction times: 24 h for entry 9 and 3 h for entries 10-11. 3 mol % catalyst loading for entries 9, 10, 12, and 7 mol % for entry 11.
[b]In closed system (solvent CCl₄).
[c]Number in parenthesis indicates the reaction time.
NR = No reaction.

Figure 10:
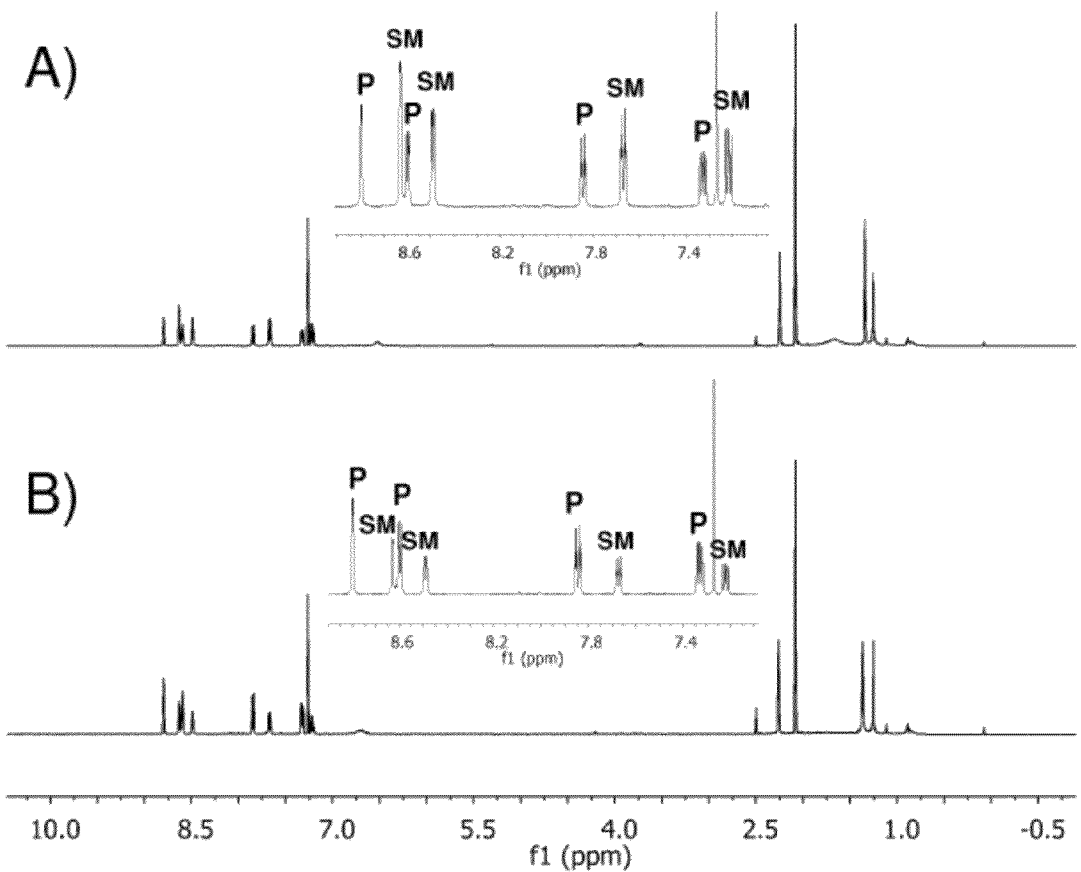
FIG. 10, comprising
Figure 11:
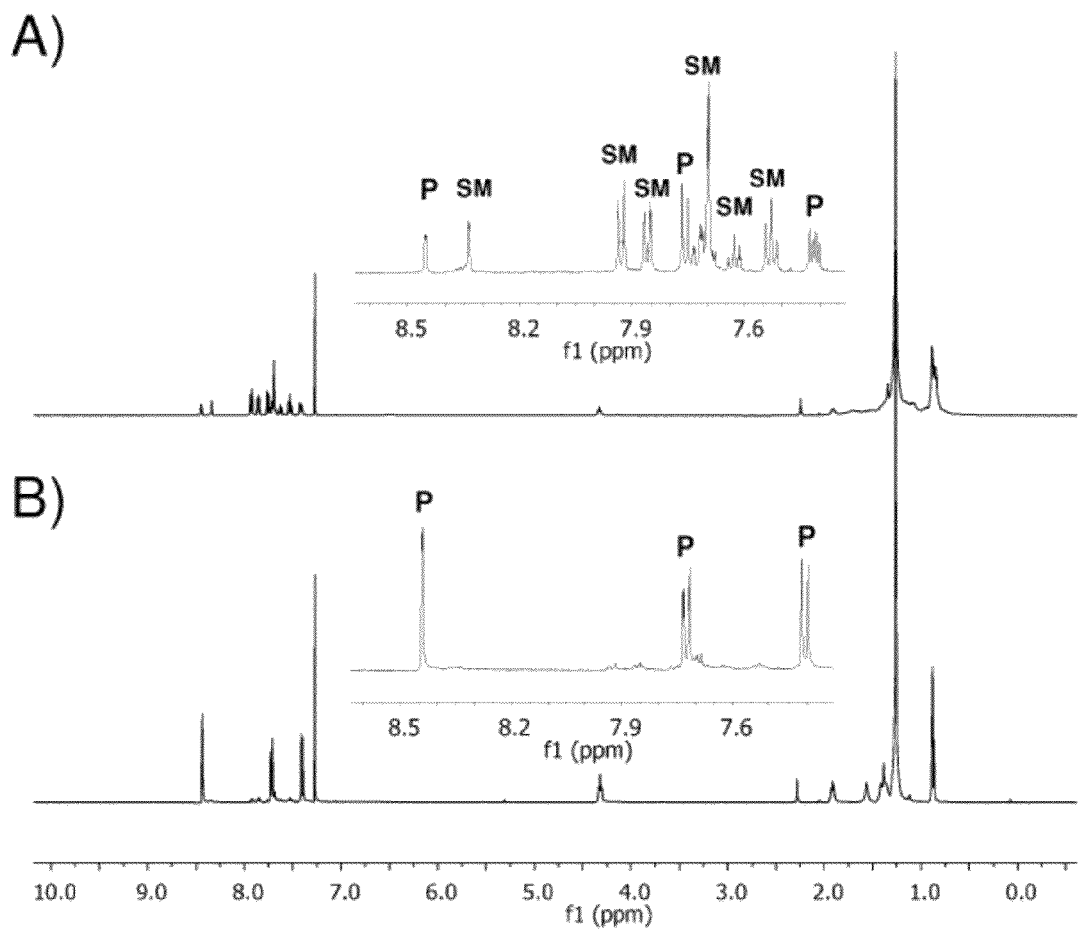
FIG. 11, comprising
Figure 12:
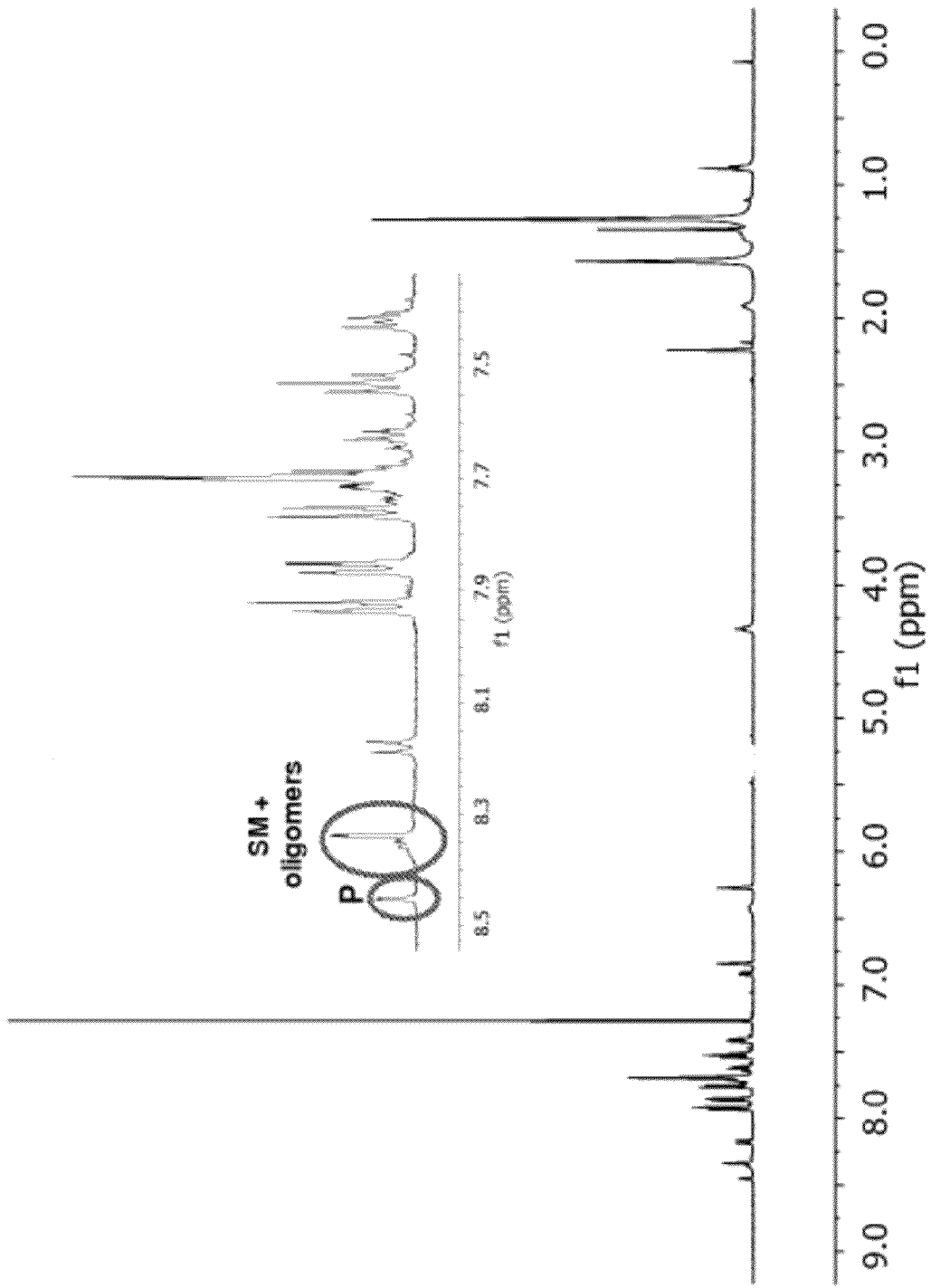
FIG. 12 illustrates precipitation driven cyclooligomerization of diyne monomer 12 in Table 2 in $CCl_4$ at 30° C. using 3 mol % loading of Mo-L6 catalyst. Reaction mixture after 12 h was characterized by $^1H$ NMR spectroscopy; P=Product, SM=Starting material.
Figure 13:
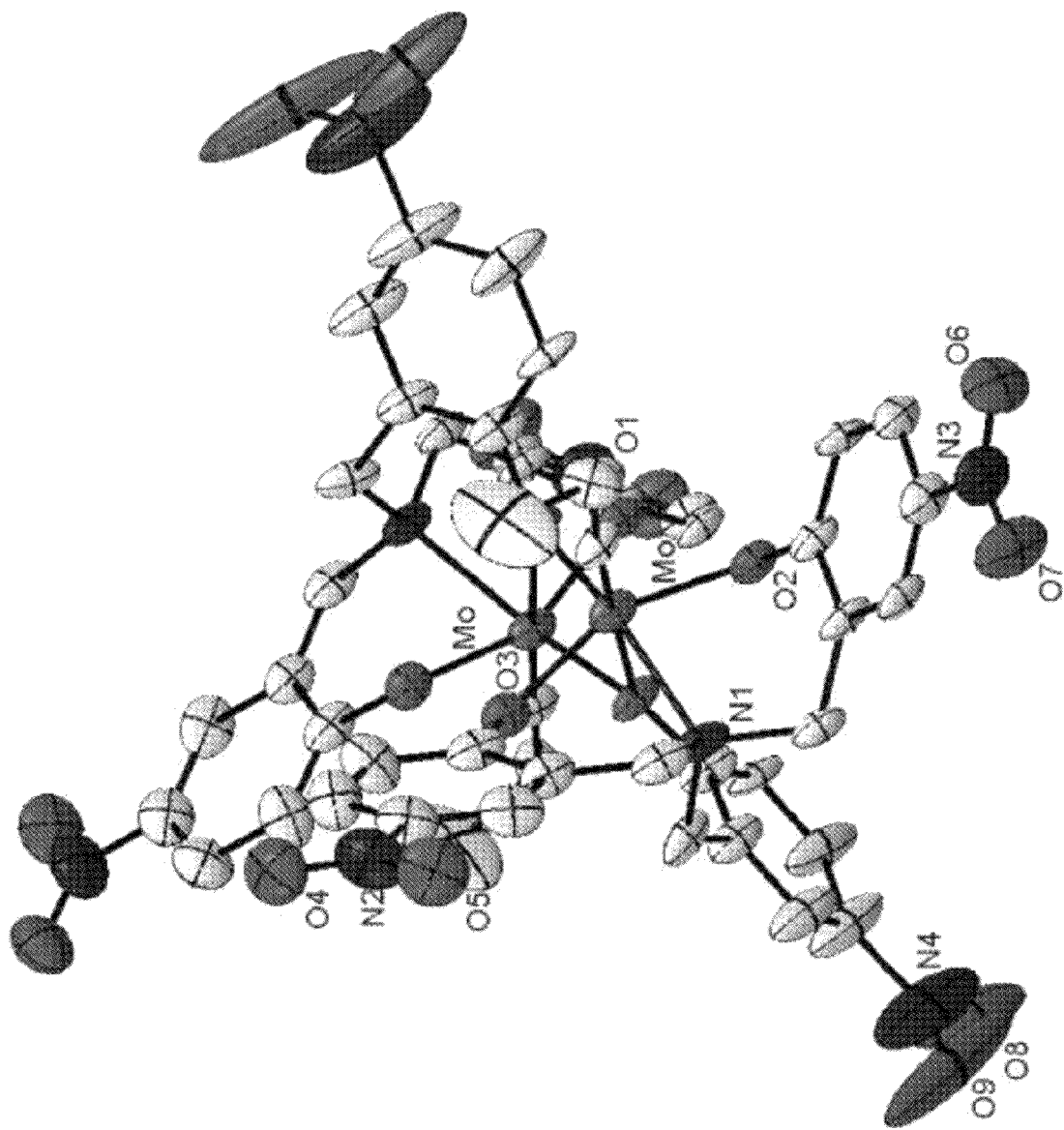
FIG. 13 illustrates a crystal structure of the Mo-L1 dimer complex. A small molecule with the structural formula of $C_6H_{10}$ (likely 3-hexyne) that is not bonded with the complex was removed.

A comparison of the metathesis activity of Mo-L1 versus Mo-L6 (Zhang et al., 2007, Adv. Synth. Catal. 349:93; Fischer et al., 2010, Angew. Chem. 122:415; 2010, Angew. Chem. Int. Ed. 49:7257; Zhang & Moore, 2006, Angew. Chem. 118:4524; 2006, Angew. Chem. Int. Ed. 45:4416; Zhang & Moore, 2005, J. Am. Chem. Soc. 127:11863; Zhang & Moore, 2004, J. Am. Chem. Soc. 126:12796) showed that the newly designed multidentate Mo catalyst has even higher catalytic activity and broader substrate scope. In particular, the metathesis of substrates containing donor moieties such as the pyridine substrates (entries 10-11 in Table 2) failed when Mo-L6 was used even with high catalyst loading (10-15 mol %). In great contrast, the same substrates were successfully metathesized by Mo-L1 catalyst (FIG. 10). o-Propynylpyridine is a very tough substrate, and its homodimerization via alkyne metathesis has not been reported before. Using Mo-L1, catalytic metathesis (entry 11 in Table 2) was accomplished, thus further showing the superior activity of Mo-L1 catalyst. The precipitation-driven cyclo-oligomerization (Zhang & Moore, 2004, J. Am. Chem. Soc. 126:12796) of diyne monomer (entry 12 in Table 2) via alkyne metathesis further substantiated the high activity of Mo-L1; even with 3 mol % catalyst loading, the reaction completed within 2 h at 30° C. with a yield of 95% (FIG. 11). In contrast, for Mo-L6, with 10 mol % catalyst loading, the same transformation took 22 h to give a yield of 84% (Zhang & Moore, 2004, J. Am. Chem. Soc. 126:12796). It was also observed that, reducing the catalyst loading to 3 mol % significantly lowered the reaction conversion when Mo-L6 was used (FIG. 12).

The multidentate Mo-L1 catalyst also showed much higher stability than Mo-L6. The metathesis activity of these two catalysts at different time intervals after their in situ generation (in the absence of substrates) was compared, with 4-chloropropenyl-benzene as the substrate. Mo-L1 showed a comparable activity (<10% decrease) even after 24 hours and retained appreciable catalytic activity for several days, while Mo-L6 showed activity only within the first few hours. For Mo-L6, adding the substrate in the very beginning to the pre-generated catalyst solution led to longer catalyst lifetime. This indicates an intermolecular decomposition pathway (Schrock, 2005, Chem. Commun. 2773) for Mo-L6, either through ligand loss by cleavage of the labile Mo—O bond or by catalyst dimerization. The presence of substrates likely minimizes the bimolecular reaction of the catalyst itself, thus extending its life time. For Mo-L1, the multidentate ligand may bind more strongly to the Mo center due to the chelating effect and the favorable structural features extends its lifetime.

In one embodiment, the compound of formula (IV) is one of the following catalytic complexes:

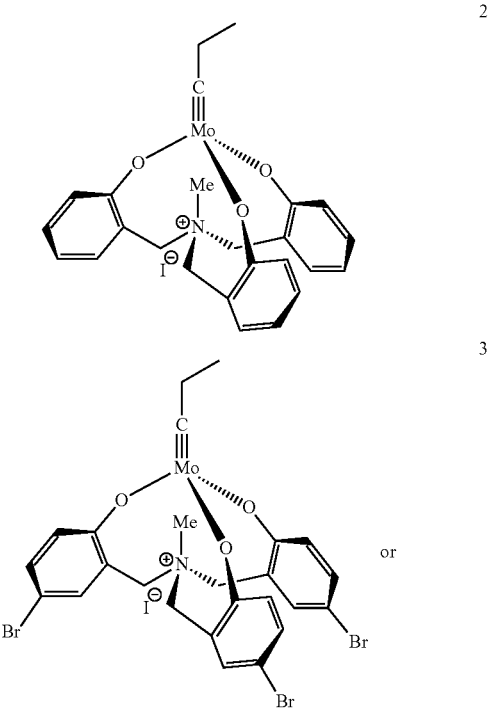

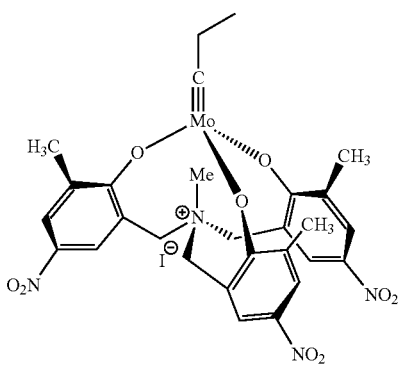

The metathesis activity of 5 (FIG. 14) was examined by using 4-propynylanisole as the substrate. Interestingly, no metathesis reaction was observed even at elevated temperature (70° C.) and with higher catalyst loading (up to 15 mol %). This is presumably due to the N—Mo coordination, which significantly increases the Mo electron density, makes the metal less electrophilic, and thereby shuts down its catalytic activity. In great contrast, complex 2, the N-quaternized analogue of 5, showed high catalytic activity towards most of the substrates tested, including pyddine and benzaldehyde substrates (Table 3). The X-ray photoelectron spectroscropy (XPS) also showed an increased electron binding energy of Mo 3d (2.7 eV, FIG. 23) of catalyst 2 vs catalyst 5, which was consistent with the observed higher activity of 2.

The solvent compatibility of catalyst 2 was tested, with 4-propynylanisole as the substrate, in a series of solvents (carbon tetrachloride, dichloroethane, chloroform, toluene, chlorobenzene, 1,2-dichlorobenzene, 1,2,4-trichlorobenzene and THF, in a closed system). The catalyst was metathesis active in all the above solvents. A small percentage of $CCl_4$ (25 vol %) significantly enhanced the reaction conversion in all the above solvents, and in those mixed solvents containing dichloroethane, chloroform or chlorobenzene, the conversion was comparable to that observed in pure $CCl_4$.

Table 3 summarizes some model experiments by using the in situ generated catalyst 2, in closed system with periodic exposure of the reaction solution to vacuum to remove the 2-butyne byproduct. The scope of the metathesis activity was probed with various substrates (i) containing electron donating/withdrawing substituents (ii) heterocyclic molecules, (iii) the ring closing alkyne metathesis (RCAM) of diynes to cycloalkyne and (iv) the precipitation driven cyclooligomelization reaction of the carbazole substrate. For details on precipitation driven metathesis reactions, see: Zhang & Moore, 2004, J. Am. Chem. Soc. 126:12796; Zhang & Moore, 2005, J. Am. Chem. Soc. 127:11863. All the metathesis products were obtained under ambient conditions. Half-lives of less than 1 hour were generally observed for these model reactions, even with catalyst loading as low as 2-3 mol % (based on Mo).

TABLE 3

Homodimerization, RCAM and cyclo-ologomerization reactions of propynyl substrates

| Entry | Substrate | Product | Yield (%) |
|---|---|---|---|
| 1) | H₃CO–⌬–≡– | H₃CO–⌬–≡–⌬–OCH₃ | 94[a] |
| 2) | Cl–⌬–≡– | Cl–⌬–≡–⌬–Cl | 87[a] |
| 3) | OHC–⌬–≡– | OHC–⌬–≡–⌬–CHO | 80[a] |
| 4) | O₂N–⌬–≡– | O₂N–⌬–≡–⌬–NO₂ | 43[a] |
| 5) | thiophene–≡– | thiophene–≡–thiophene | 84[a] |
| 6) | pyridyl–≡– | pyridyl–≡–pyridyl | 79[a] |

TABLE 3-continued

Homodimerization, RCAM and cyclo-ologomerization reactions of propynyl substrates

| Entry | Substrate | Product | Yield (%) |
|---|---|---|---|
| 7) | | | 95[a] |
| 8) | | | 94[b] |

Reaction conditions: 40° C., CCl$_4$, 2-3 mol % catalyst loading for all entries. Reaction times: 5-8 h for entries 1, 2, 5, 7; 9-13 h for entries 3, 4, 6; 30 min for entry 8.
[a]In closed system, with the reaction solution exposed to vacuum for 6-8 times to remove the metathesis byproduct 2-butyne.
[b]In closed system, without vacuum exposure.

In addition, the efficient inhibition of small alkyne polymerization by the multidentate-ligand structural feature (see, e.g., Jyothish et al., 2011, Angew. Chem. 123:3497; 2011, Angew. Chem. Int. Ed. 50:3435) was tested with 2-butyne as the substrate, which is the metathesis byproduct of propynyl substrates. Indeed, even in the presence of a large excess of 2-butyne (>100 equiv), catalyst 2 did not show any polymerization even after 24 hours. However, the catalyst generated from phenol, the corresponding monodentate analogue, showed significant alkyne polymerization occurred within 1 h after exposure to 2-butyne. Without wishing to be bound by theory, this result suggests that blocking of N—Mo coordination through N-quaternization can significantly enhance the catalyst activity of these Mo-tris(arylmethyl)amine complexes without sacrificing their capability of resisting the alkyne polymerization side reaction.

Figure 24B:
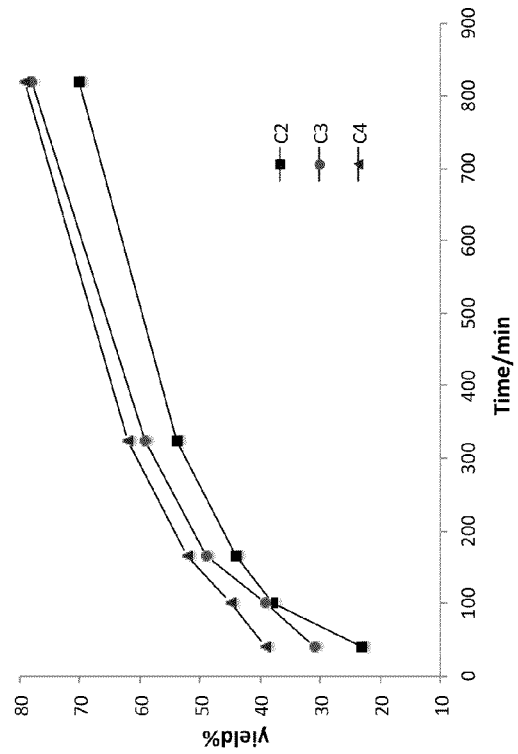
FIGS. 24A-24C, is a series of graphs illustrating kinetic studies.
Figure 24A:
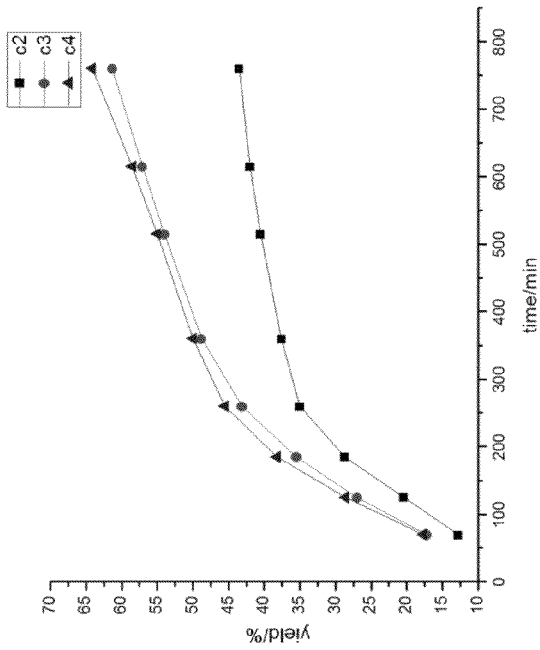
Figure 24C:
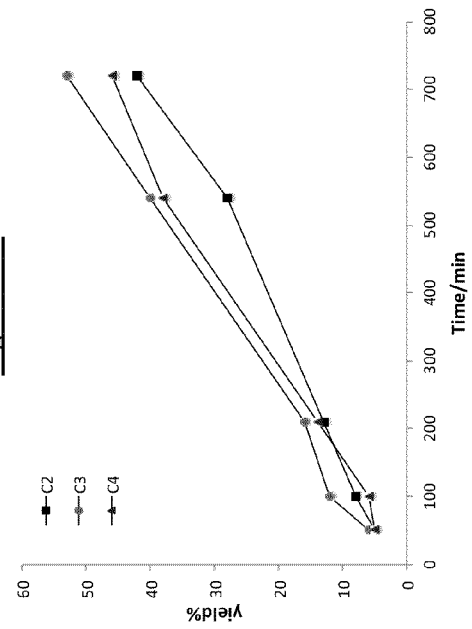
Figure 25:
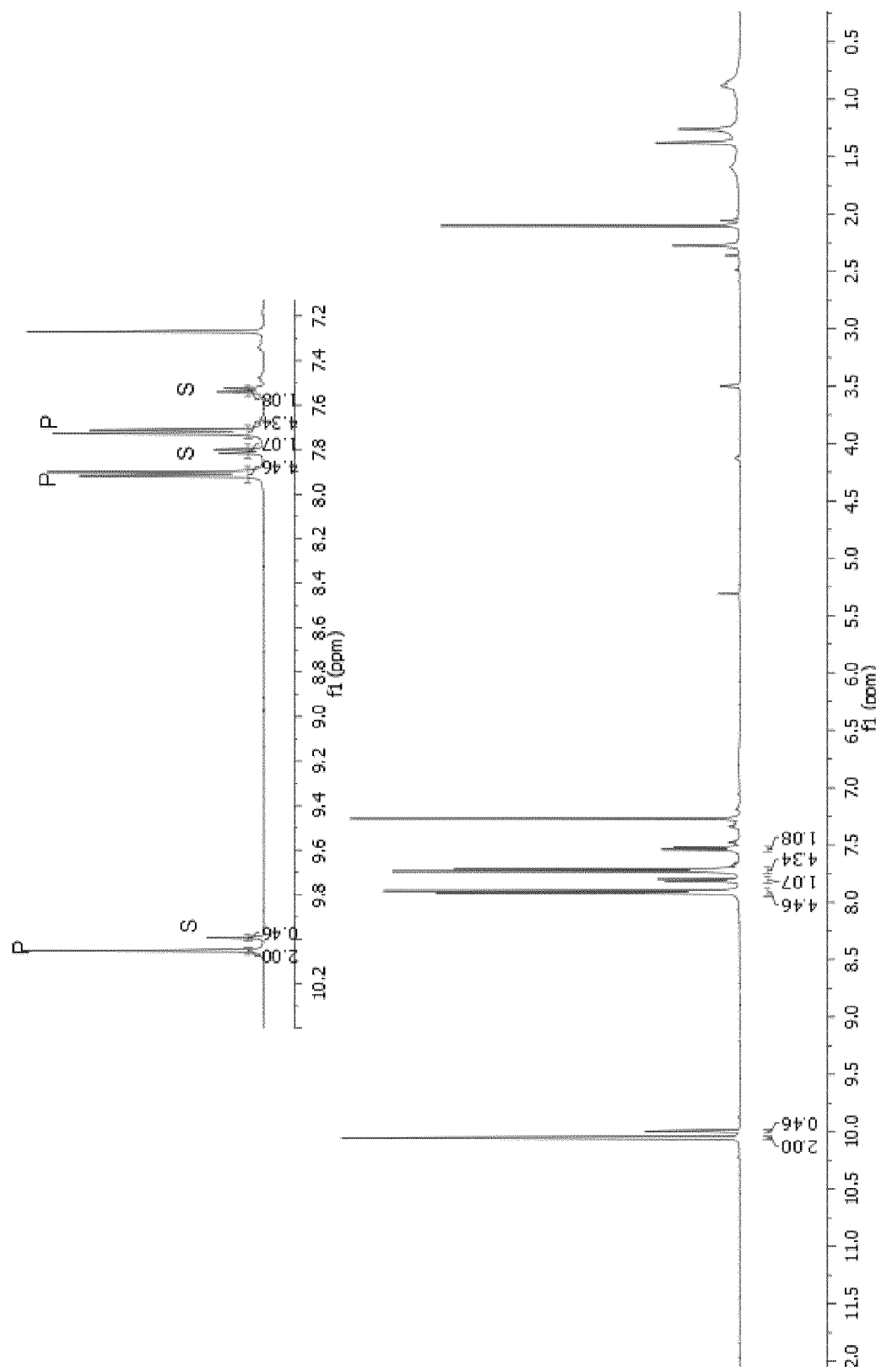
FIG. 25 illustrates the metathesis reaction of entry 3 in Table 3 in CCl$_4$ at 40° C. using 3% loading of 2. Reaction mixture after 12 h was characterized by $^1$H NMR spectroscopy; P=Product, SM=Starting material.
Figure 26:
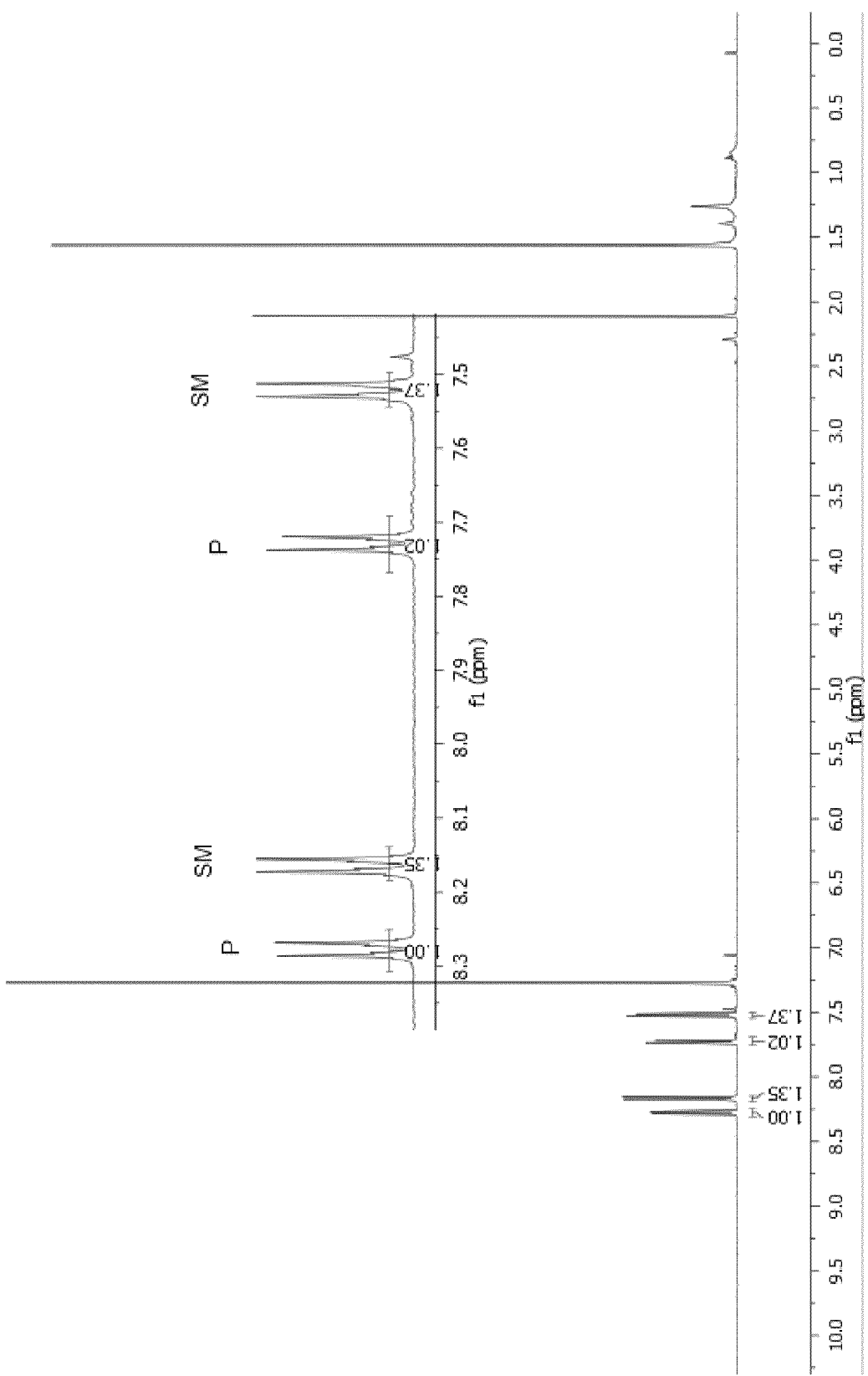
FIG. 26 illustrates the metathesis reaction of entry 4 in Table 3 in CCl$_4$ at 40° C. using 3% loading of 2. Reaction mixture after 11.5 h was characterized by $^1$H NMR spectroscopy; P=Product, SM=Starting material.
Figure 27A:
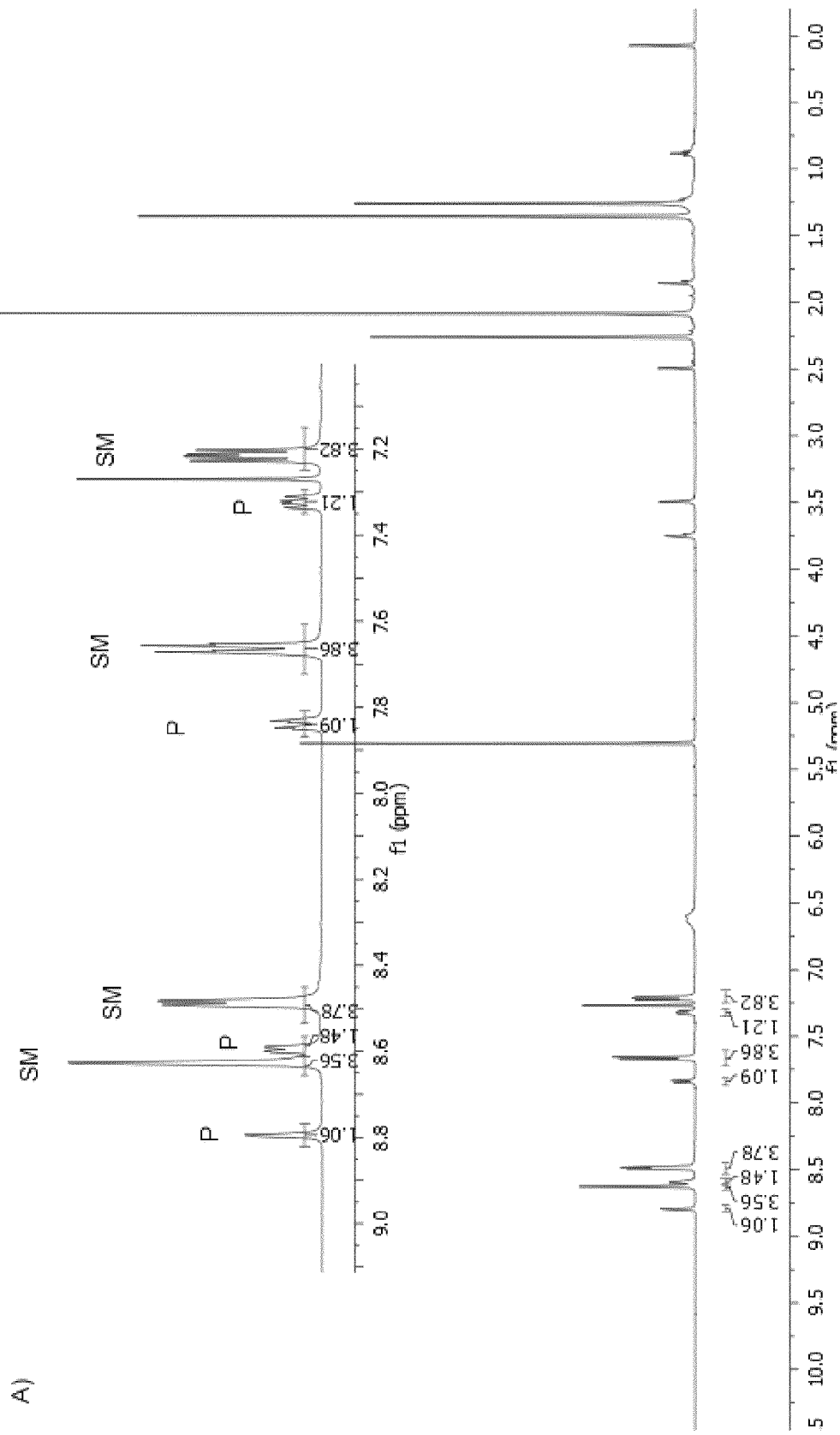
FIGS. 27A-27B, illustrates the metathesis reaction of entry 6 in Table 3 in CCl$_4$ at 40° C. using 3% loading of 2. Reaction mixture was monitored 2 h (FIG. 27A) and 13 h (FIG. 27B) by $^1$H NMR spectroscopy; P=Product, SM=Starting material.
Figure 27B:
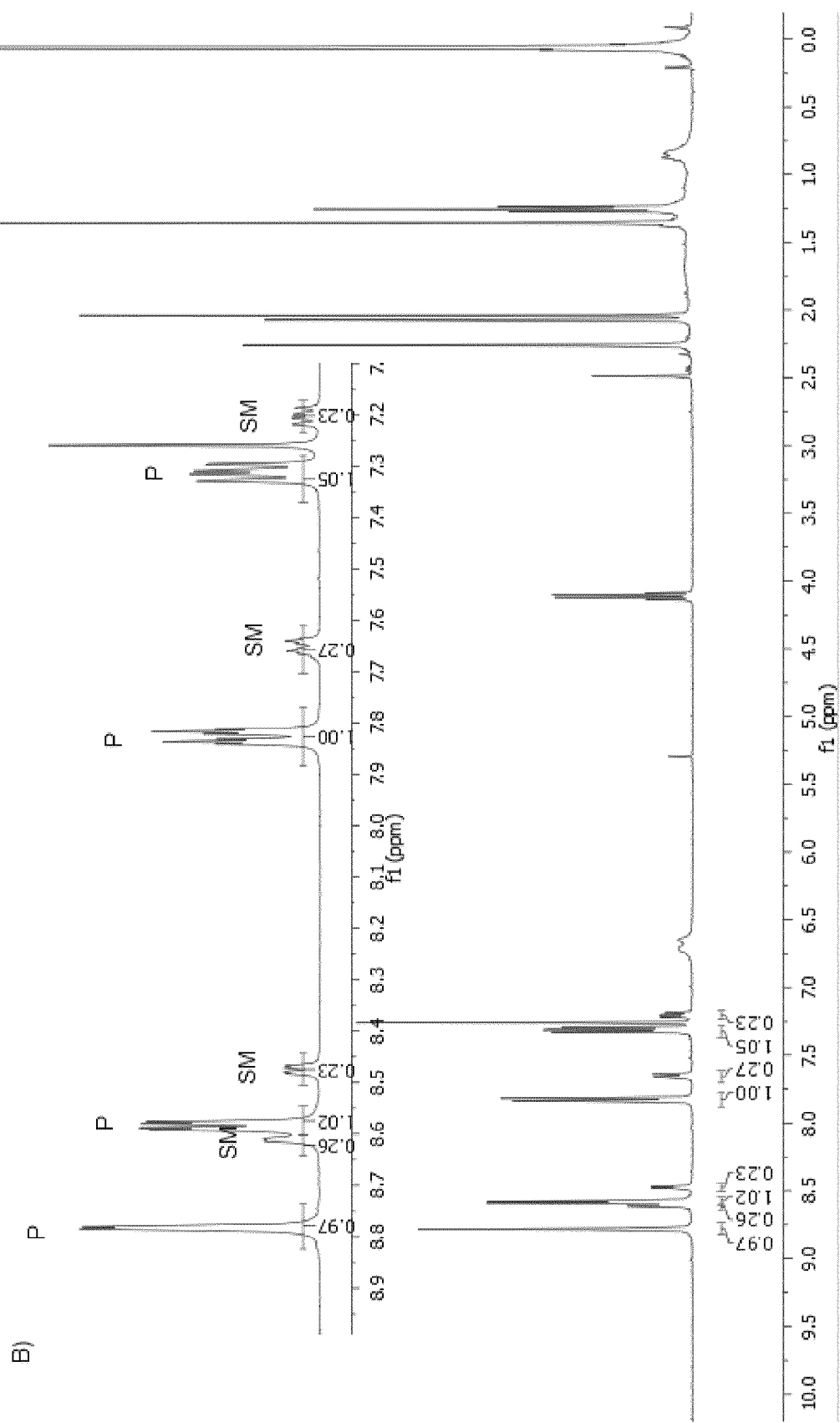
Figure 28A:
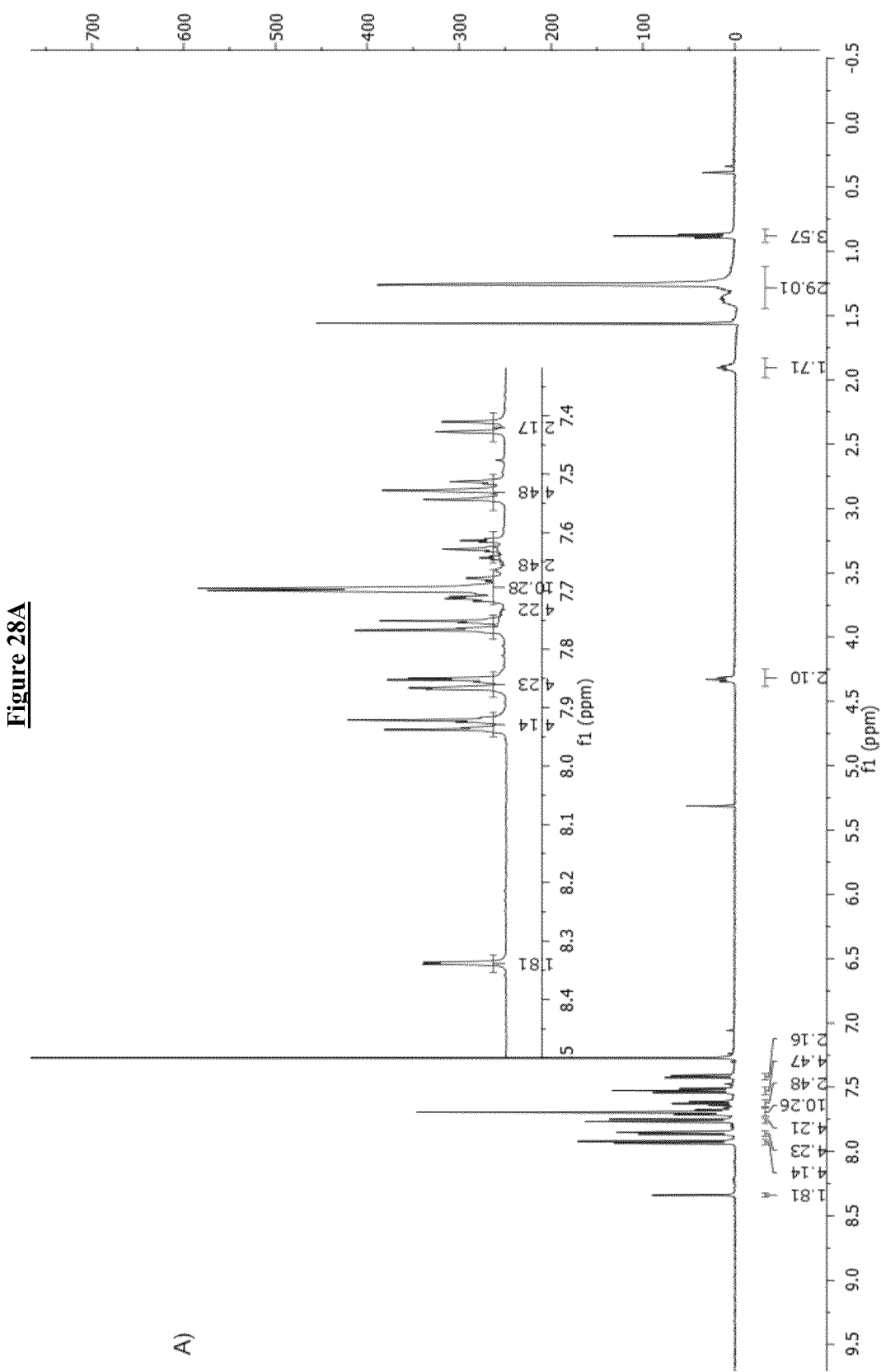
FIGS. 28A-28B, illustrates a precipitation-driven cyclooligomerization of diyne monomer for entry 8 in Table 3 in CCl$_4$ at 40° C. using 3% loading of 2. Reaction was monitored after 0 min (FIG. 28A) and 30 min (FIG. 28B) by $^1$H NMR spectroscopy.
Figure 28B:
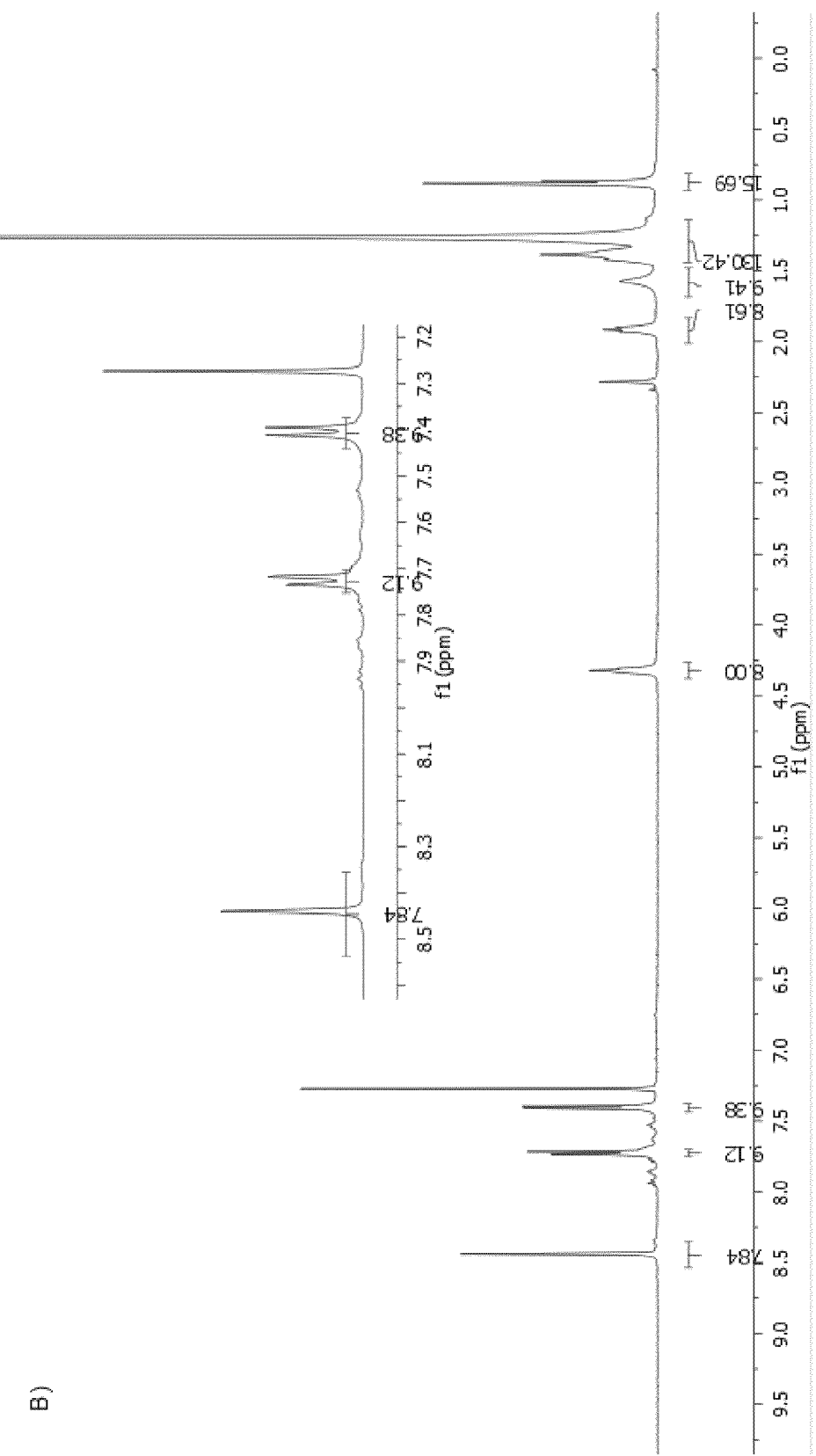
Figure 29A:
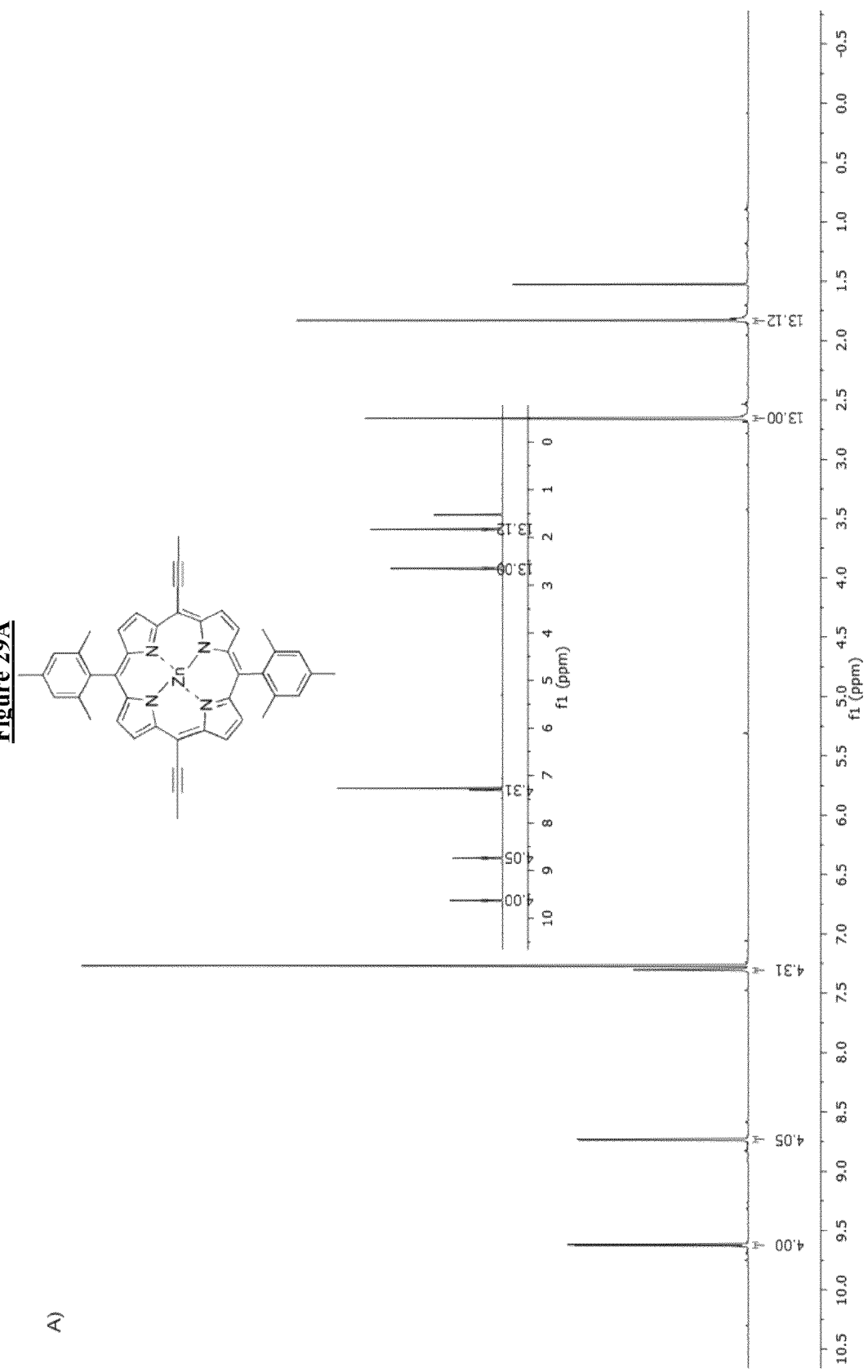
FIGS. 29A-29C, illustrates $^1$H NMR of porphyrin monomer 5 (FIG. 29A) in CDCl$_3$, monomer 6 (FIG. 29B) in CDCl$_3$, monomer 7 (FIG. 29C) in toluene-d$_a$.
Figure 29B:
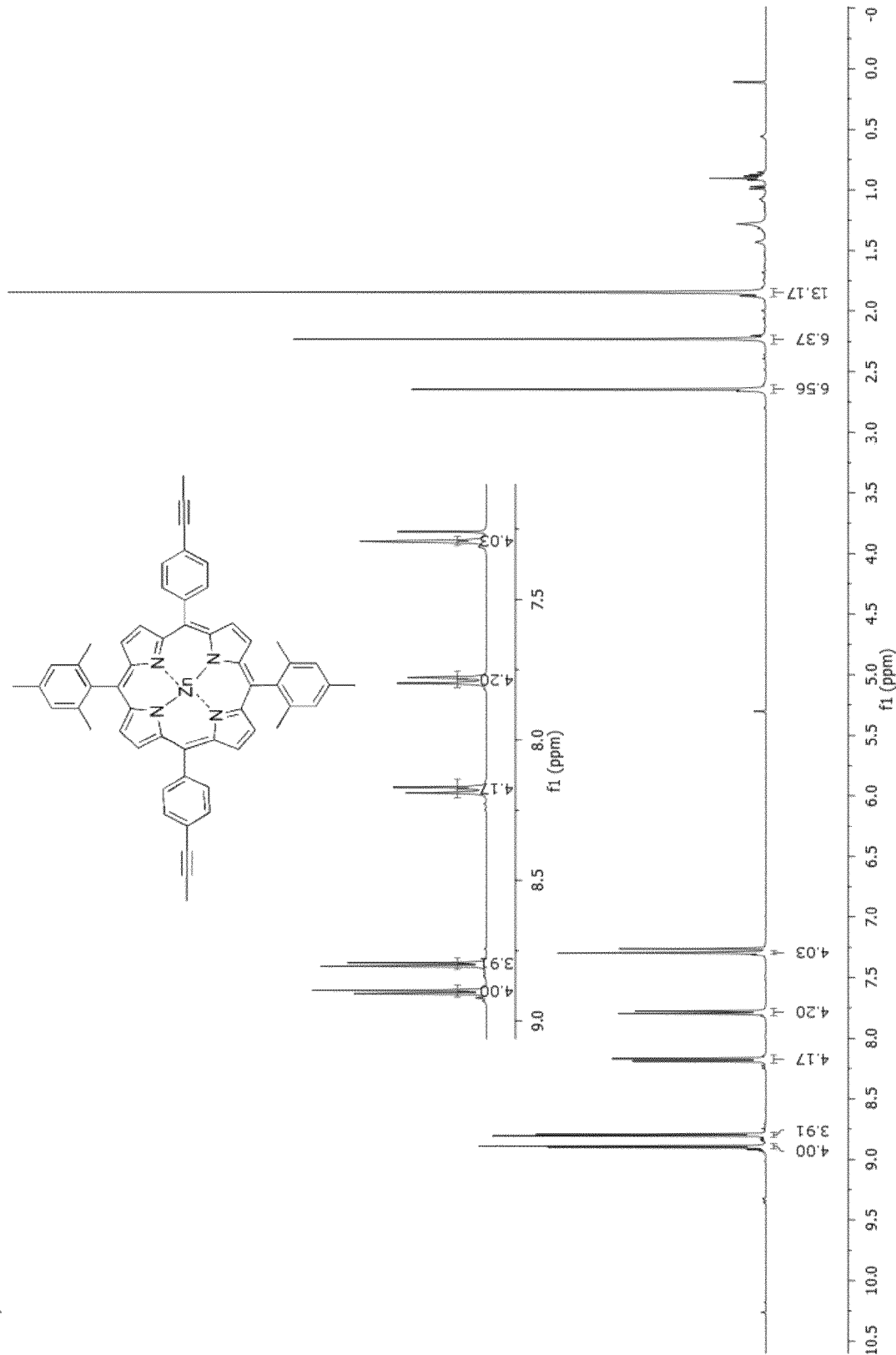
Figure 29C:
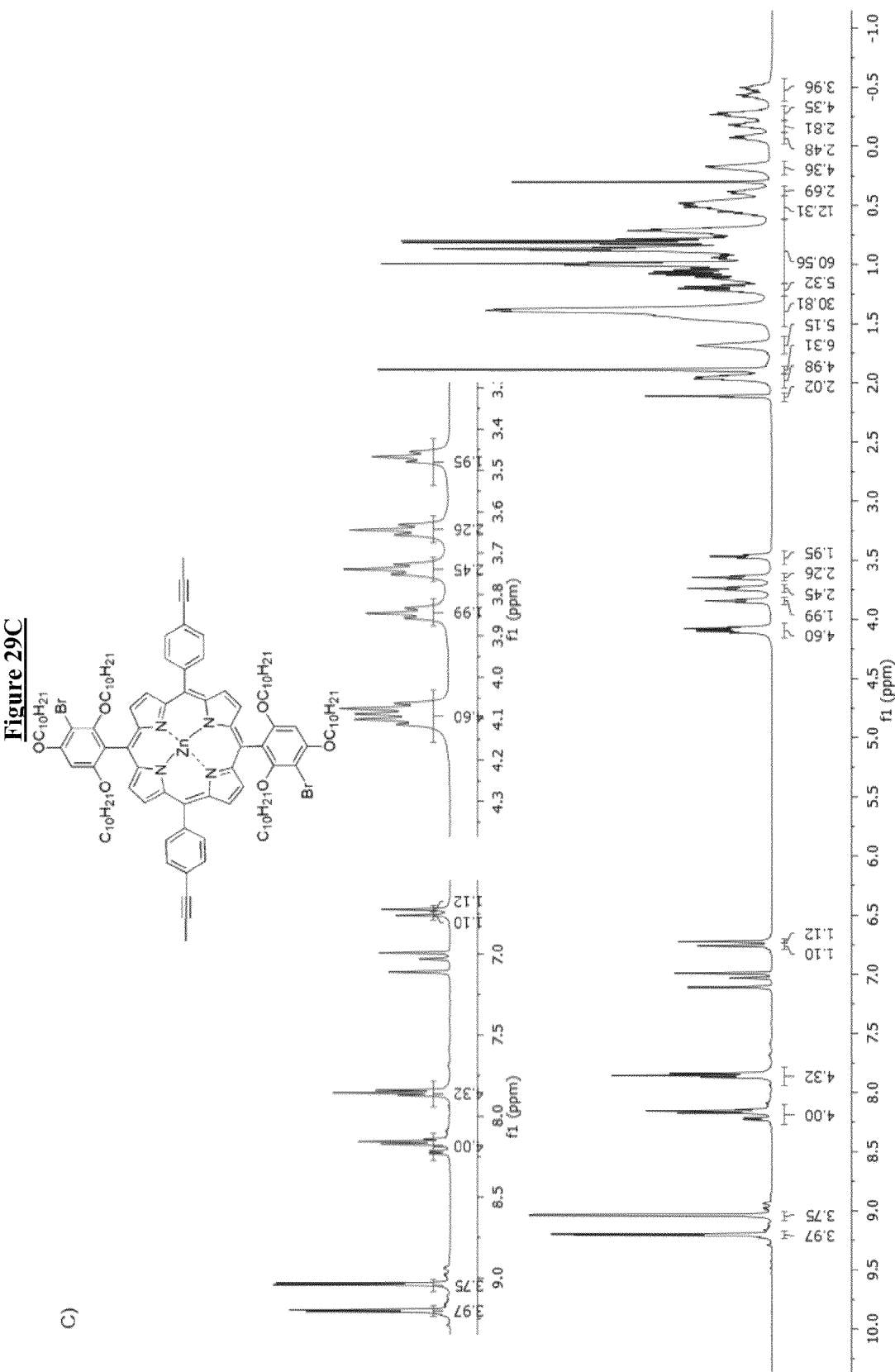
Figure 30:
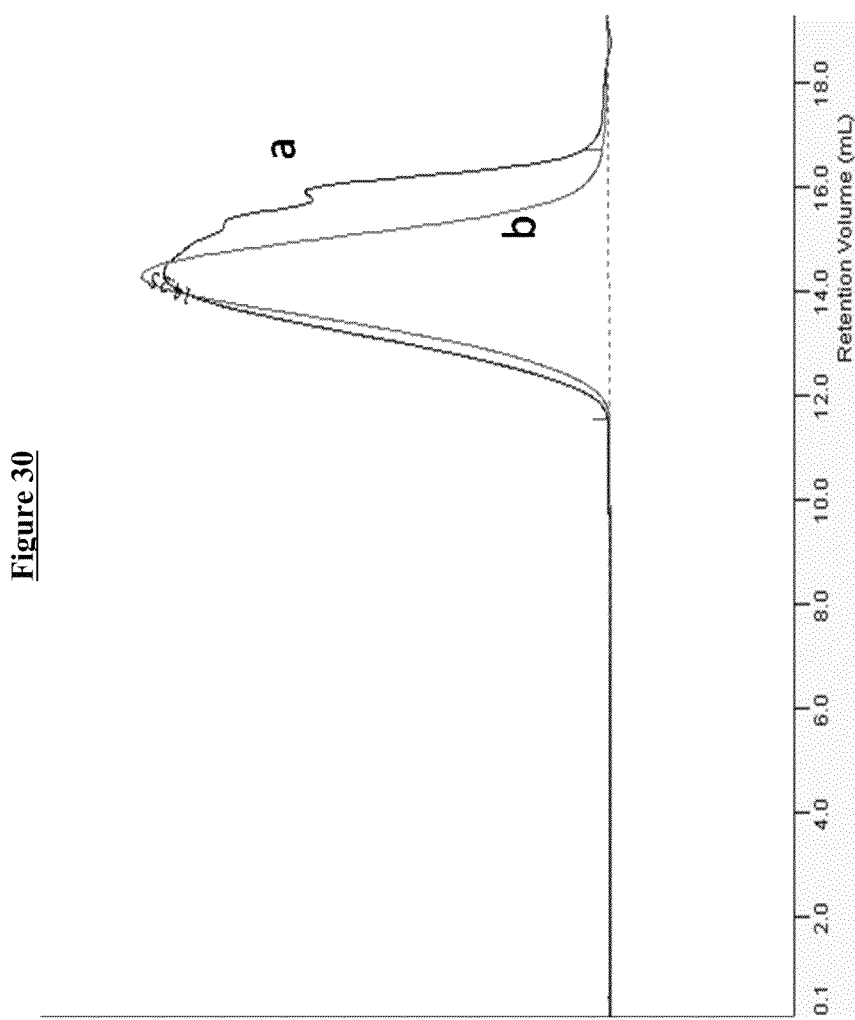
FIG. 30 illustrates gel permeation chromatography (GPC) data of the porphyrin polymer via metathesis of monomer 7 (Table 4): after one time dissolving in diethyl ether and precipitated from methanol (trace a); after 4 times dissolving in diethyl ether and precipitated from methanol (trace b).
Figure 31A:
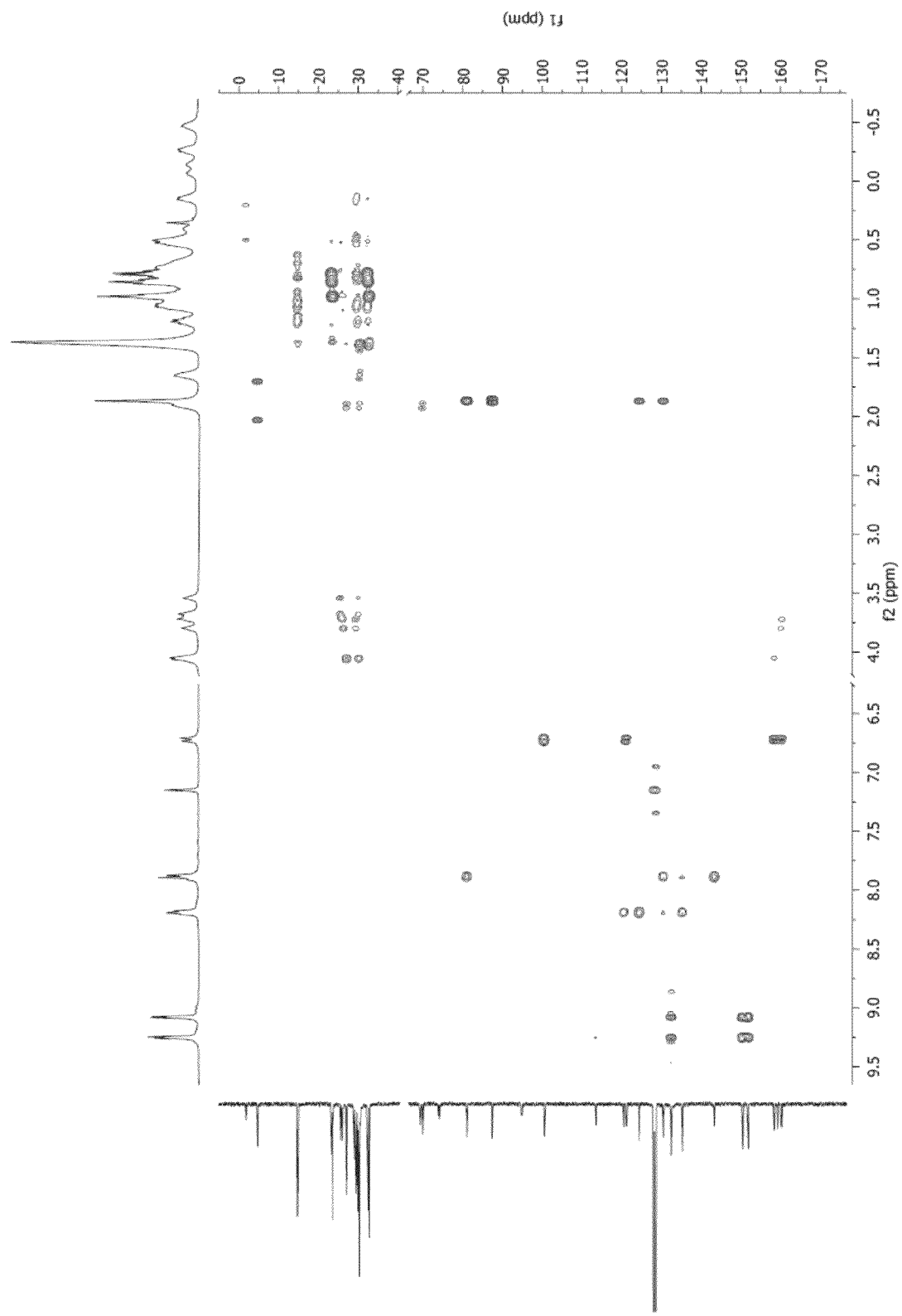
FIGS. 31A-31B, illustrates gHMBC of monomer 7 (Table 4) in C$_6$D$_6$.
Figure 31B:
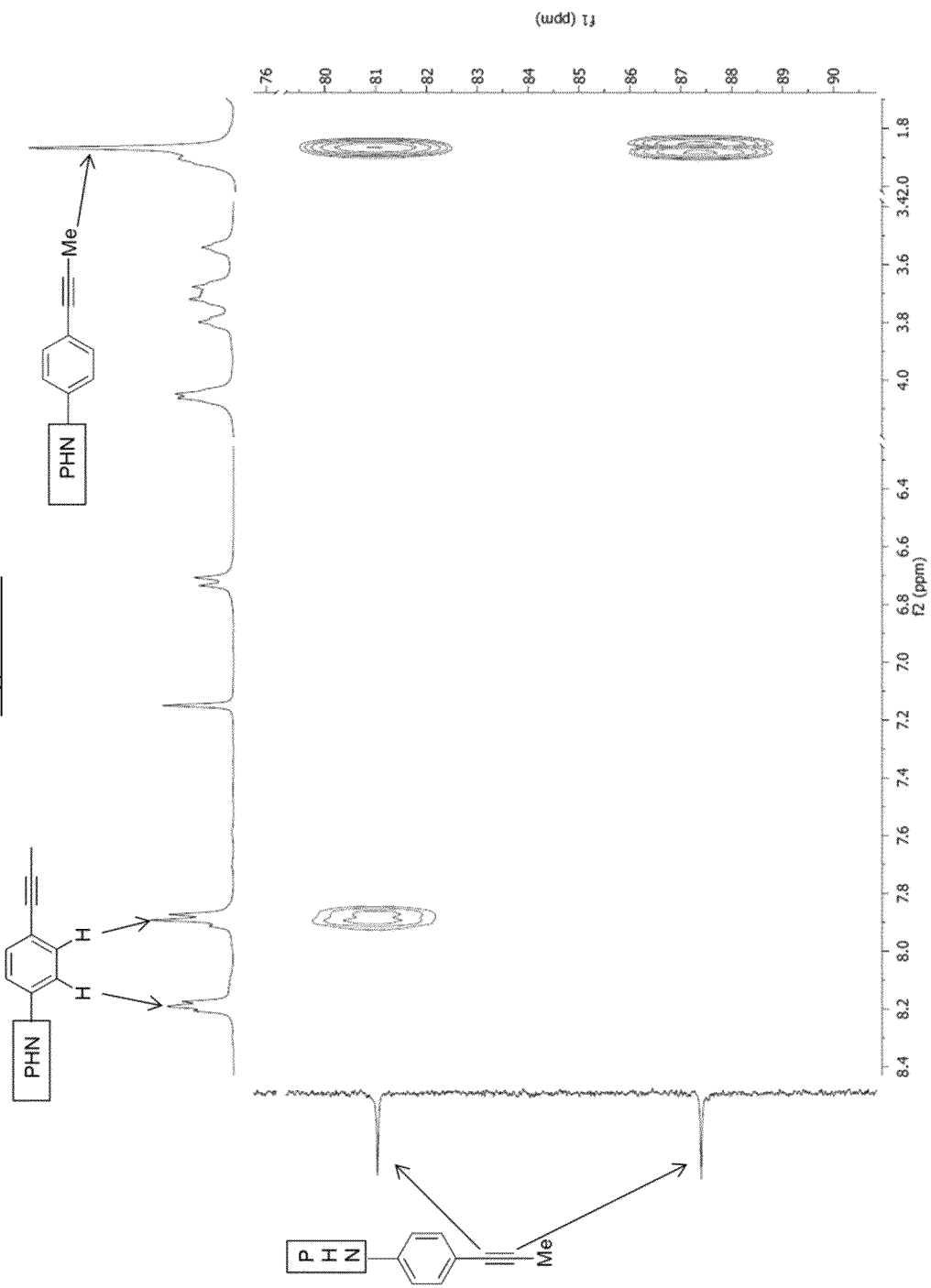
Figure 32A:
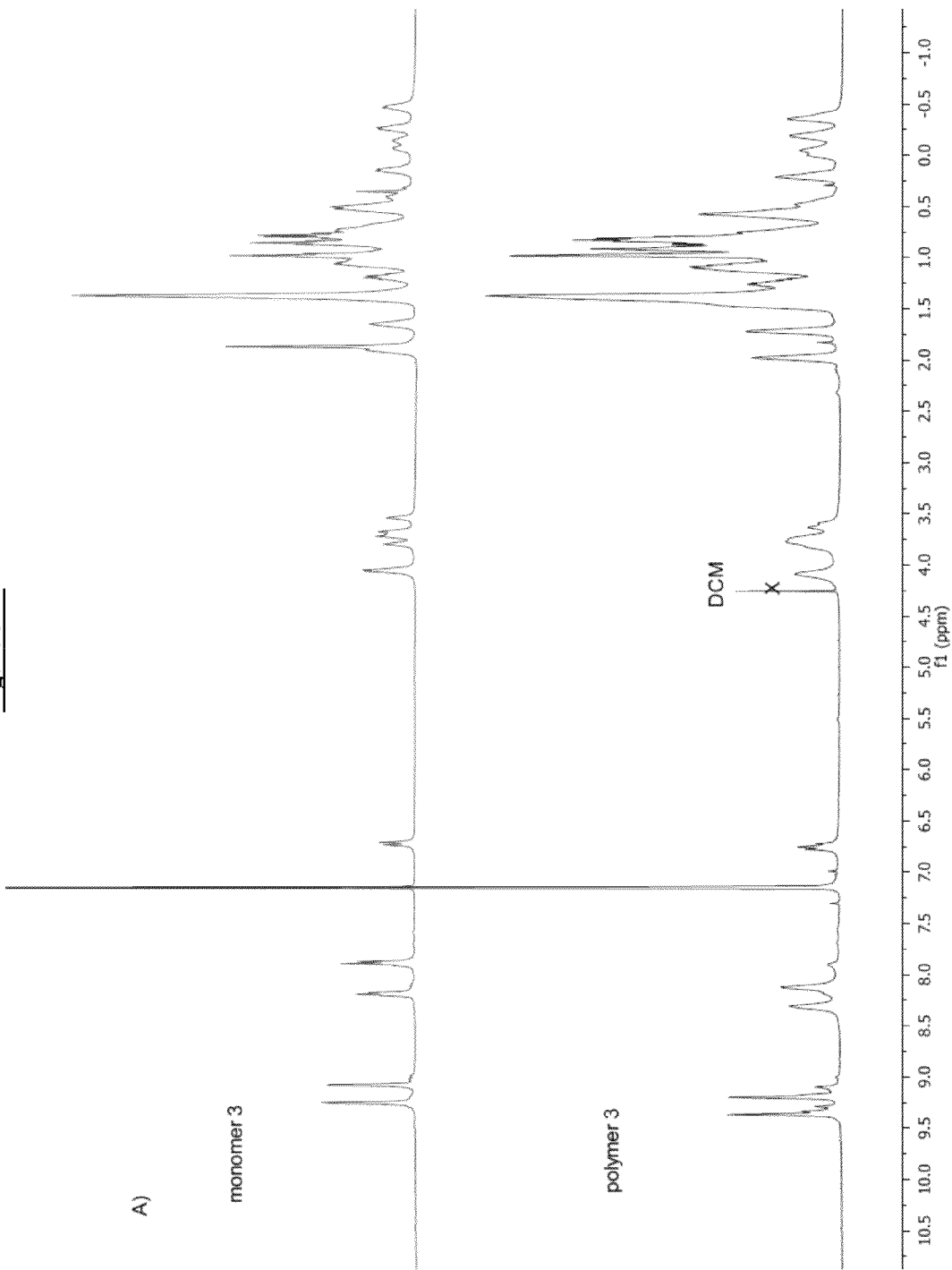
FIGS. 32A-32B, illustrates $^1$H NMR (FIG. 32A) and $^{13}$C NMR (FIG. 32B) of monomer 7 and polymer 10 in C$_6$D$_6$ (Table 4).
Figure 32B:
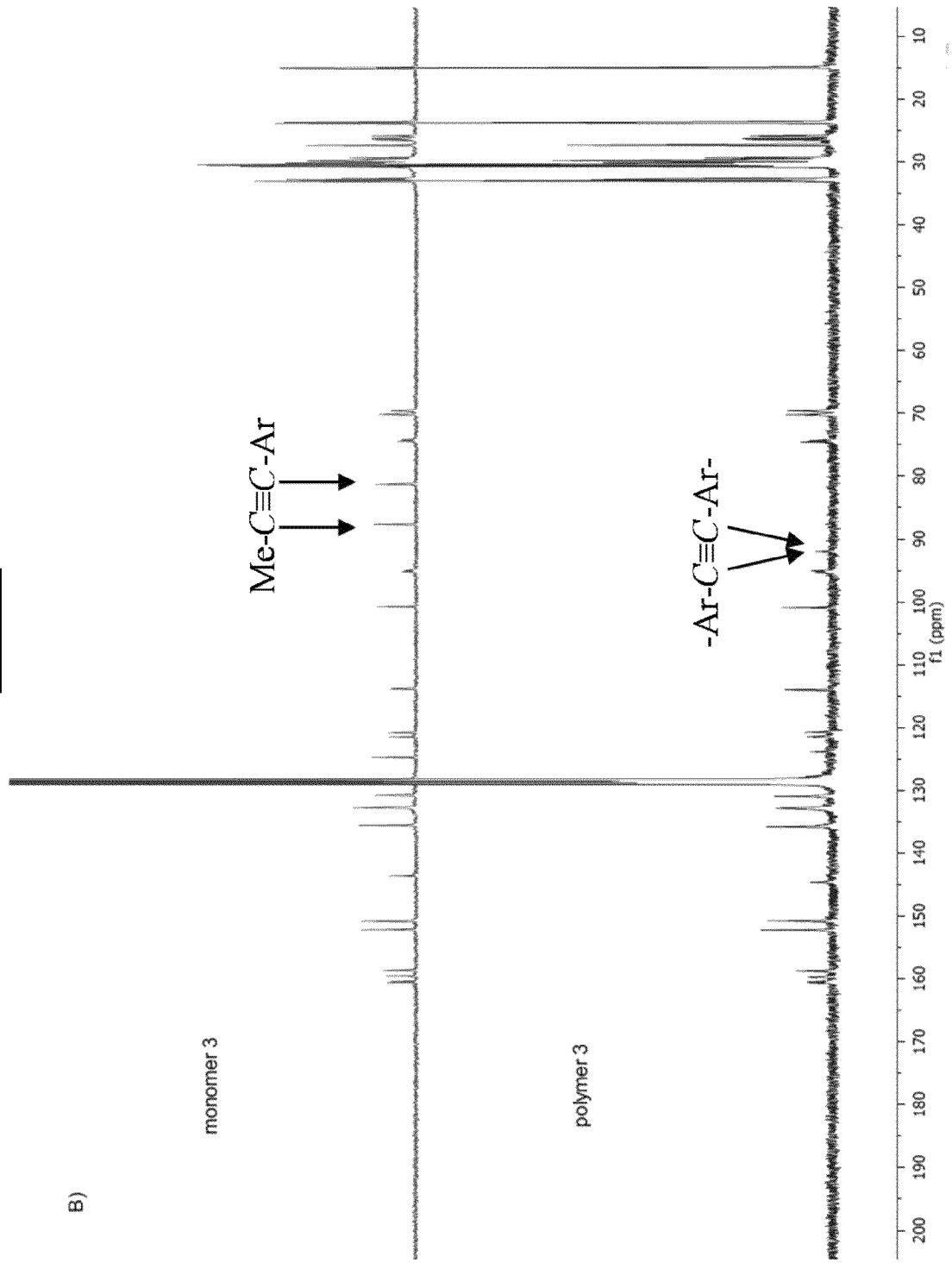
Figure 33:
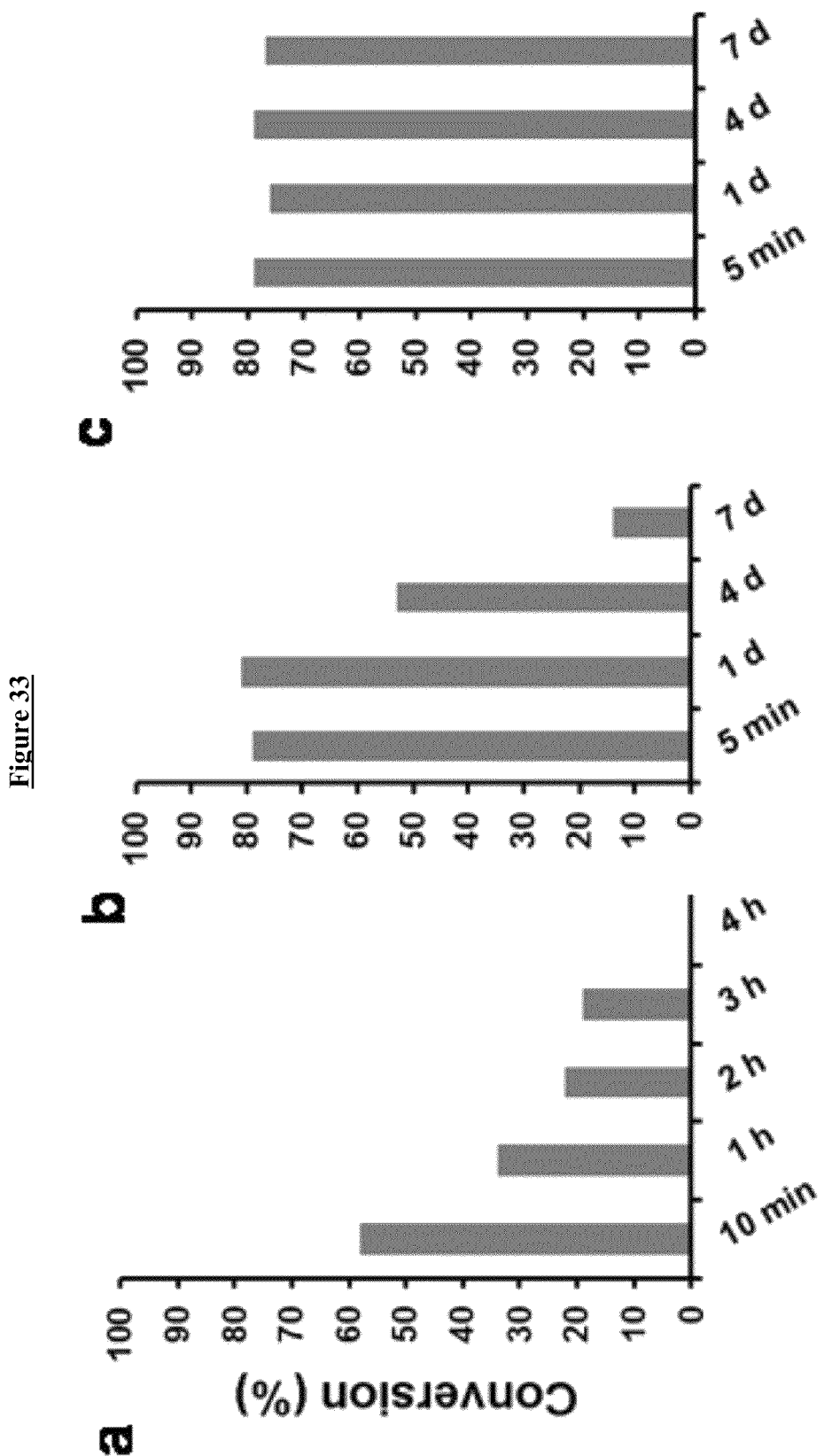
FIG. 33, comprising

The activity of catalysts 2, 3 and 4 were compared side-by-side through a kinetic study (FIG. 24) by using 4-nitropropynylbenzene as the substrate, which is one of the most challenging substrates for alkyne metathesis. Catalysts 3 and 4 gave much higher conversions, 61% and 64%, respectively, than catalyst 2 (43%) after 12.6 hours, further suggesting the importance of electrophilicity of the metal center to the catalyst activity.

The multidentate catalyst 2 also showed much higher stability than its corresponding monodentate analogue. The metathesis activity of these two catalysts at different time intervals after their in situ generation (in the absence of substrates) was compared, with 4-propynylanisole as the substrate. Catalyst 2 showed a comparable activity (<10% decrease) even after 24 hours while the catalyst generated from simple phenol ligands showed activity only within the first few hours.

Given the high metathesis activity, strong resistivity to alkyne polymerization, and functional group tolerance of these new N-quaternized multidentate Mo(VI) catalysts, the synthesis of porphyrin-based aryleneethynylene polymers (Saywell et al., 2010, Angew. Chem. 122:9322; 2010, Angew. Chem. Int. Ed. 49:9136; Huang et al., 2008, Macromolecules 41:6895; Iyoda & Yamakawa, 2011, Angew. Chem. 123:10708; 2011, Angew. Chem. Int. Ed. 50:2; Anderson, 1999, Chem. Commun. 2323; Jiang et al., 1997, Chem. Mater. 9:2031; Anderson et al., 1994, Angew. Chem. 106:711; 1994, Angew. Chem. Int. Ed. 33:655; Takeuchi et al., 2006, Angew. Chem. 118:5620; 2005, Angew. Chem. Int. Ed. 45:5494) was performed. The ethynylene bridged porphyrin polymers were good candidates for molecular electronics due to their high efficiency for transporting charge over long distances (Lin et al., 1994, Science 264:1105; Susumu et al., 2006, J. Am. Chem. Soc. 128:8380; Susumu & Thelien, 2002, J. Am. Chem. Soc. 124:8550; Winters et al., 2007, J. Am. Chem. Soc. 129:4291; Grozema et al., 2007, J. Am. Chem. Soc. 129:13370). To date, most literature reports utilizing palladium catalyzed cross coupling for the polymer synthesis. However, common side reaction in poly(aryleneethynylene) (PAE) synthesis via cross-coupling approach is the formation of butadiyne defect sites in the growing polymer chain when two terminal acetylenes are coupled (Martin & Buchwald, 2008, Acc. Chem. Res. 41:1461; Nielson et al., 2005, Macromolecules 38:1180). In this context, alkyne metathesis offers a very efficient and defect-free synthesis of ethynylene bridged polymers (Bunz, 2001, Acc. Chem. Res. 34:998).

Figure 16:
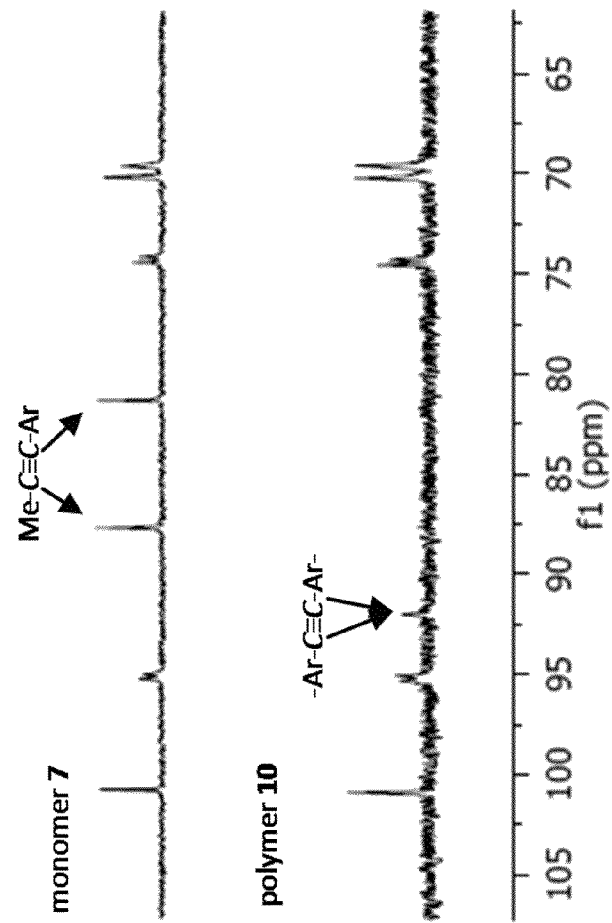
FIG. 16 illustrates the $^{13}C$ NMR spectrum in $C_6D_6$ of monomer 7 and polymer 10.
Figure 17A:
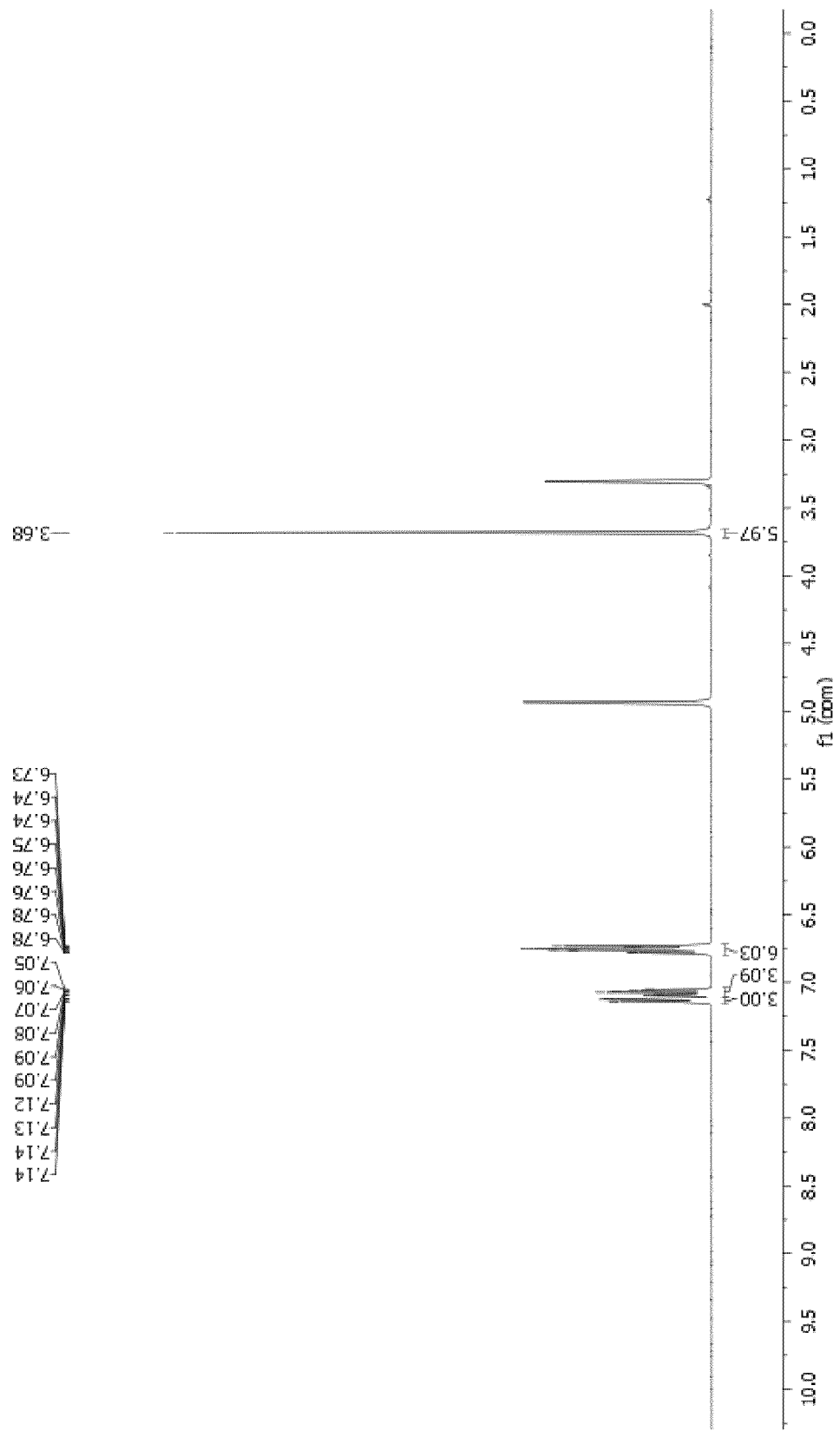
FIGS. 17A-17B, illustrates the $^1H$ NMR spectra ($CD_3OD$, 500 MHz, FIG. 17A) and $^{13}C$ NMR spectra ($CD_3OD$, 100 MHz, FIG. 17B) of the ligand L5.
Figure 17B:
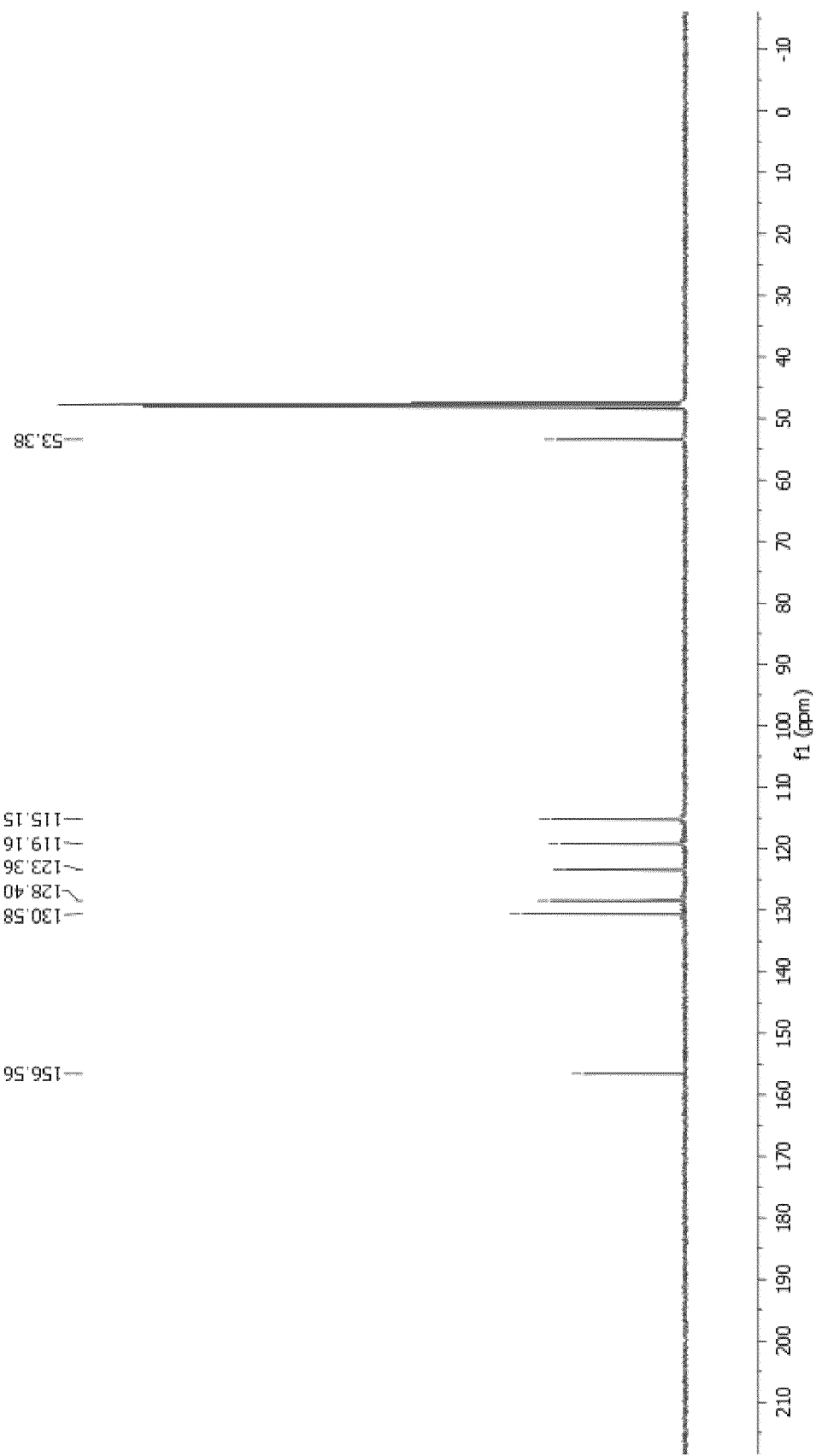
Figure 18B:
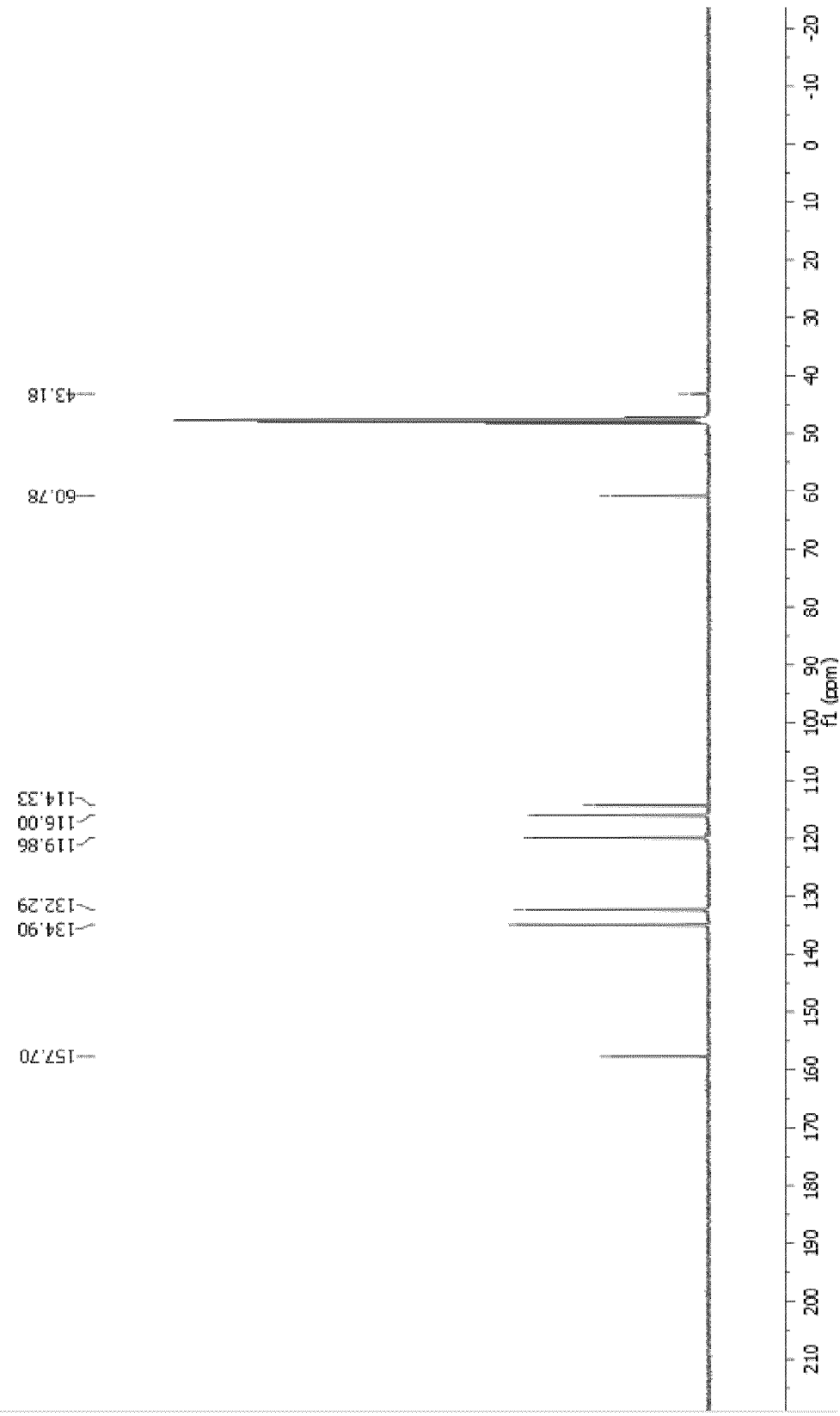
Figure 19A:
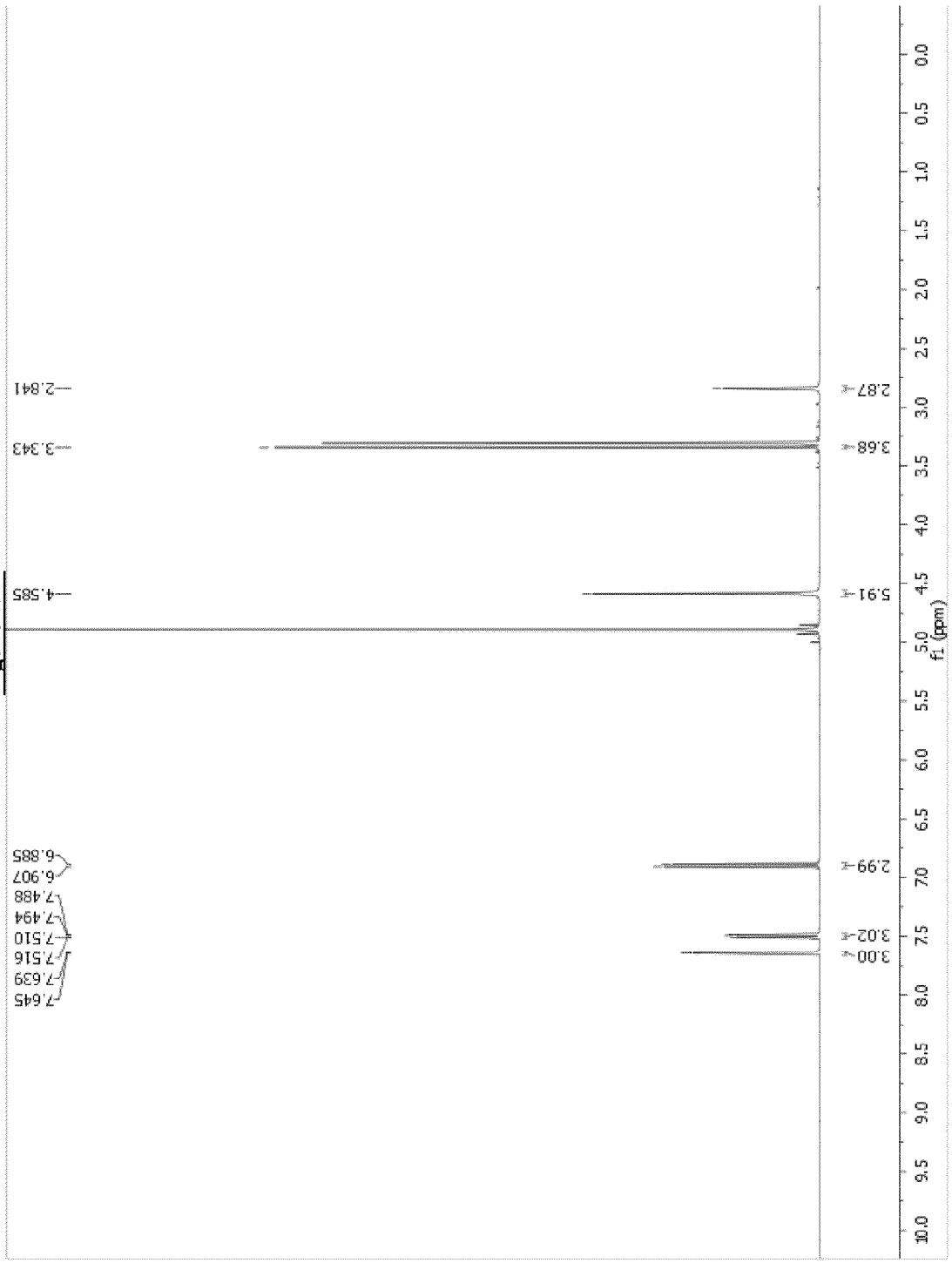
FIGS. 19A-19B, illustrates the $^1H$ NMR spectra ($CD_3OD$, 500 MHz, FIG. 19A) and $^{13}C$ NMR spectra ($CD_3OD$, 100 MHz, FIG. 19B) of the ligand L3.
Figure 19B:
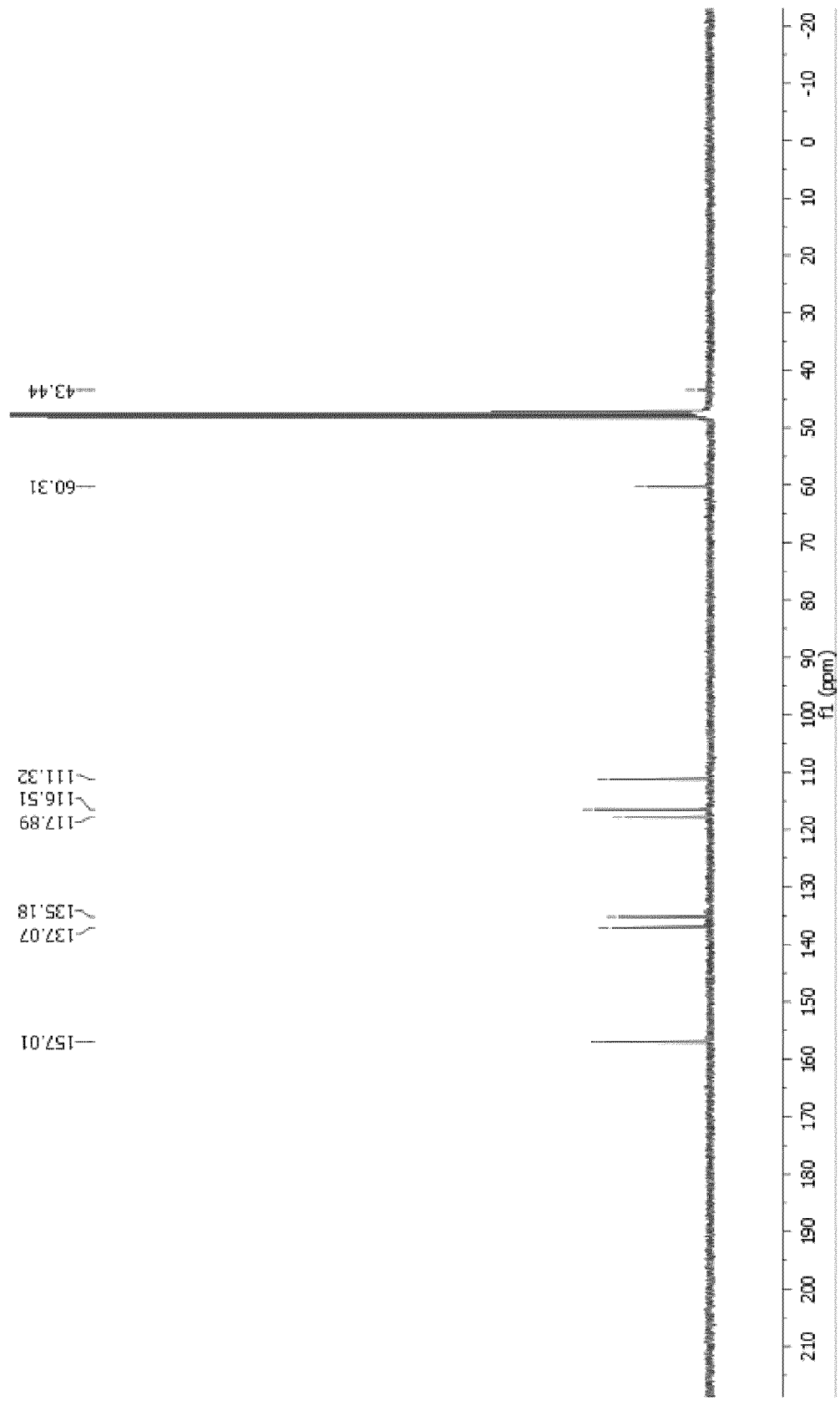
Figure 20A:
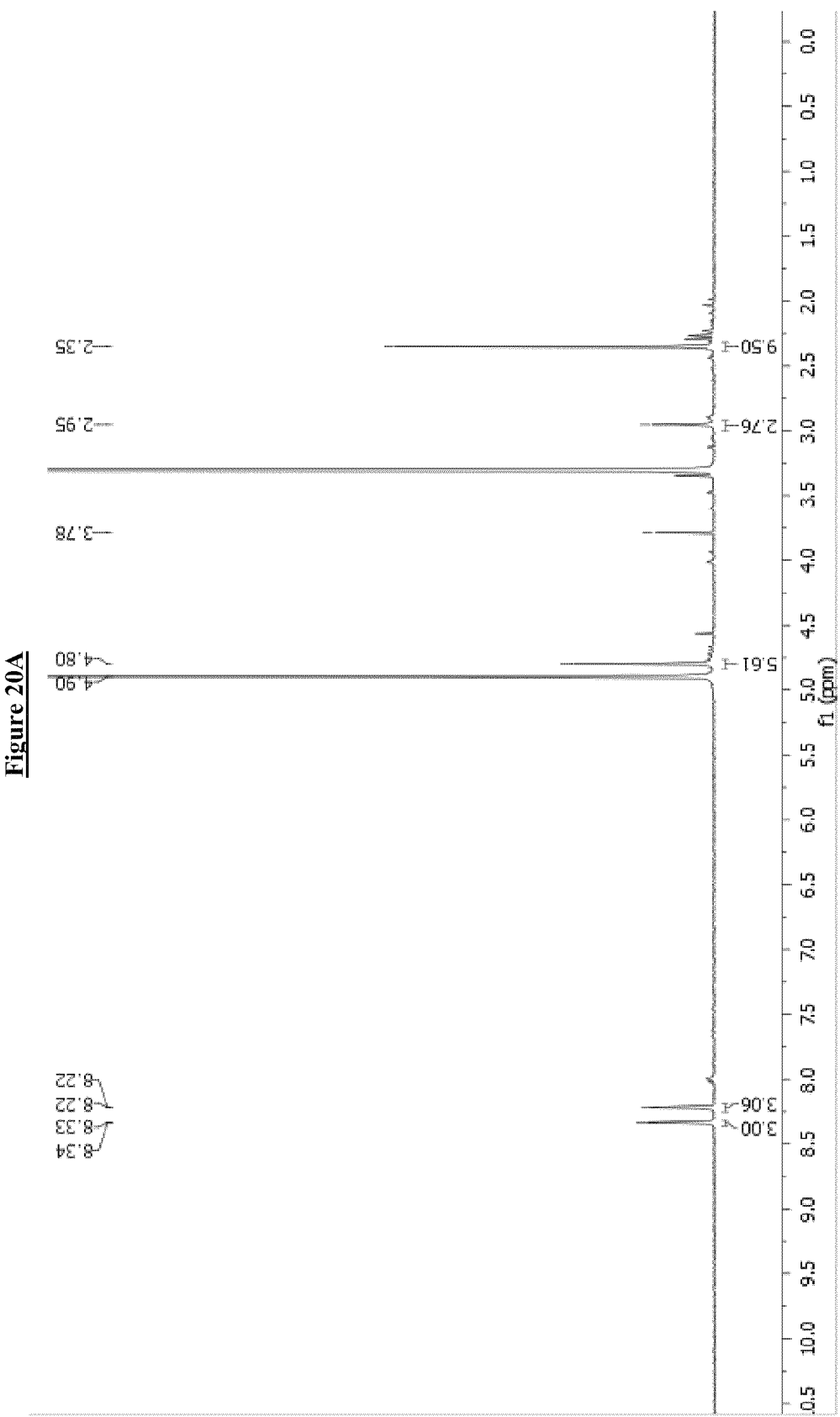
FIGS. 20A-20B, illustrates the $^1H$ NMR spectra ($CD_3OD$, 500 MHz, FIG. 20A) and $^{13}C$ NMR spectra ($CD_3OD$, 100 MHz, FIG. 20B) of the ligand L4.
Figure 20B:
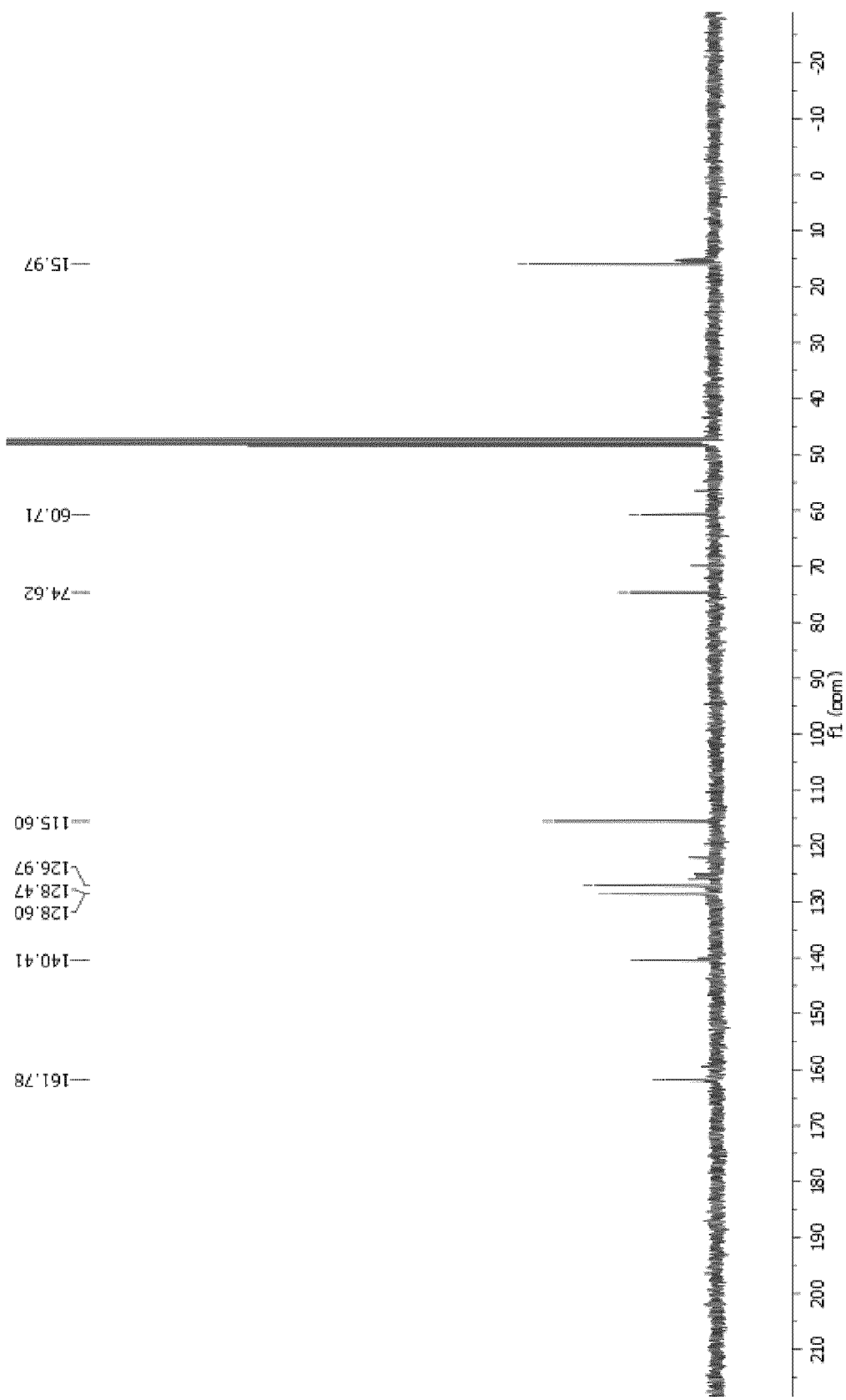
Figure 21A:
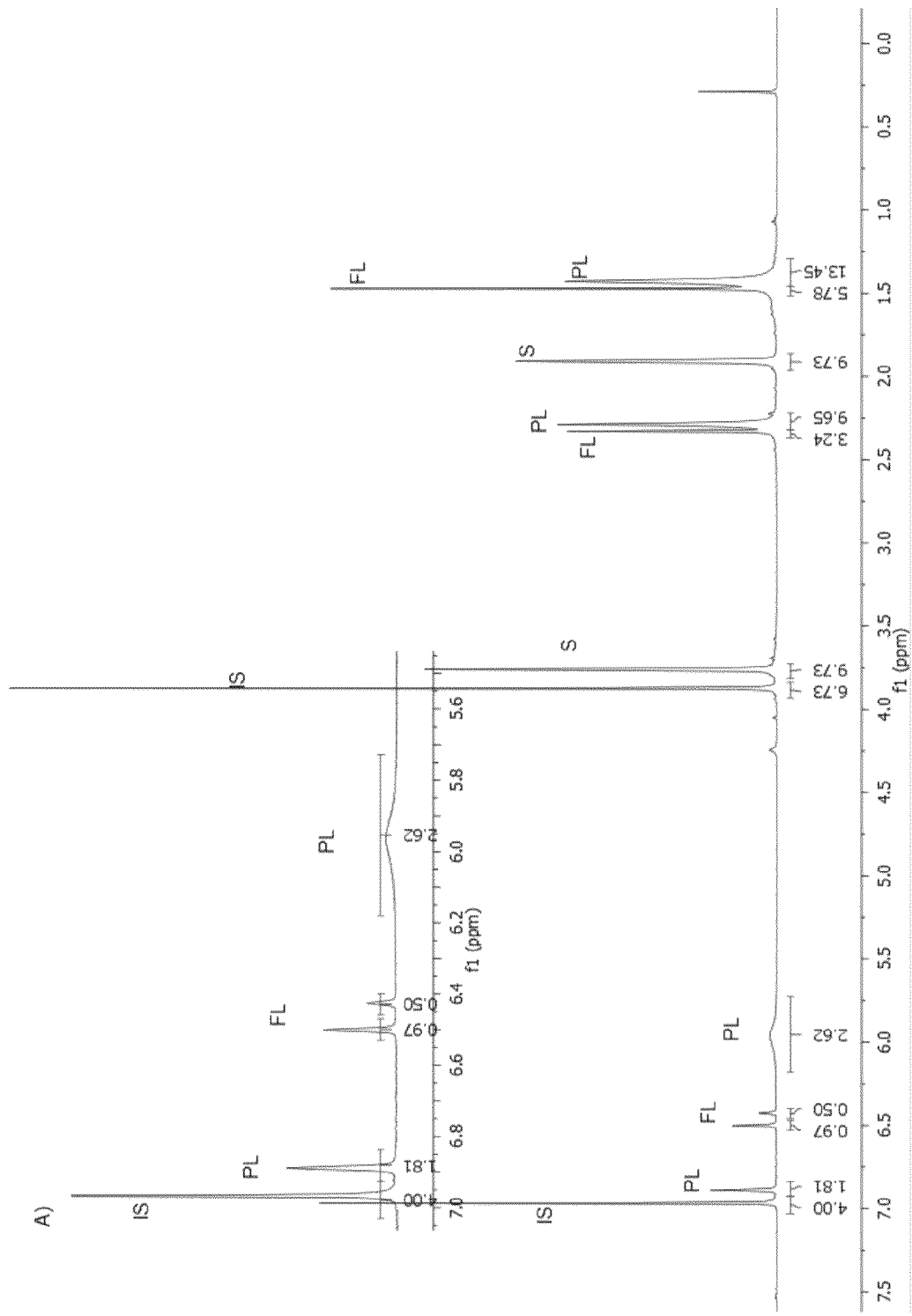
FIGS. 21A-21D, illustrates $^1H$ NMR experiment in THF-$d_8$ showing the displacement of the amide ligands in the Mo(VI) propylidyne precursor with L5 and L3.
Figure 21B:
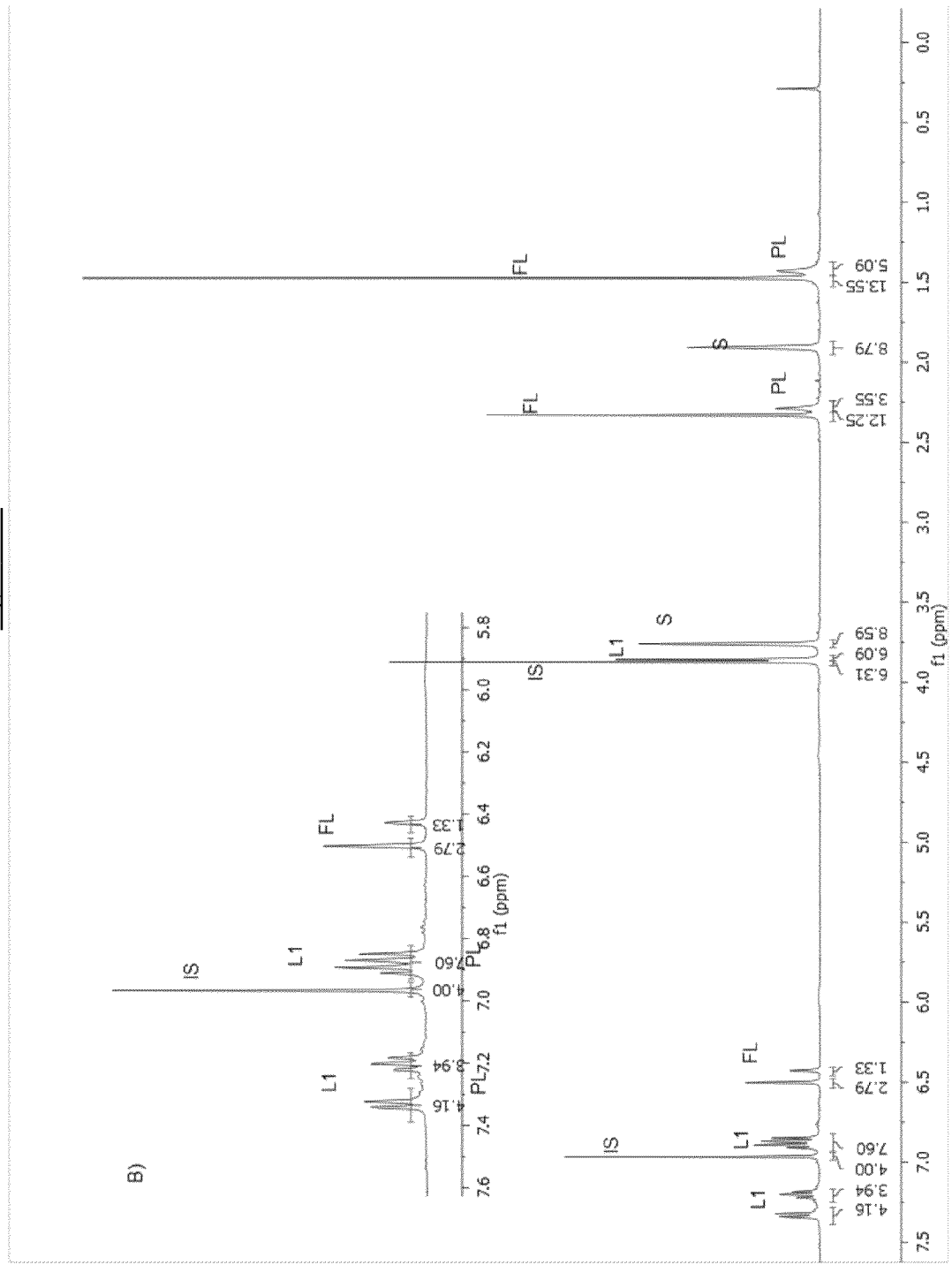
Figure 21C:
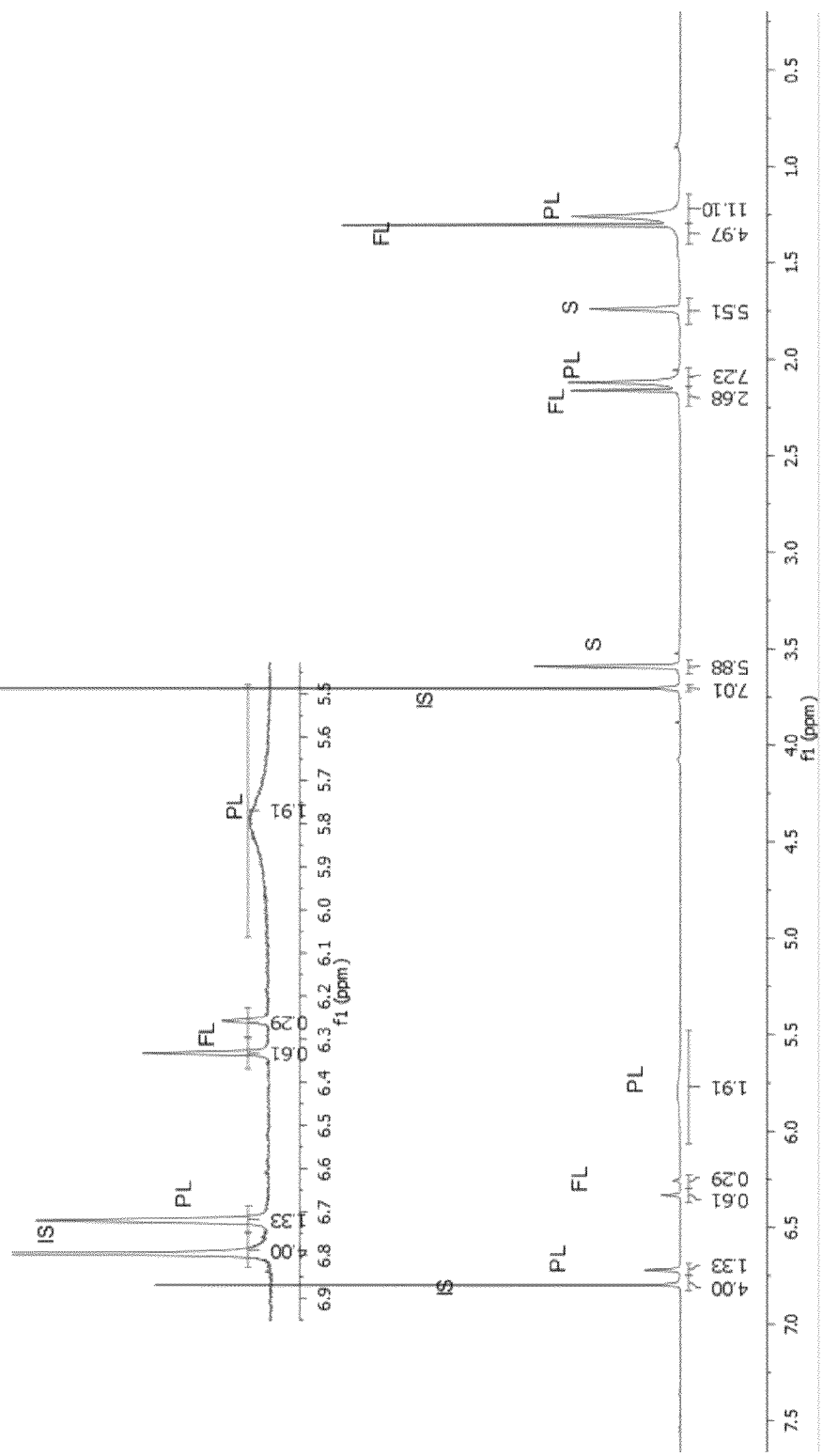
Figure 21D:
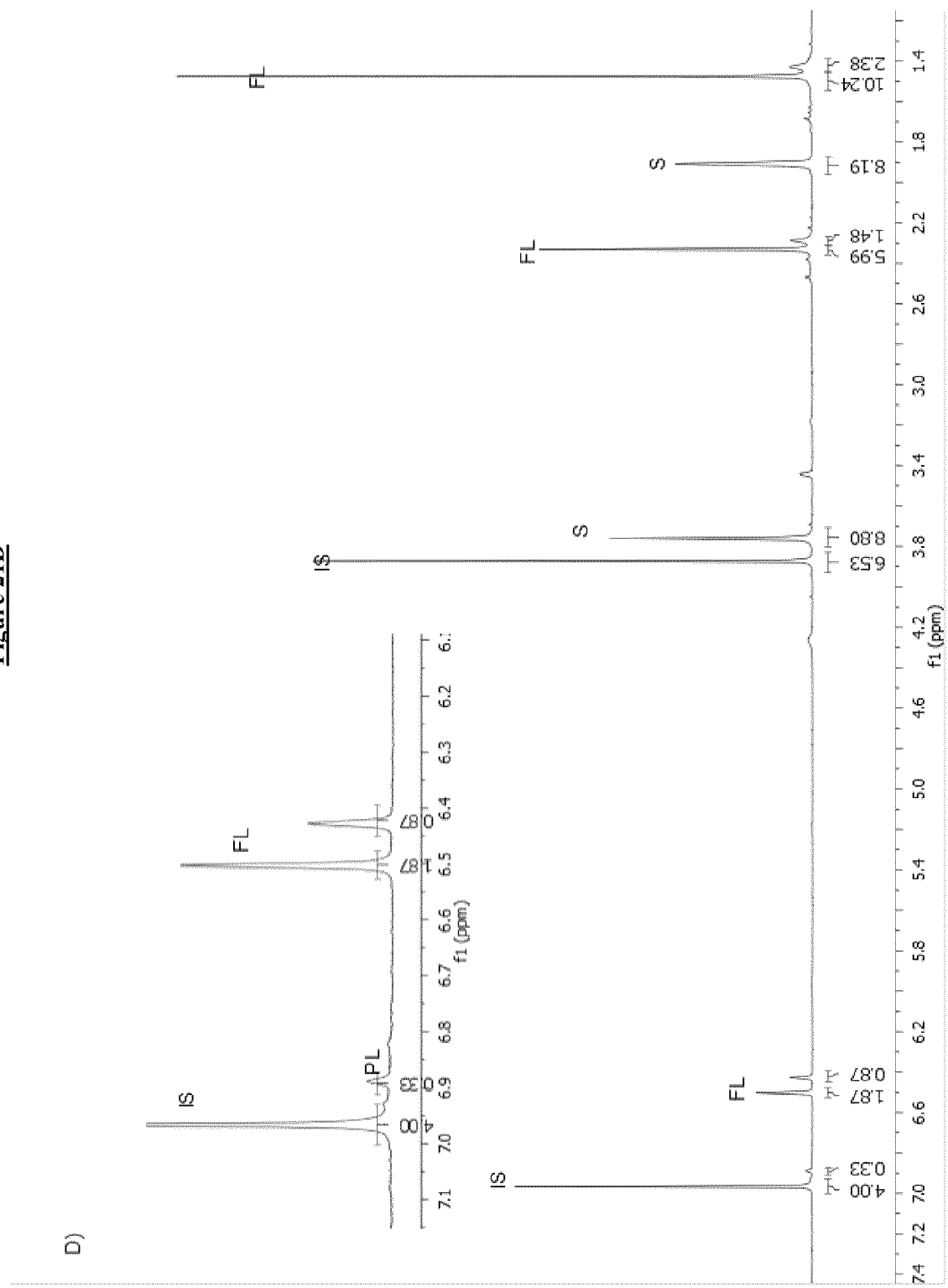

As a proof-of-concept, different porphyrin monomers (5-7) were prepared and subjected to alkyne metathesis (Table 4). For the metathesis of 5, relatively low conversion was observed even under high temperature (70° C.), presumably due to lower electron density of the propynes directly connected to the porphyrin backbone. In metathesis of monomer 6, only short oligomers of <5 repeating units were observed in the soluble fraction, and most of the reaction mixtures precipitated out during the reaction, due to their insufficient solubility. In great contrast, when monomer 7 that contains six long solubilizing chains was used, the solution stayed homogeneous and the porphyrin polymer (8) with high molecular weight (Mn=12,100, PDI=1.50, Table 4, entry 3) was obtained. The $^{13}C$ NMR spectrum showed only a single type of alkyne signal (FIG. 16) that corresponds to the carbons in the ethynylene repeating units, thus supporting the defect-free structure of the porphyrin polymer. This result opens new possibilities for the synthesis and study of porphyrin-based aryleneethynylene polymers.

In one embodiment, the compound of formula (IV) is one of the following catalytic complexes:

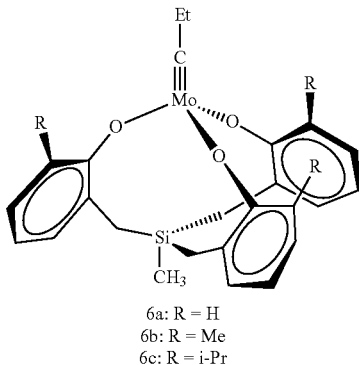

6a: R = H
6b: R = Me
6c: R = i-Pr

Multidentate catalysts (6a-6c) may be prepared from triphenolsilane ligands (L7a-L7c, Scheme 8), which are readily accessible and compatible with various substrates. As described herein, the catalysts remained active in solution phase for days at room temperature (months at −30° C.) and

TABLE 4

Mo (VI) catalyzed metathesis of porphyrin substrates

| Entry | Substrate | Product | Yield (%) |
|---|---|---|---|
| 1) | monomer 5<br>R1 = 3,5-dimethyl-4-methylphenyl (H3C, H3C, CH3)<br>R2 = —C≡C—CH3 | R2—(PHN with R1, R1)—C≡C—CH3, n=1-5 | 40 |
| 2) | monomer 6<br>R1 = 3,5-dimethyl-4-methylphenyl (H3C, H3C, CH3)<br>R2 = —C6H4—C≡C—CH3 | H3C—C≡C—(C6H4—PHN(R1,R1)—C6H4—C≡C)n=1-5—CH3 | 90 |
| 3) | monomer 7<br>R1 = 3,5-bis(decyloxy)-4-decyloxyphenyl (C10H21O, C10H21O, OC10H21)<br>R2 = —C6H4—C≡C—CH3 | H3C—C≡C—(C6H4—PHN(R1,R1)—C6H4—C≡C)n—CH3<br>8 | 63 |

Reaction conditions: 40° C., CCl4, 5 mol % catalyst loading, 4-18 h, in closed system, with the reaction solution exposed to vacuum for 6-8 times to remove the metathesis byproduct 2-butyne enabled the metathesis of challenging phenol-based substrates in good yield. A gram-scale preparation of a phenyleneethynylene macrocycle was also accomplished starting from simple dipropynyl-substituted monomers in a closed system.

Figure 34A:
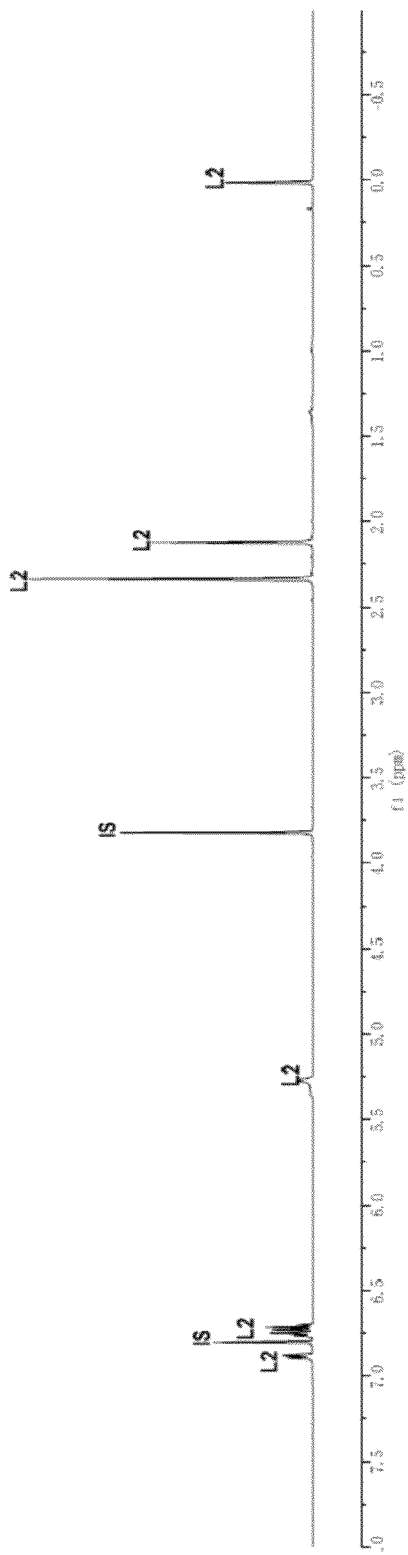
FIGS. 34A-34C, is a series of spectra illustrating $^1$H NMR experiment in CCl$_4$. The spectra show the displacement of the ligands on the Mo-precursor complex with L7b.
Figure 34B:
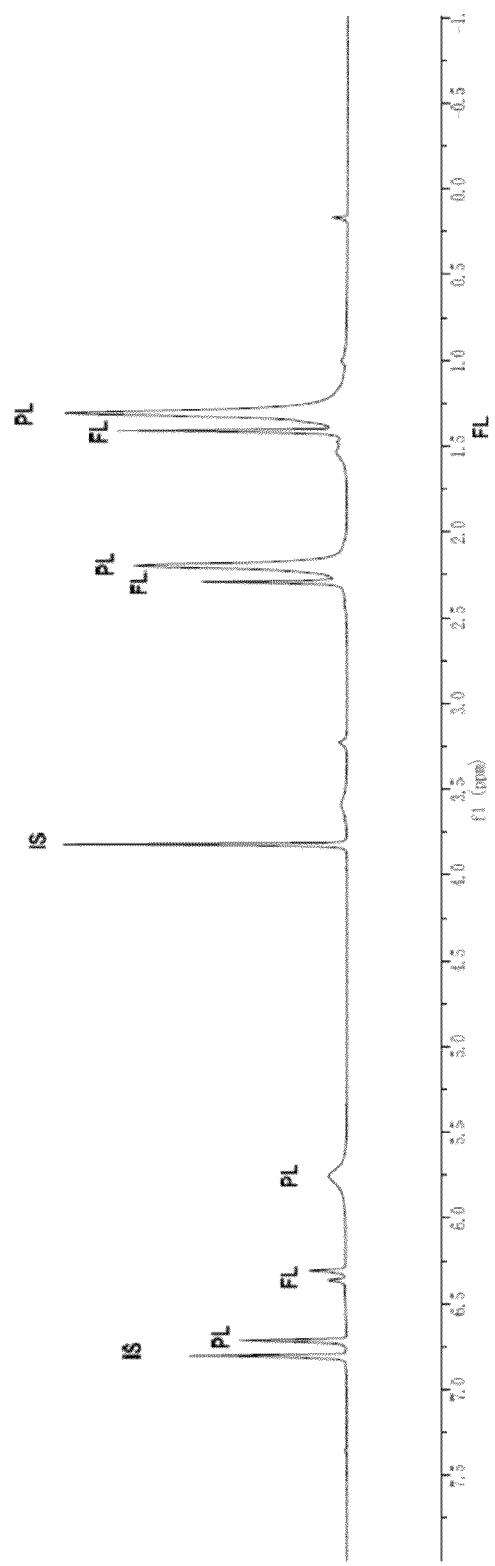
Figure 34C:
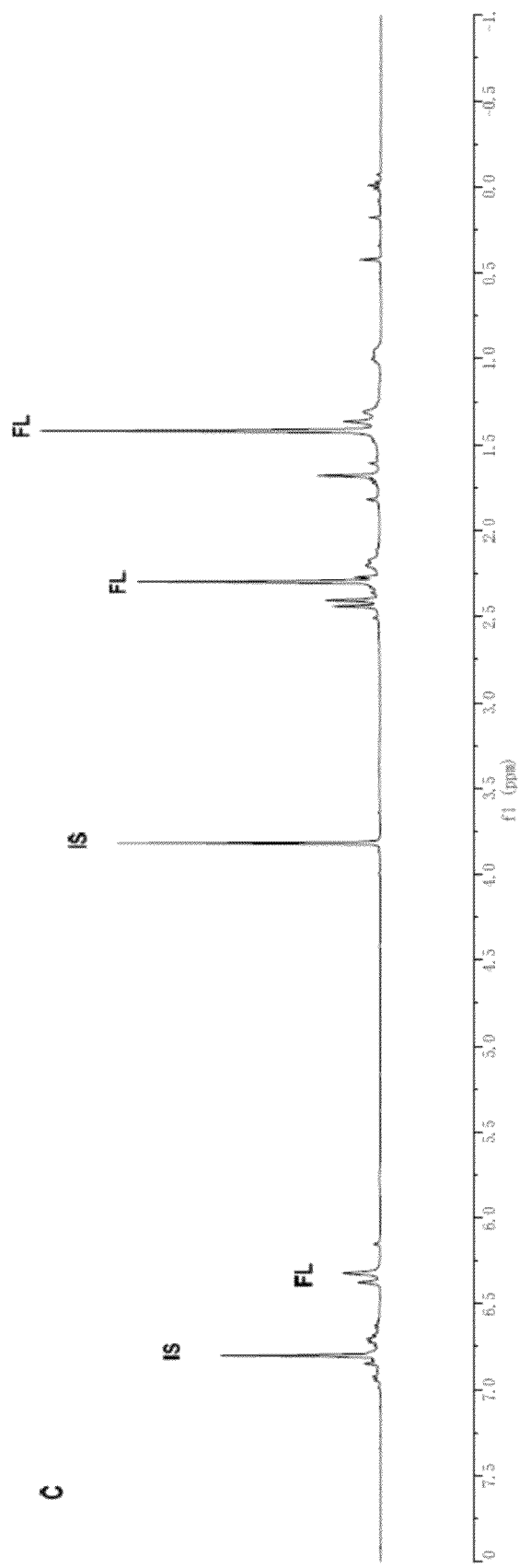
Figure 35:
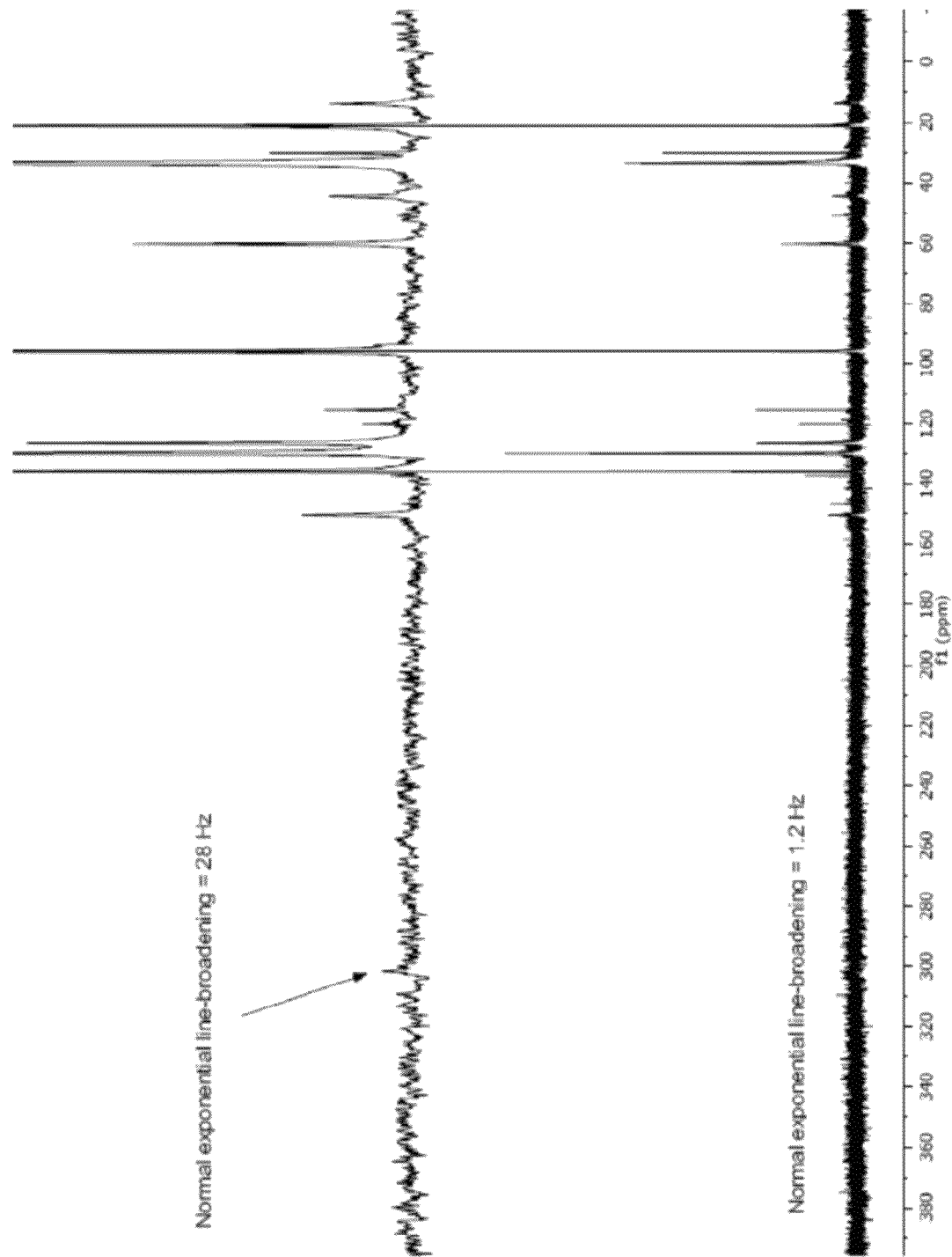
FIG. 35 illustrates the $^{13}$C NMR spectrum of the catalyst precursor in CCl$_4$.
Figure 36:
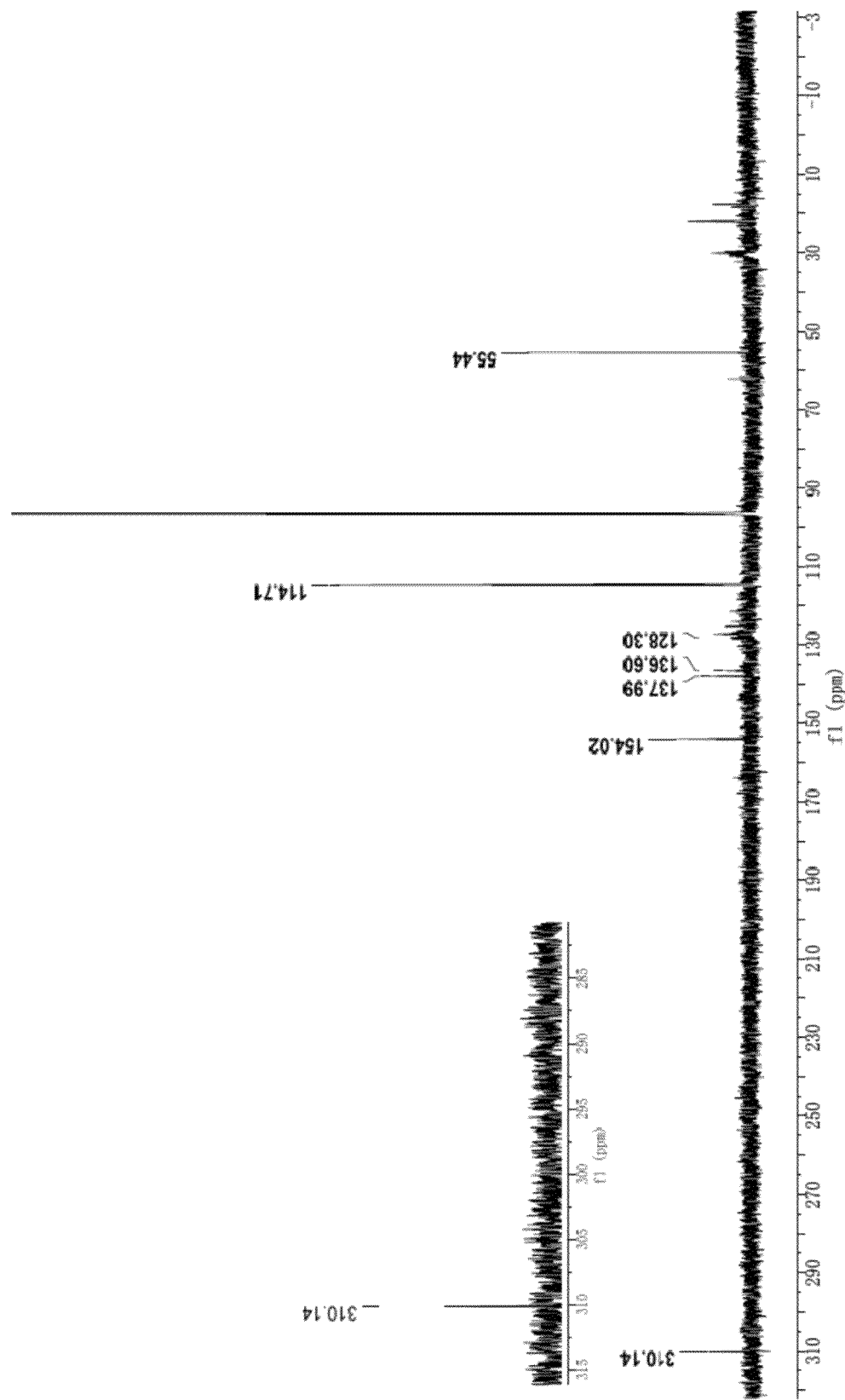
FIG. 36 illustrates the $^{13}$C NMR spectrum of Mo-L7b catalyst in CCl$_4$.

Triphenolsilane ligands (L1-L3) were prepared from the protected salicyclic alcohols (1a-1c, Scheme 8). In order to study the steric effect on catalytic activity, ligands with different ortho substituents (H, Me, i-Pr) were prepared. Conversion of benzylic alcohols (1a-1c) to benzylic bromides (2a-2c), generation of Grignard reagents, followed by coupling with MeSiCl₃ and subsequent deprotection provided ligands L7a-L7c (Scheme 8). The active catalysts 6a-6c were generated by mixing the molybdenum(VI) trisamide precursor with a triphenolic silane ligand in 1:1 ratio in carbon tetrachloride. The complete displacement of the amine ligands with the multidentate ligand L7b was confirmed by $^1$H NMR analysis (FIG. 34). Further $^{13}$C NMR characterization clearly showed the down field shift of the carbyne carbon from 302.3 ppm to 310.1 ppm upon ligand exchange, indicating the formation of the multidentate catalyst 6b (FIGS. 35-36).

Triphenolic silane ligands share similar geometrical features with other multidentate triphenolamine ligands, in which the effective coordination of the three phenol moieties to molybdenum forms cage-shaped metal center and blocks the extra substrate-binding site. However, unlike nitrogen, which can easily coordinate to molybdenum and reduces its Lewis acidity, silicon atom has no lone pair available for the metal-ligand coordination. _ENREF_14 In one embodiment, catalysts 6a-6c possess the advantages of robust multidentate catalysts without sacrificing their catalytic activity. A well-known relatively inert compound, 4-nitropropynylbenzene, was used as the substrate to test the activity. As expected, under the typical alkyne metathesis condition (3 mol % cat. loading, 40° C., ~10 h, dynamic vacuum), the reactions catalyzed by triphenolic silane-based catalysts 6a-6c all showed good yields (54%, 58%, and 54%, respectively). The catalytic activity of catalysts 6a-6c seems not sensitive to the sterics of the ligands. Catalyst 3b was used as the catalyst in the model catalysis studies recited herein.

The solvent effect on the catalyst activity was explored. The pre-generated catalyst 6b in carbon tetrachloride (20 vol %) was used in this study. We used 4-formylpropynylbenzene (1, Table 5) as the substrate and the reaction was carried out at 40° C. with 3 mol % cat. loading. Propynylated benzaldehyde (e.g. 1, Table 5) derivatives are difficult substrates to metathesize, destroying some alkyne metathesis catalysts, such as monodentate siloxy-based molybdenum catalyst (Heppekausen et al., 2010, J. Am. Chem. Soc. 132:11045-11057). The multidentate triphenolsilane catalyst showed 60-74% substrate conversion as well as good solubility in a variety of commonly-used solvents (Table 5). Considerably lower conversions in THF and hexane were observed, presumably due to the coordinating nature of THF and lower solubility of the catalyst in hexane. In one embodiment, carbon tetrachloride is a preferred solvent for the generation of the catalyst. In other solvents, such as toluene, there was slightly reduced catalytic activity (conversion 73% vs. 65%).

TABLE 5

Metathesis reactions in various solvents

OHC—C₆H₄—C≡CH  →(3 mol % cat. 6b, solvent, 40° C., 3.5 h)  OHC—C₆H₄—C≡C—C₆H₄—CHO    eq. 1

| Solvent | Conversion (%) | Solvent | Conversion (%) |
|---|---|---|---|
| n-C₆H₁₄ | 26 | Chlorobenzene | 70 |
| t-BuOMe | 69 | Dichloroethane | 74 |
| THF | 50 | 1,2-dichlorobenzene | 66 |
| CH₂Cl₂ | 61 | 1,2,4-trichlorobenzene | 71 |
| CHCl₃ | 63 | CCl₄ | 79 |
| Toluene | 73 (65) | | |

As noted elsewhere herein, polymerization of 2-butyne byproduct, one of the commonly-observed major side reactions in alkyne metathesis, could poison the metathesis catalyst through the "ring-expansion" mechanism. As a model study, the efficiency of catalyst 6b on inhibiting alkyne polymerization was tested with a large excess of 2-butyne (>100 equiv.). Catalyst 6b showed no polymerization even after 24 h. Furthermore, the catalyst 6b, with or without 2-butyne treatment, showed similar metathesis activity even after exposure to 2-butyne for one week (4-formylpropynyl benzene as the substrate). Without wishing to be limited by theory, a multidentate ligand catalyst of the invention may completely inhibit the small alkyne polymerization, presumably because the cage-shaped catalyst effectively blocks the access of butyne to the extra open binding site on the Mo(VI) center.

Another possible complication with alkyne metathesis is the efficient removal of one of the alkyne product in order to drive the reaction to completion. Since the most widely used common substrates contain methyl substituted alkynes, a typical alkyne metathesis reaction is driven to completion by the removal of 2-butyne byproduct, commonly using continuous dynamic vacuum. However, such an approach usually requires solvent refill, and often does not work well for catalysts highly sensitive to air and moisture.

The feasibility of conducting metathesis reactions with the multidentate triphenolsilane catalysts of the invention in a closed system by using 5 Å molecular sieves was investigated. Comparable or much improved conversions of metathesis reactions catalyzed by this class of silane-based catalysts were observed in the presence of 5 Å molecular sieves (Table 6).

TABLE 6

Homodimerization, RCAM and cyclooligomerization reactions of propynyl substrates.[a,b]

| Entry | Substrate | Product | Method (A or B) | T (° C.) | t (h) | Yield (%) |
|---|---|---|---|---|---|---|
| 1 | 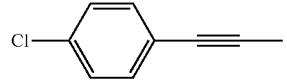 | 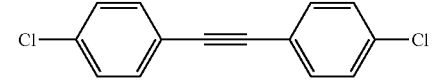 | A | 40 | 4.5 | 91 |
| 2 | 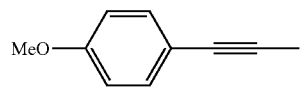 | 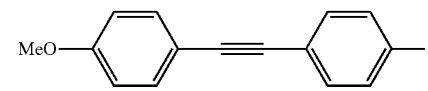 | A | 40 | 5 | 94 |
| 3 | 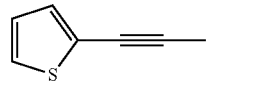 | 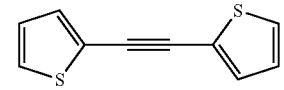 [SMILES: C(#Cc1cccs1)c1cccs1] | A | 40 | 5 | 92 |
| 4 | 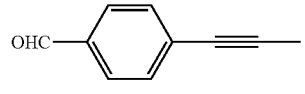 | 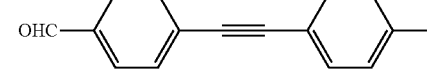 | A<br>B<br>B | 40<br>40<br>40 | 5<br>16<br>16 | 79<br>94<br>96[c] |
| 5 | 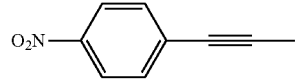 | 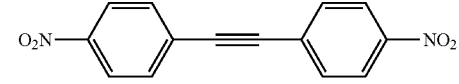 | A<br>B | 40<br>40 | 5 (15)<br>20 | 47 (49)<br>86 |
| 6 | 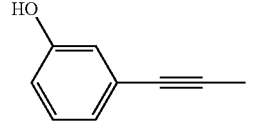 | 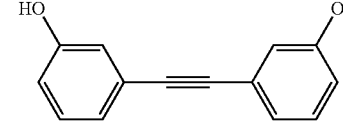 | A<br>B | 70<br>70 | 19<br>20 | 64<br>76 |
| 7 | 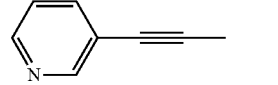 | 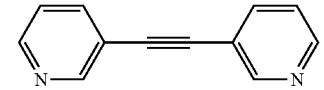 [SMILES: C(#Cc1cccnc1)c1cccnc1] | A<br>B<br>B | 70<br>70<br>70 | 4<br>4 (7)<br>4 | 84<br>84 (88)<br>90[c] |
| 8 | 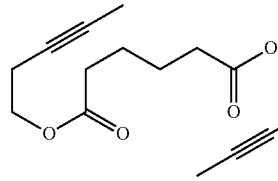 | 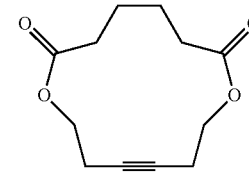 | A | 40 | 3.5 | 95 |

TABLE 6-continued

Homodimerization, RCAM and cyclooligomerization reactions of propynyl substrates.[a,b]

| Entry | Substrate | Product | Method (A or B) | T (° C.) | t (h) | Yield (%) |
|---|---|---|---|---|---|---|
| 9 | 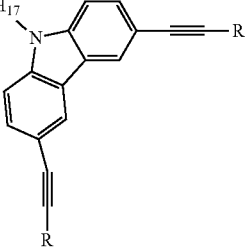 R = 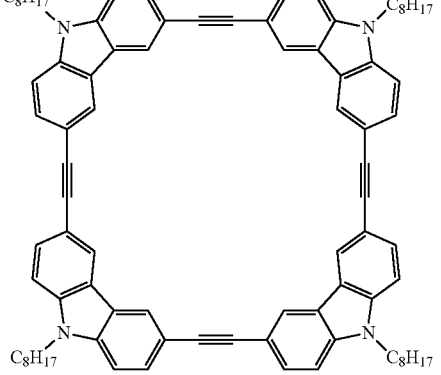 R = Me, for method B | 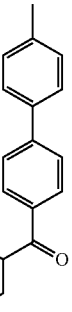 | B | 20 40 | 0.5 5 | 93[d] >99 |
| 10 | 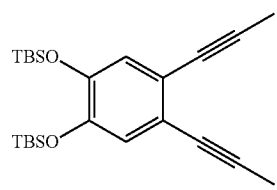 [SMILES: CC#Cc1cc(O[Si](C)(C)C(C)(C)C)c(O[Si](C)(C)C(C)(C)C)cc1C#CC] | 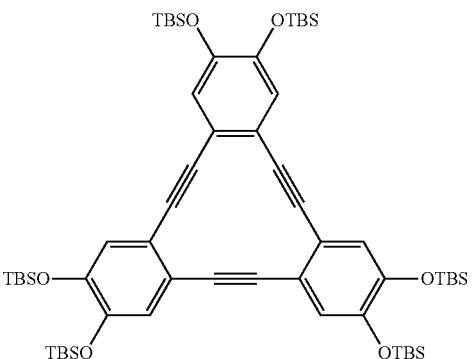 [SMILES: CC(C)(C)[Si](C)(C)Oc1cc2c(cc1O[Si](C)(C)C(C)(C)C)C#Cc1cc(O[Si](C)(C)C(C)(C)C)c(O[Si](C)(C)C(C)(C)C)cc1C#Cc1cc(O[Si](C)(C)C(C)(C)C)c(O[Si](C)(C)C(C)(C)C)cc1C#C2] | B | 40 | 16 | >99 |

[a]Catalyst 6b and solvent CCl$_4$ were used unless stated otherwise;
[b]3 mol % catalyst loading for entries 1-5 and 7-10; 10 mol % for entry 6;
[c]Catalyst 6c was used;
[d]precipitation-driven cyclooligomerization.
Method A: Vacuum with 30 min-interval without the addition of molecular sieves;
Method B: 150 mg MS 5 Å/0.1 mmol for entries 4-7 and 300 mg MS 5 Å/0.1 mmol for entries 9 and 10.

Such condition worked particularly well for those challenging substrates (e.g., 4-nitropropynylbenzene), which usually require longer reaction time and higher catalyst loading under conventional dynamic vacuum conditions. In entry 5 (Table 6), the conversion was improved from 49% to 88% when 5 Å molecular sieves were used as 2-butyne scavenger. Such closed system condition may also be applied to the synthesis of shape-persistent macrocycles in almost quantitative yields on multigram scale (2.6 g, entry 10). For the same multigram macrocycle synthesis (entry 10), the catalyst loading could be reduced to as low as 0.5 mol % without sacrificing the yield, at slightly elevated temperature (55° C., 4.31 g, 98%). The carbazole-based cyclic tetramer was also prepared in one step from a simple propynyl-substituted monomer in quantitative yield (entry 9, Table 6). Thus the catalyst system of the invention may allow convenient access to shape-persistent 2 D or 3D molecular architectures that have been recognized as important building blocks for the future nanotechnology.

Substrate scope was then investigated. The reactions were performed either under dynamic vacuum or in the presence of 5 Å molecular sieves. Table 2 summarizes reactions of different substrates catalyzed by in situ generated catalyst 6b. Catalyst 6b was compatible with all the different substrates tested, providing the corresponding products in good to excellent yields. The substrates included: (i) compounds containing electron-donating/electron-withdrawing substituents, (ii) heterocyclic molecules, (iii) the ring closing alkyne metathesis (RCAM) of diyne to cycloalkyne, (iv) compounds containing free phenolic hydroxyl group (entry 6), and (v) the precipitation-driven cyclooligomerization reaction of the carbazole diyne substrate (entry 9). Even those challenging substrates, containing nitro, or aldehyde functional groups were compatible with the conditions to give the corresponding dimers (86-96%). Half-lives of less than 1 hour were generally observed for those reactions, even at 40° C. with catalyst loading as low as 3 mol % (based on Mo). The metathesis reaction worked surprisingly well with the phenol substrate (entry 6), which represents the first successful alkyne metathesis of a substrate containing free phenolic hydroxyl groups (Kaneta et al., 1995, Chem. Lett. 627-628). This enables the synthesis and applications of other phenol-based substrates, including shape-persistent macrocycles.

Catalyst 6b showed good stability in solution. Its metathesis activity at different time intervals after their generation (in the absence of any alkyne substrates) was tested, using the 4-formylpropynylbenzene as the model compound. Complex 6b showed no loss in catalytic activity after 24 h storage at room temperature and remained active even after one week. When stored in solution at □30° C., catalyst 6b did not show any noticeable decrease in activity for a period of more than 3 months. The presence of only 1 mol % of 100-day aged catalyst 6b was sufficient to catalyze the cyclooligomerization of monomer 10 (Table 6) to form macrocycle 11 in 5 h at 40° C. in 90% yield:

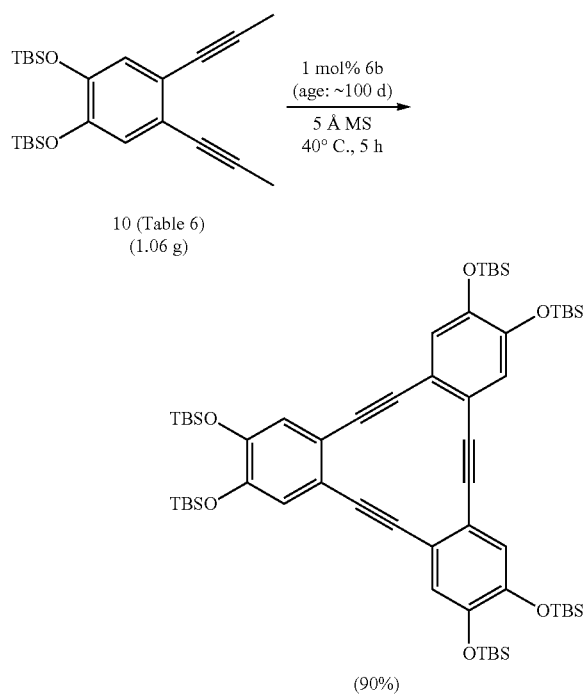

Such a long lifetime is desired particularly for the alkyne metathesis of tough substrates, and also for industrial processes where catalyst stability is often of paramount importance.

The triphenolsilane-based, uncharged, multidentate alkyne metathesis catalysts of the invention have good functional group tolerance, fast reaction rate and long lifetime (remaining active in solution for months. These catalysts were compatible with 5 Å molecular sieves that serve as small alkyne byproduct scavengers. A variety of tough substrates (e.g., pyridine, phenol, benzaldehyde, nitrobenzene) were successfully cross-metathesized. Moreover, shape-persistent aryleneethynylene macrocycles were prepared in almost quantitative yields on multi-gram scale in a closed system, highlighting the feasibility of achieving convenient access to a variety of novel 2-D and also 3-D molecular architectures targeting various potential applications (e.g., carbon capture, artificial photosynthesis, catalysis, etc.).

Kits

A kit of the invention may comprise at least one compound of the invention. In one embodiment, a kit of the invention comprises a compound of formula (I). In another embodiment, a kit of the invention comprises a compound of formula (II), (III) or (IV). Use of a kit may be preferable to the use of an individual compound sold separately if it provides additional value for the user. Use of a kit may also be preferable if the compounds as provided in the kit are more chemically stable, or less chemically reactive, than the corresponding isolated compounds.

Thus, in one aspect, provided herein is a kit for the preparation of a compound of formula (III), comprising a compound of formula (I) and a metal alkylidyne compound with exchangeable ligands. In one embodiment, the compound of formula (III) is a compound of formula (IV), and the compound of formula (I) is a compound of formula (II). In another embodiment, the compound of formula (IV) is Mo-L1 and the compound of formula (II) is L1.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

General Experimental Techniques

The $^1$H and $^{13}$C NMR spectra were recorded on 400 or 500 MHz Varian spectrometers. Chemical shifts are expressed in parts per million (δ) using the residual solvent protons as an internal standard. Coupling constants (J) are reported in Hertz (Hz), and splitting patterns are designated as s (singlet), d (doublet), t (triplet), q (quartet), m (multiplet) and br (broad). MALDI-TOF spectra were recorded on a Voyager-DE™, STR Biospectrometry Workstation using sinapic acid as the matrix. All air or moisture sensitive reactions, including all metathesis reactions were run under an atmosphere of argon. Analytical gel permeation chromatography (GPC) was performed using a Viscotek GPCmax™, a Viscotek Model 3580 Differential Refractive Index (RI) Detector, a Viscotek Model 3210 UVNIS Detector and a set of two Viscotek Viscogel columns 7.8×30 cm, 1-MBLMW-3078, and 1-MBMMW-3078 columns, with THF as the eluent at 30° C. The analytical GPC was calibrated using monodisperse polystyrene standards.

Starting Materials

Salicylaldehyde, 2-hydroxy-5-bromobenzaldehyde, 2-hydroxy-3-methylbenzaldehyde, paraformaldehyde, pyrrole, mesitaldehyde, 2,4,6-trihydroxybenzaldehyde, sodium tert-butoxide, 2-(dicyclohexylphosphino) biphenyl, tert-butylamine, 1-bromo-3,5-dimethylbenzene, 2-hydroxy-benzaldehyde, 2-hydroxy-3-isopropylbenzoic acid and molybdenum pentachloride were purchased from Sigma Aldrich and used as received.

The Mo(VI) trisamide precursor [tris(N-tert-butyl-N-(3,5-dimethylphenyl)amido) Mo(VI) propylidyne] was prepared by following the reported procedure (Zhang et al., 2007, Org. Synth. 84:163).

Example 1

Synthesis of Ligands

Ligand tris(2-hydroxy-5-nitro-benzyl)amine (L1 in Scheme 1)

2-Hydroxy-5-nitrobenzaldehyde (1) (2 g, 12.0 mmol) was methylated using methyl iodide (1.7 g, 36 mmol) and anhydrous potassium carbonate (1.7 g, 36 mmol) in DMF (7 mL), by stirring at room temperature for 12 h. After the TLC showed complete disappearance of the starting material, the reaction mixture was poured in to crushed ice leading to the precipitation of the product. This was further purified by column chromatography over silica gel using 1:10 ethyl acetate/hexane to obtain a yield of 94% (2.04 g) of compound (2). For characterization, the spectroscopic data was consistent with what has been previously reported (Yang et al., 2007, Org. Lett. 9:5287).

$^1$H NMR (CDCl$_3$, 500 MHz): δ 10.48 (1H, s), 8.7 (1H, d, J=3.0 Hz), 8.47 (1H, dd, J=9 Hz), 7.05 (1H, d, 9 Hz), 4.04 (3H, s); $^{13}$C NMR (CDCl$_3$, 100 MHz): 187.8, 165.8, 141.8, 130.9, 124.8, 112.5, 57.0.

The methyl protected salicyl aldehyde from the previous step (2) (1.52 g, 8.4 mmol) was subjected to reductive amination using ammonium acetate (162 mg, 2.1 mmol) and triacetoxy sodium borohydride (2.755 g, 13.0 mmol), by stirring at room temperature for 12 h in dry THF. After the TLC showed complete disappearance of the starting material, the reaction mixture was poured in to crushed ice leading to the precipitation of the product. This was further purified by column chromatography over silica gel using 1:4 ethyl acetate/hexane to obtain a yield of 69% (655.0 mg) of compound (3).

$^1$H NMR (CDCl$_3$, 500 MHz): δ 8.35 (3H, d, J=3.0 Hz), 8.09 (3H, dd, J=9 Hz), 6.82 (3H, d, J=9 Hz), 3.94 (3H, s), 3.79 (3H, s); $^{13}$C NMR (CDCl$_3$, 100 MHz): 162.7, 141.3, 128.7, 126.0, 124.9, 109.9, 56.3, 54.0. HR-MS (ESI): calcd. for C$_{24}$H$_{24}$N$_4$O$_9$ [M+Na$^+$] 535.1435. Found: 535.1427.

For the preparation of the $^{15}$N labeled sample, $^{15}$N labeled ammonium acetate was used keeping all other conditions the same. For characterization, the spectroscopic data was compared with that of the unlabeled sample for consistency.

The tribenzyl amine obtained after reductive amination (500 mg, 0.1 mmol) was then subjected to deprotection using LiI (500 mg, 3 mmol) and quinoline (7 mL) at 165-170° C. for 1 h. The work up consisted of the addition of 2 N HCl to precipitate out the product from quinolone, which was separated by vacuum filtration. Since the product so obtained was contaminated with quinoline, it was redissolved in 0.1 M NaOH and repeatedly washed with dichloromethane to remove residual quinoline. Neutralization of the aqueous layer with 2 N HCl precipitated out the product as a yellow solid. The product so obtained was further purified by column chromatography over silica gel using ethyl acetate-1% methanol/ethyl acetate. Yield: 87% (395.0 mg) of compound tris(2-hydroxy-5-nitro-benzyl)amine (L1 in Scheme 1).

$^1$H NMR (CD$_3$OD, 500 MHz): δ 8.15 (3H, d, J=3.0 Hz), 7.98 (3H, dd, J=9 Hz), 6.8 (3H, d, J=9 Hz), 3.9 (3H, s); $^{13}$C NMR (DMSO, 100 MHz): 163.3, 139.9, 126.8, 125.5, 116.0, 54.0; HR-MS (ESI): calcd. for C$_{21}$H$_{18}$N$_4$O$_9$ [M+H$^+$]: 471.1147. Found: 471.1156.

Figure 3:
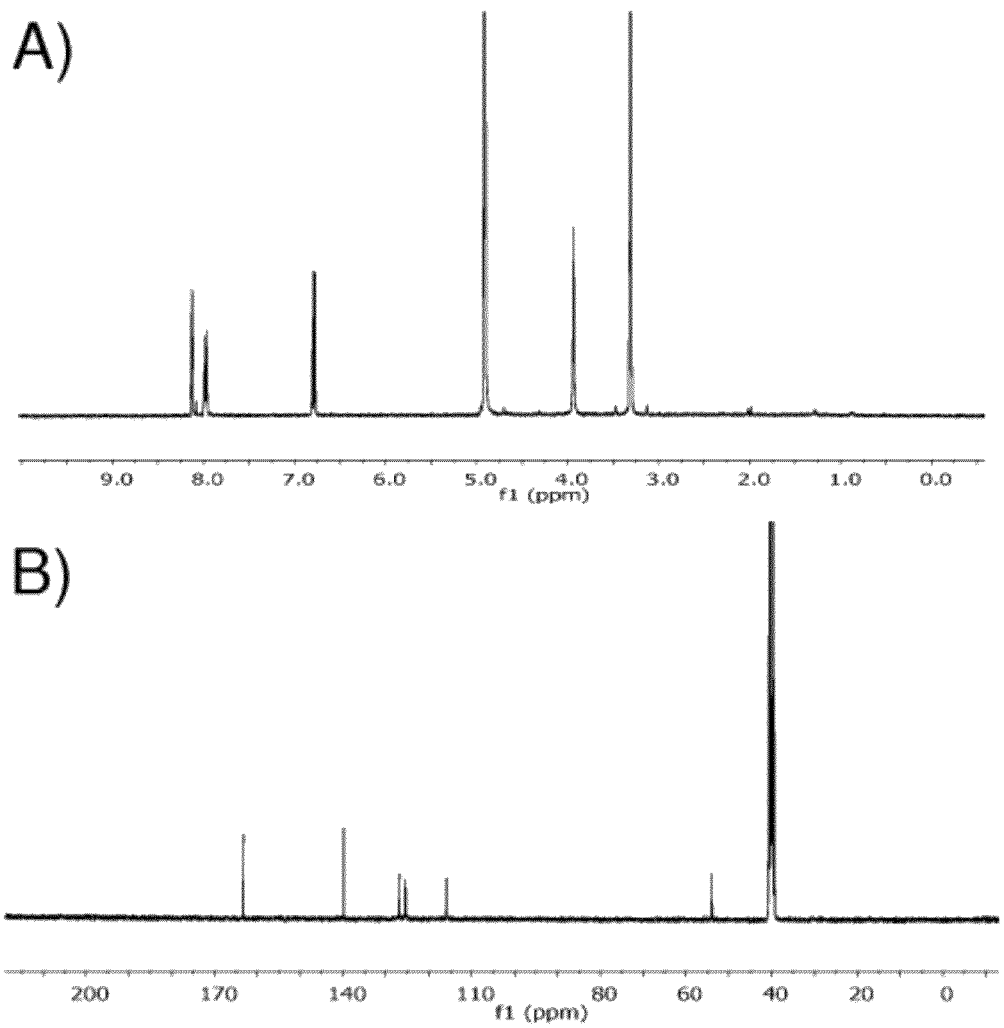
FIG. 3, comprising

For characterization of the $^{15}$N labeled sample, the spectroscopic data was compared with that of the unlabeled sample for consistency (FIGS. 3 and 5).

TABLE 7

| Crystal Data for Mo-L1 Dimer Complex | |
|---|---|
| Empirical formula | C48H40Mo2N8O18, (C6H10) |
| Crystal color | orange |
| Temperature | 123(2) K |
| Wavelength | 0.71073 Å |
| Crystal system | orthorhombic |
| Space group | 'Pcca' |
| Unit cell dimensions | a = 25.0360(6) Å α = 90.00 |
|  | b = 13.8320(3) Å β = 90.00 |
|  | c = 25.1743(7) Å γ = 90.00 |
| Cell volume | 8717.8(4) Å3 |
| Z | 16 |
| Density | 0.948 Mg/m3 |
| Absorption coefficient | 0.337 mm−1 |
| F_000 | 2520 |
| Crystal size | 0.32 × 0.28 × 0.21 |
| Theta range for data collection | 2.29 to 33.18 |
| Reflections collected | 22951 |
| Goodness-of-fit on F2 | 0.834 |
| Max. and min. transmission | 0.746 and 0.628 |

Ligand tris(2-hydroxy-benzyl)amine (L5)

Ligand tris(o-hydroxy-benzyl)amine (L5) was synthesized by following reported procedure (Prins et al., 2006, Tet. Let. 47:2735).

Scheme 4: Synthesis of ligand L5.

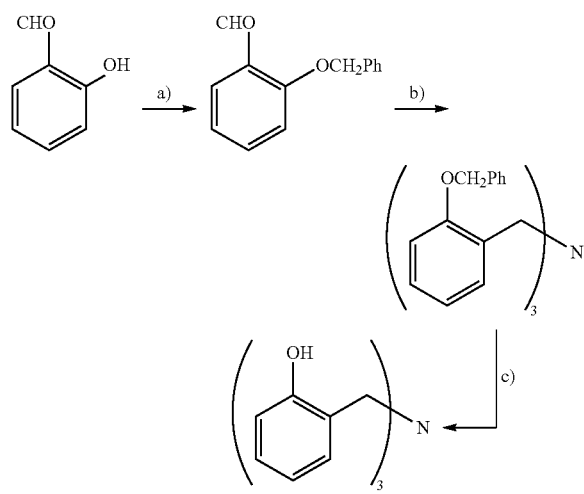

Conditions: (a) benzylbromide, K$_2$CO$_3$, DMF, 70° C., 92%; (b) NaBH(OAc)$_3$, NH$_4$OAc, THF, RT, 70%; (c) Pd/C, H$_2$, ethyl acetate/methanol, RT, 88%.

Ligand L2 (tris(2-hydroxybenzyl)-methylammonium iodide),

Ligand L3 (tris(5-bromo-2-hydroxy-benzyl)-methylammonium iodide),

Ligand L4 (tris(2-hydroxy-3-methyl-5-nitro-benzyl)-methylammonium iodide)

Scheme 5: Synthesis of ligands L2-L4.

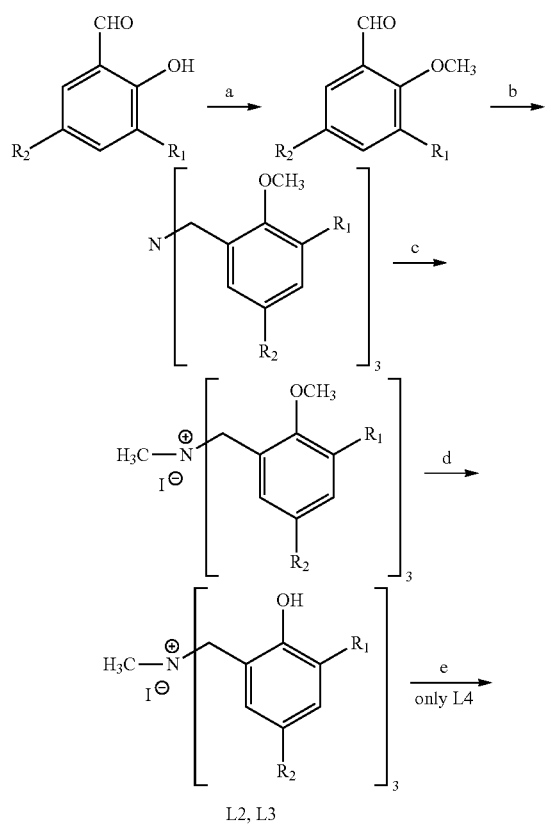

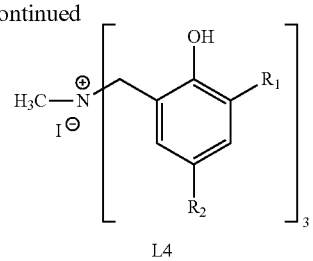

L2 R$_1$ = H, R$_2$ = H
L3 R$_1$ = H, R$_2$ = Br
L4 R$_1$ = CH$_3$, R$_2$ = NO$_2$

Conditions: (a) Methyl iodide, K$_2$CO$_3$, DMF, RT, 94-97%. (b) NaBH(OAc)$_3$, NH$_4$OAc, THF, RT, 64-69%. (c) Methyl iodide, 70-80° C., 95%. (d) BBr$_3$, CH$_2$Cl$_2$, -78° C. to RT, 85-89%. (e) 9% HNO$_3$, tetrachloroethane, sonication, RT, 65%.

Substituted hydroxybenzaldehydes (12.0 mmol) were protected by reacting with methyl iodide (1.7 g, 36 mmol) and anhydrous potassium carbonate (1.7 g, 36 mmol) in DMF (7 mL) for 12 h at room temperature. After the TLC showed complete disappearance of the starting material, the reaction was quenched by adding distilled water and extracted with ethyl acetate. The ethyl acetate fraction was concentrated under vacuum and subjected to column chromatography over silica gel (ethyl acetate/hexane, 1/10, v/v) to obtain the product in 94-97% yield.

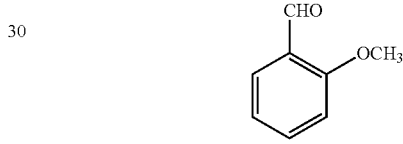

$^1$H NMR (400 MHz, CDCl$_3$) δ 10.47 (s, 1H), 7.83 (dd, J=7.7, 1.8 Hz, 1H), 7.58-7.52 (m, 1H), 7.02 (td, J=7.6, 0.8 Hz, 1H), 6.99 (d, J=8.4 Hz, 1H), 3.93 (s, 3H). $^1$H NMR data are consistent with that reported in literature (Prins et al., 2006, Tet. Let. 47:2735).

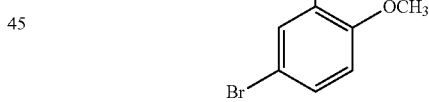

$^1$H NMR (500 MHz, CDCl$_3$) δ 10.40 (s, 1H), 7.94 (d, J=2.6 Hz, 1H), 7.65 (dd, J=8.9, 2.6 Hz, 1H), 6.91 (d, J=8.9 Hz, 1H), 3.94 (s, 3H). $^1$H NMR data are consistent with that reported in literature (Ram & Manoj, 2008, J. Org. Chem. 73:5633).

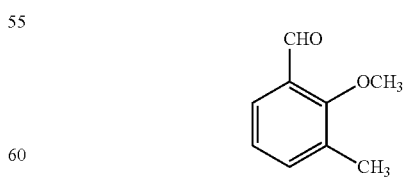

$^1$H NMR (500 MHz, CDCl$_3$) δ 10.40 (s, 1H), 7.70 (ddd, J=7.7, 1.2, 0.6 Hz, 1H), 7.46 (ddd, J=7.4, 1.7, 0.8 Hz, 1H), 7.15 (t, J=7.6 Hz, 1H), 3.90 (s, 3H), 2.36 (s, 3H). $^1$H NMR data are consistent with that reported in literature (Prins et al., 2006, Tet. Let. 47:2735).

The methyl protected salicylaldehyde from the previous step (8.4 mmol) was subjected to reductive amination using ammonium acetate (162 mg, 2.1 mmol) and sodium triacetoxyborohydride (2.755 g, 13.0 mmol) at room temperature for 24-48 h in dry THF. After the TLC showed complete disappearance of the starting material, the reaction was quenched by adding distilled water and extracted with ethylacetate. The ethyl acetate fraction is concentrated under vacuum and subjected to column chromatography over silica gel (dichloromethane/hexane, 3:1, v/v to 1 vol % MeOH in dichloromethane) to obtain the product in 64-69% yield.

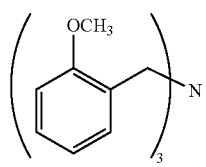

$^1$H NMR (400 MHz, CDCl$_3$) δ 7.72 (d, J=7.4 Hz, 3H), 7.18 (t, J=7.8 Hz, 3H), 6.94 (t, J=7.4 Hz, 3H), 6.81 (d, J=8.2 Hz, 3H), 3.78 (s, 9H), 3.70 (s, 6H). $^1$H NMR data is consistent with that reported in literature (Prins et al., 2006, Tet. Let. 47:2735) (Prins et al., 2006, Tet. Let. 47:2735).

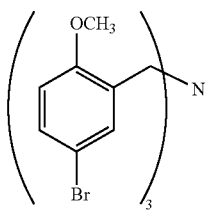

$^1$H NMR (500 MHz, CDCl$_3$) δ 7.63 (d, J=2.5 Hz, 3H), 7.26 (dd, J=8.7, 2.5 Hz, 3H), 6.68 (d, J=8.7 Hz, 3H), 3.82 (s, 9H), 3.60 (s, 6H). $^{13}$C NMR (101 MHz, CDCl$_3$) δ 156.9, 133.0, 130.5, 130.2, 112.9, 111.9, 55.7, 52.9. HR-MS (ESI): calcd. for C$_{24}$H$_{24}$Br$_3$NO$_3$ [M+H$^+$]: 611.9380. Found: 611.9378.

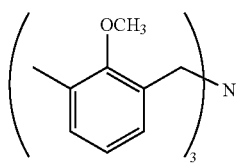

$^1$H NMR (500 MHz, CDCl$_3$) δ 7.57 (dd, J=7.2, 2.1 Hz, 3H), 7.08-7.00 (m, 6H), 3.67 (s, 15H), 2.29 (s, 9H). $^1$H NMR data is consistent with that reported in literature (Prins et al., 2006, Tet. Let. 47:2735).

The tribenzylamine obtained after reductive amination (0.655 mmol) was converted to the corresponding quaternary salts by using methyl iodide (1.0 mL) under neat conditions at 70-80° C., with regular monitoring of the reaction by $^1$H NMR. After complete disappearance of the starting material, the heating was stopped and the excess methyl iodide was removed by rotary evaporation. The crude reaction mixture was washed with ice cold diethylether and ethyl acetate to remove the unreacted starting material. The solid after washing was dried under vacuum and proceed to the next step. The yields were about 95%.

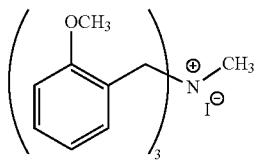

$^1$H NMR (500 MHz, CDCl$_3$) δ 7.85 (dd, J. 7.6, 1.6 Hz, 3H), 7.47 (td, J. 8.4, 1.7 Hz, 3H), 7.07 (td, J=7.5, 0.8 Hz, 3H), 6.96 (d, J. 8.3 Hz, 3H), 5.01 (s, 6H), 3.77 (s, 9H), 2.61 (s, 3H). $^{13}$C NMR (101 MHz, CDCl$_3$): δ 159.0, 136.1, 132.7, 121.4, 116.1, 111.7, 60.1, 26.0, 45.3. HR-MS (ESI): calcd. for C$_{25}$H$_{30}$NO$_3$$^+$ [M$^+$]: 392.2221. Found: 392.2232.

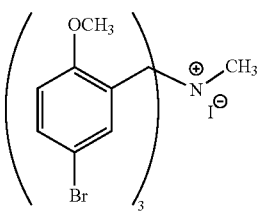

$^1$H NMR (400 MHz, DMSO) δ 7.84 (d, J=2.6 Hz, 3H), 7.69 (dd, J=8.9, 2.5 Hz, 3H), 7.14 (d, J=9.0 Hz, 3H), 4.44 (s, 6H), 3.79 (s, 9H), 2.77 (s, 3H). $^{13}$C NMR (101 MHz, DMSO) δ, 158.9, 138.1, 135.6, 118.8, 115.0, 112.7, 60.0, 56.9, 44.2. HR-MS (ESI): calcd. for C$_{25}$H$_{27}$NO$_3$$^+$ [M$^+$]: 625.9536. Found: 625.9536.

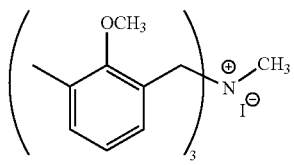

$^1$H NMR (500 MHz, CDCl$_3$) δ 7.63 (d, J=7.6 Hz, 3H), 7.34-7.30 (d, J=7.6 Hz, 3H), 7.14 (t, J=7.6 Hz, 3H), 5.15 (s, 6H), 3.54 (s, 9H), 2.34 (s, 3H), 2.30 (s, 9H). HR-MS (ESI): calcd. for C$_{28}$H$_{36}$NO$_3$$^+$ [M$^+$]: 434.2690. Found: 434.2703.

The tribenzylammonium salt obtained after quaternization (1.35 mmol) was subjected to deprotection by using BBr$_3$ (17.53 mmol) in methylene chloride (30 mL) at −78° C. The reaction was allowed to slowly warm up to room temperature and stirred for 12 h. The reaction mixture was poured into crushed ice under vigorous stirring. The product precipitated out in the methylene chloride layer as a white solid, in high purity. This was then filtered and washed with methylene chloride and water and dried under vacuum. The yields were around 85-89%.

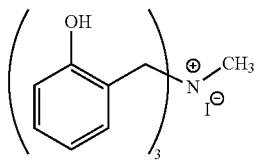

$^1$H NMR (500 MHz, CD$_3$OD) δ 7.43-7.40 (m, 3H), 7.38 (td, J=8.0, 1.6 Hz, 3H), 6.99-6.94 (m, 6H), 4.62 (s, 6H), 2.79

(s, 3H). $^{13}$C NMR (101 MHz, CD$_3$OD) δ 159.0, 136.1, 132.7, 121.4, 116.1, 111.7, 60.1, 56.0. HR-MS (ESI): calcd. for C$_{22}$H$_{24}$NO$_3$$^+$ [M$^+$]: 350.1756. Found: 350.1758.

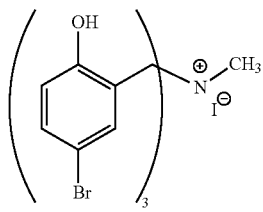

$^1$H NMR (400 MHz, CD$_3$OD) δ 7.64 (d, J=2.5 Hz, 3H), 7.50 (dd, J=8.8, 2.5 Hz, 3H), 6.90 (d, J=8.8 Hz, 3H), 4.58 (s, 6H), 3.34 (s, 3H), 2.84 (s, 3H). $^{13}$C NMR (101 MHz, CD$_3$OD) δ 157.0, 137.1, 135.2, 117.9, 116.5, 111.3, 60.3, 43.4. HR-MS (ESI): calcd. for C$_{22}$H$_{21}$Br$_3$NO$_3$$^+$ [M$^+$]: 583.9067. Found: 583.9069.

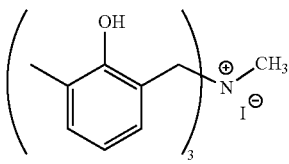

$^1$H NMR (500 MHz, CD$_3$OD) δ 7.30-7.24 (m, 6H), 6.92 (t, J=7.6 Hz, 3H), 4.67 (s, 6H), 2.78 (s, 3H), 2.26 (s, 9H). $^{13}$C NMR (101 MHz, CD$_3$OD) δ 155.5, 133.6, 132.5, 125.8, 120.2, 115.5, 61.1, 15.7. HR-MS (ESI): calcd. for C$_{25}$H$_{30}$NO$_3$$^+$ [M$^+$]: 392.2221. Found: 392.2212.

To obtain the ligand L4, the triphenolamine (70.0 mg, 0.135 mmol) from the previous step was sonicated for 2 h at room temperature in the presence of 9% nitric acid (15 mL) and tetrachloroethane (7 mL). The suspension was kept in an ice bath for another 30 minutes leading to the precipitation of the product. The product was then filtered under vacuum and washed thoroughly with water, tetrachloroethane and finally with methylene chloride. The white solid so obtained was dried under vacuum to obtain the product 57 mg in 65% yield.

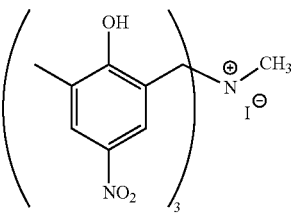

$^1$H NMR (500 MHz, CD$_3$OD) δ 8.36 (m, 3H), 8.26 (m, 3H), 4.81 (s, 6H), 2.98 (s, 3H), 2.38 (s, 9H). $^{13}$C NMR (101 MHz, CD$_3$OD) δ 161.8, 140.4, 128.6, 128.5, 127.0, 115.6, 74.6, 60.7, 16.0. HR-MS (ESI): calcd. for C$_{25}$H$_{27}$N$_4$O$_9$$^+$ [M$^+$]: 527.1773. Found: 527.1771.

Example 2

General Procedure for Metathesis Experiments

The ligand and the precursor were premixed in dry carbon tetrachloride for 2-4 minutes to initiate the in situ generation of the catalyst. Subsequently, the substrate was added and the stirring was continued with regular monitoring of the reaction by NMR. During the reaction, the solution was exposed to vacuum (~4-8 times, 20 sec each time) to remove the metathesis byproduct 2-butyne. The loss of solvent during the application of vacuum was compensated by adding fresh solvent each time.

For purification of the metathesis reaction products of entries 1-6,8,10 and 11 in Table 1, the solvent was removed by rotary evaporation and the residue obtained was subjected to column chromatography over silica gel. For entry 12 in Table 2, the reaction mixture was filtered before the filtrate was concentrated and subjected to column chromatography over silica gel.

For purification of the metathesis reaction products of entries 1-7 in Table 3, the solvent was removed by rotary evaporation and the residue obtained was subjected to column chromatography over silica gel. For the precipitation driven metathesis reaction of entry 8 in Table 3, the reaction mixture was filtered to remove the byproduct diarylalkyne and the filtrate is concentrated and subjected to column chromatography over silica gel.

For characterization of all known metathesis substrates and products, the analytical and spectroscopic data are compared with those of literature reported values.

Example 3

Compounds Prepared in Tables 1-2

Synthesis of Substrates

The substrates for entries 1-5, 10-12 in Tables 1 and 2 were obtained by standard Negishi and Sonogashira coupling reactions following reported procedures (Zhang et al., 2004, J. Am. Chem. Soc. 126:329; Bindl et al., 2009, J. Am. Chem. Soc. 131:9468; Zhang & Moore, 2004, J. Am. Chem. Soc. 126:12796; Zhang & Moore, 2005, J. Am. Chem. Soc. 127: 11863; Zhou & Larock, 2006, J. Org. Chem. 71:7422; Chang et al., 2004, J. Am. Chem. Soc. 126:12796; Zhao et al., 2006, J. Org. Chem. 71:7422). The substrate for entry 6 was made by the diesterification of adipic acid with 3-pentyn-1-ol, following reported procedure (Furstner et al., 1999, J. Am. Chem. Soc. 121:11108). The substrate for entry 7 was made by the reaction of 1-heptyne and 1-chloro-2-octyne, following reported procedure (Tallman et al., 2004, J. Am. Chem. Soc. 126:9240).

Dimethyldipropynyl Silane:

To a well stirred solution of (CH$_3$)$_2$SiCl$_2$ (150 mg, 1.2 mmol) in THF (5 mL), propynyl lithium (140 mg, 3 mmol) was added and continued stirring for 4 h at room temperature. The reaction mixture was then treated with Et$_2$O-aq. NH$_4$Cl solution. The organic layer was separated and dried over anhydrous Na$_2$SO$_4$. The yellow liquid so obtained was chromatographed over silica gel using hexane. The dimethyldipropynyl silane was obtained as a colorless liquid in quantitative yields.

$^1$H NMR (CDCl$_3$, 500 MHz): δ 1.90 (6H, s), 0.28 (6H, s); $^{13}$C NMR (CDCl$_3$, 100 MHz): 104.2, 81.2, 30.3, 29.9, 0.8. HR-MS (ESI): calcd. for C$_8$H$_{12}$Si [M+Li$^+$]: 143.0863. Found: 143.0865.

Synthesis of Substrate 12:

The diarylethynyl carbazole monomer (12) was made by modifying reported procedures (Zhang & Moore, 2004, J. Am. Chem. Soc. 126:12796; Zhao et al., 2006, J. Org. Chem. 71:7422), as shown in FIG. 2.

$^1$H NMR (CDCl$_3$, 500 MHz): δ 8.33 (2H, s), 7.91 (4H, d, J=10.5 Hz), 7.85 (4H, d, J=10 Hz), 7.75 (4H, d, J=10.5 Hz), 7.68 (10H, m), 7.62 (2H, t, J=10 Hz), 7.51 (4H, t, J=10.5 Hz), 7.40 (2H, d, J=10.5 Hz), 4.33 (2H, t, J=9.0 Hz), 1.51 (2H, p, 9.0 Hz), 1.4-1.2 (26H, m), 0.87 (3H, t, J=8.0 Hz); $^{13}$C NMR (CDCl$_3$, 100 MHz): 196.5, 144.6, 140.8, 139.4, 137.9, 136.6, 132.7, 132.3, 131.1, 130.3, 130.0, 128.6, 127.4, 127.0, 124.5, 124.0, 122.7, 114.0, 109.3, 92.2, 43.6, 32.1, 29.9, 29.8, 29.7, 29.6, 29.2, 27.5, 22.9, 14.3. HRMS (ESI): calcd. for C$_{70}$H$_6$SNO$_2$ [M+Li$^+$]: 958.5171. Found: 958.5213.

General Procedure For Metathesis Experiments

The ligand tris(2-hydroxy-5-nitro-benzyl)amine (1.5 mg, 0.0032 mmol) and the precursor (2.0 mg, 0.0031 mmol) were premixed in dry carbon tetrachloride (3 mL for all entries in Table 1 except entry 6, where the solvent volume was doubled to ensure ring closing alkyne metathesis) for 20 minutes to generate the catalyst in situ. Subsequently, the substrate (0.107 mmol) was added and the stirring was continued for 4-7 h (for entries 1-2, 5-8 and 10-12 in Tables 1 and 2) and 7-12 h (for entries 3 and 4 in Table 1) with regular monitoring of the reaction by NMR. During the reaction, the solution was exposed to vacuum (20 sec each time, ~3-4 times for entries 1, 2, 5, 6 and 8 in Table 1 and ~6-7 times for entries 3 and 4 in Table 1) to remove the metathesis byproduct 2-butyne and the loss of solvent during the application of vacuum was compensated by adding fresh solvent each time.

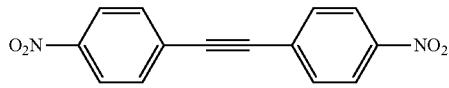 [SMILES: O=[N+]([O-])c1ccc(C#Cc2ccc([N+](=O)[O-])cc2)cc1]

$^1$H NMR (CDCl$_3$, 500 MHz): δ 8.26 (4H, d, J=11.0 Hz), 7.72 (4H, d, J=11.0 Hz); $^{13}$C NMR (CDCl$_3$, 100 MHz): 147.8, 132.9, 132.8, 129.1, 124.0, 92.2. HR-MS (ESI): calcd. for C$_{14}$H$_8$N$_2$O$_4$ [M+Cl$^-$]: 303.0178. Found: 303.0171.

$^1$H NMR (CDCl$_3$, 500 MHz): δ 3.18 (4H, br m), 2.18 (4H, br, m), 1.5 (4H, p), 1.4-1.3 (8H, br m), 0.9 (2H, t, 6H). EI-MS: m/z calcd. for n=7: 424.2. found: 424.3. m/z calcd. for n=8: 462.3. found: 462.4. m/z calcd. for n=9: 500.3. found: 500.4. m/z calcd. for n=10: 538.3. found: 538.4. m/z calcd. for n=11: 576.3. found: 576.4. m/z calcd. for n=12: 614.3. found: 614.4.

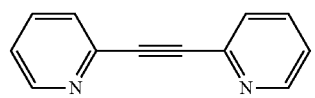 [SMILES: C(#Cc1ccccn1)c1ccccn1]

$^1$H NMR (CDCl$_3$, 500 MHz): δ 8.64 (2H, d, J=4.8 Hz), 7.72 (2H, t, J=7.6 Hz), 7.63 (2H, d, J=7.6 Hz), 7.28 (2H, t, J=6.4 Hz); $^{13}$C NMR (CDCl$_3$, 100 MHz): 150.4, 142.9, 136.5, 128.0, 123.6, 88.1. HR-MS (ESI): calcd. for C$_{12}$H$_8$N$_2$ [M+H$^+$]: 181.0760. Found: 181.0767.

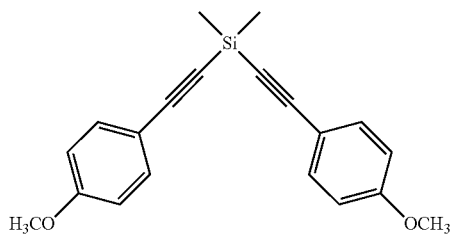 [SMILES: COc1ccc(C#C[Si](C)(C)C#Cc2ccc(OC)cc2)cc1]

$^1$H NMR (CDCl$_3$, 500 MHz): δ 7.45 (4H, d, J=11.5 Hz), 6.82 (4H, d, J=11.0 Hz), 3.80 (6H, s), 0.47 (6H, s); $^{13}$C-NMR (CDCl$_3$, 100 MHz): 160.2, 133.9, 115.0, 114.0, 106.2, 89.4, 55.5, 0.91. HR-MS (ESI): calcd. for C$_{20}$H$_{20}$O$_2$Si [M+Na$^+$]: 343.1124. Found: 343.1125.

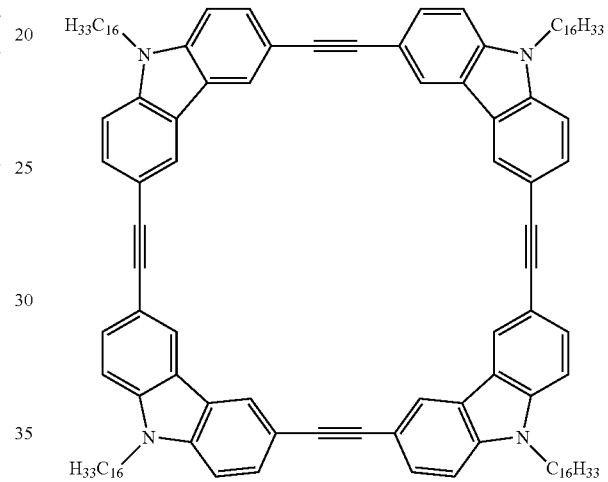

$^1$H NMR (CDCl$_3$, 500 MHz): δ 8.41 (6H, s), 7.72 (6H, d, J=10.5 Hz), 7.38 (6H, d, J=11 Hz), 4.30 (2H, t, J=8.0 Hz), 1.90 (6H, p, 8.5 Hz), 1.4-1.2 (104H, m), 0.91 (12H, m); $^{13}$C NMR (CDCl$_3$, 100 MHz): 140.4, 129.5, 124.2, 122.9, 114.7, 109.1, 89.3, 43.6, 32.2, 29.9, 29.8, 29.7, 29.3, 27.6, 23.0, 14.4. MALDI-TOF: [M+H$^+$] calcd. for C$_{120}$H$_{156}$N$_4$: 1654.24. Found: 1654.50.

Example 4

Compounds Prepared in Table 3

Synthesis of Substrates:

The substrates for entries 1-6 and 8 in Table 3 were prepared by standard Negishi and Sonogashira coupling actions following reported procedures (Bindl et al., 2009, J. Am. Chem. Soc. 131:9468; Zhang et al., 2004, J. Am. Chem. Soc. 126:12796; Zhang & Moore, 2005, J. Am. Chem. Soc. 127:11863; Thou & Larock, 2006, J. Org. Chem. 71:7422; Chang et al., 2004, J. Am. Chem. Soc. 126:12796; Zhao et al., 2006, J. Org. Chem. 71:7422). The substrate for entry 7 was prepared by the diesterification of adipic acid with 3-pentyn-1-ol, following reported procedure (Füstner et al., 1999, J. Am. Chem. Soc. 121:11108).

Substrate 8:

The diarylethynyl carbazole monomer (8) is prepared by following previously reported procedures (Jyothish & Zhang, 2011, Angew. Chem. Int. Ed. 123:3497).

Scheme 6:
Synthesis of the diaryoethynyl carbazole monomer (8).
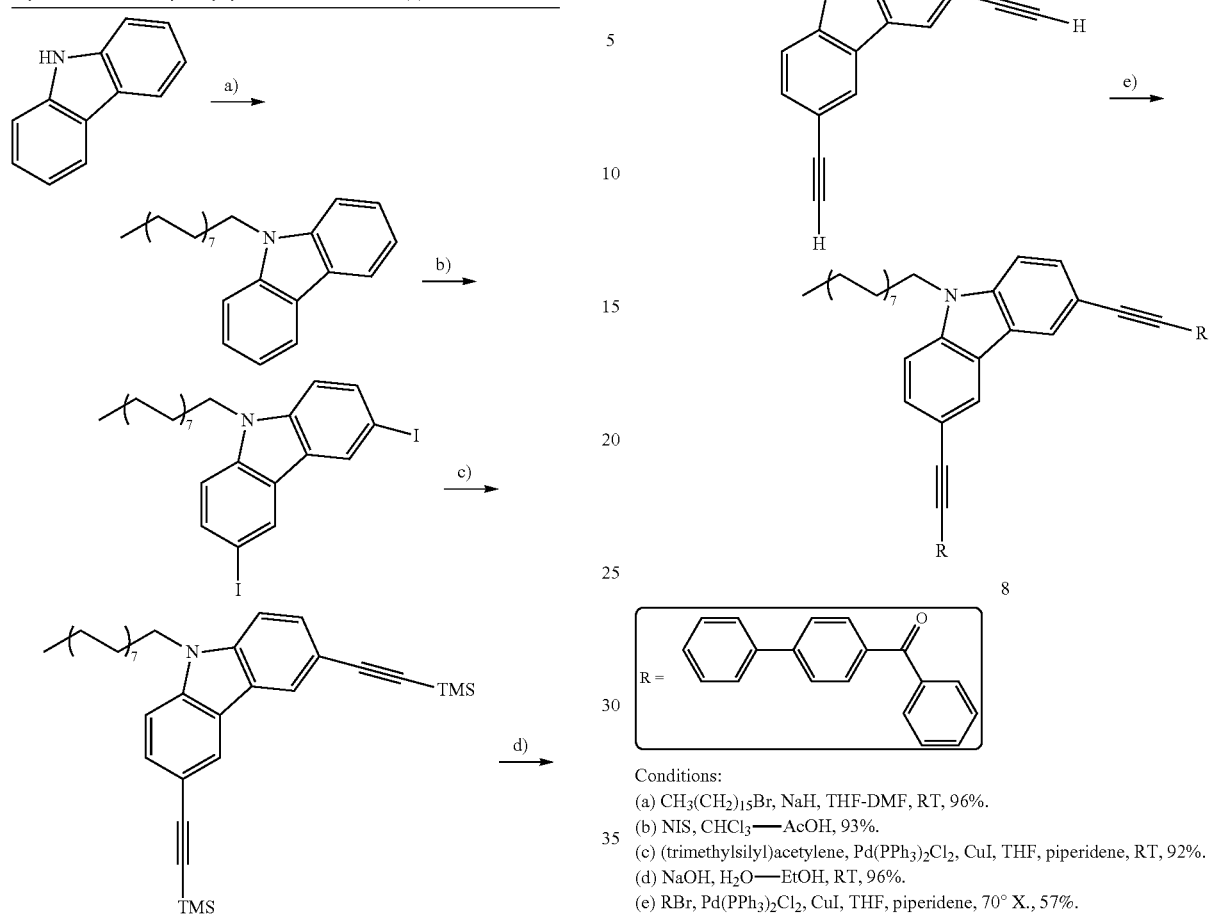
Conditions:
(a) CH$_3$(CH$_2$)$_{15}$Br, NaH, THF-DMF, RT, 96%.
(b) NIS, CHCl$_3$—AcOH, 93%.
(c) (trimethylsilyl)acetylene, Pd(PPh$_3$)$_2$Cl$_2$, CuI, THF, piperidene, RT, 92%.
(d) NaOH, H$_2$O—EtOH, RT, 96%.
(e) RBr, Pd(PPh$_3$)$_2$Cl$_2$, CuI, THF, piperidene, 70° X., 57%.
Scheme 7: Synthesis of the porphyrin monomers (5-7).
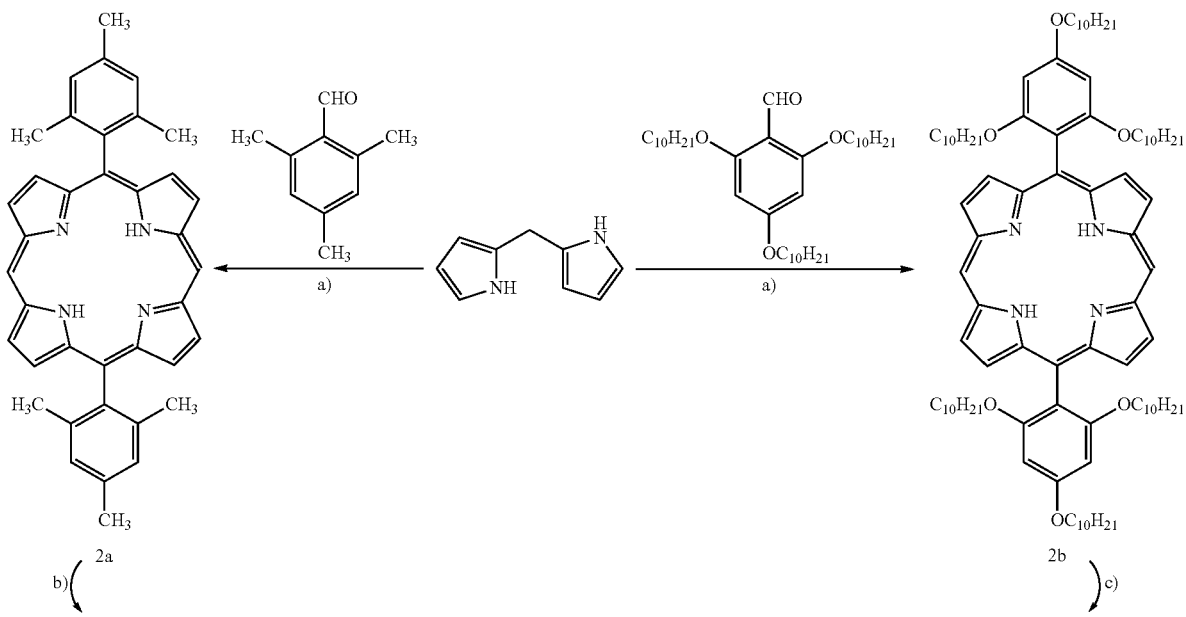

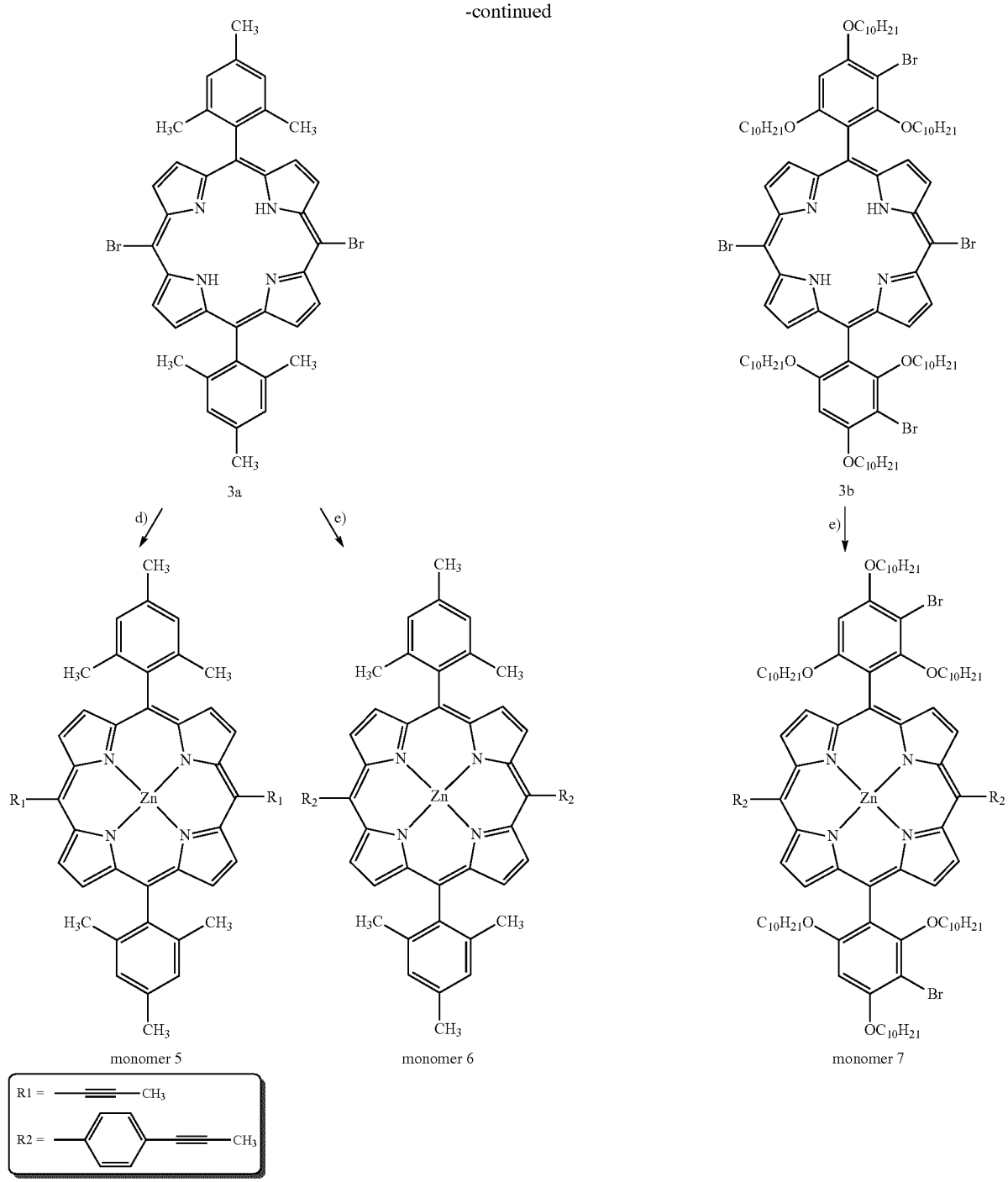

Conditions: (a) BF$_3$·Et$_2$O, DDQ, CHCl$_3$, RT, 34% (2a), 32% (2b). (b) NBS, CH$_2$Cl$_2$—CH$_3$OH (9:1), RT, 95%. (c) NBS, CHCl$_3$, RT, 85%. (d) propynyl lithium, ZnBr$_2$, Pd(PPh$_3$)$_4$, THF, RT, 85%. (e) n-BuLi, THF, ZnCl$_2$, 4-bromopropynylbenzene, Pd(PPh$_3$)$_4$, -78° C.-rt, 62% (monomer 6), 73% (monomer 7).

Synthesis of Dipyrromethane:

In a 250 mL flask supplied with a magnetic stirrer, a suspension of paraformaldehyde (375 mg, 12.5 mmol) and pyrrole (43 ml, 620 mmol) was introduced. The mixture was heated at 55° C. until complete dissolution. The heating was stopped, and trifluoroacetic acid was added drop by drop (0.10 ml. 1.3 mmol). The solution was stirred for one hour, upon which 10 mL 2 M NaOH(aq.) was added to neutralize it. The reaction mixture was again stirred for 45 min. After separation, the excess of pyrrole was distilled off under vacuum. Then, the mixture was purified with the use of column chromatography on silica gel. The product was separated by means of gradient elution (hexane/ethylacetate, 95/5, v/v) with a yield of 60% (1.09 g).

$^1$H NMR (500 MHz, CDCl$_3$) δ 7.91 (s, 2H), 6.68 (dd, J=4.2, 2.6 Hz, 2H), 6.15 (dd, J=5.8, 2.9 Hz, 2H), 6.06-6.02 (m, 2H), 4.00 (s, 2H). $^1$H NMR data was consistent with that reported in literature (Littler et al., 1999, Org. Chem. 64:1391).

2,4,6-Tris(decyloxy)benzaldehyde

A mixture of 2,4,6-trihydroxybenzaldehyde (3.00 g, 19.5 mmol), 1-bromodecane (25.87 g, 117.0 mmol), $K_2CO_3$ (8.07 g, 58.4 mmol), and KI (549 mg, 3.3 mmol) in DMF (150 mL) was stirred for 24 h at 110° C. and then one more portion of 1-bromodecane (5.0 g, 22.6 mmol) was added and continued stirring for another 24 h. The reaction mixture was cooled to 20° C. and extracted with $CH_2Cl_2$. The organic phase was washed with brine, dried ($Na_2SO_4$), and evaporated. Column chromatography (silica gel, hexane/$CH_2Cl_2$, 1:1, v/v) afforded the product (9.86 g, 88%) as yellow oil.

$^1$H NMR (400 MHz, $CDCl_3$) δ 10.38 (s, 1H), 6.02 (s, 2H), 3.98 (m, 6H), 1.98-1.66 (m, 6H), 1.44 (m, 6H), 1.40-1.12 (m, 36H), 0.87 (m, 9H). $^{13}$C NMR (101 MHz, $CDCl_3$) δ 187.9, 165.8, 163.7, 109.2, 91.5, 69.1, 68.4, 32.1, 29.8, 29.6, 29.6, 29.3, 29.2, 26.2, 22.9, 14.4; HR-MS (ESI): calcd. for $C_{37}H_{66}O_4$ [M+H$^+$]: 575.5034. Found: 575.5033.

Synthesis of [5,15-di-Mesityl]Por H2

A 500 mL flask with a magnetic stirrer was charged with dipyrromethane (700 mg, 4.79 mmol), mesitaldehyde (700 mg. 4.79 mmol), and 480 ml freshly distilled $CHCl_3$. The solution was bubbled with nitrogen for 10 min. $BF_3.Et_2O$ (0.19 ml, 1.52 mmol) was added drop by drop under vigorous stirring. The solution was stirred for one hour upon which DDQ (1.02 g, 4.5 mmol) was added in toluene, and the solution was stirred for one more hour. The reaction mixture was then passed through a sufficiently long silica gel column packed in hexane. This enabled the isolation of the desired porphyrin in reasonably high purity. To obtain an analytically pure sample, the product was further purified by column chromatography on silica gel. Porphyrin was separated by means of gradient elution ($CH_2Cl_2$/Hexanes, 2/3, v/v) with the yield of 34% (445 mg).

$^1$H NMR (400 MHz, $CDCl_3$) δ 10.23 (s, 2H), 9.34 (d, J=4.6 Hz, 4H), 8.90 (d, J=4.6 Hz, 4H), 7.34 (s, 2H), 2.67 (s, 6H), 1.86 (s, 12H). $^1$H NMR data was consistent with that reported in the literature (Vaz et al., 2001, Tetrahedron Lett. 42:7409).

Synthesis of [5,15-di-Mesityl-10,20-di-Br]P or H2

[5,15-di-Mesityl]P or H2 (720 mg, 1.32 mmol) from the previous step was dissolved in a mixture solvent system comprising of 120 ml $CH_2Cl_2$ and 13 mL methanol. Then NBS (587 mg, 3.29 mmol) was introduced in one solid portion and stirred for 5 min with regular monitoring of the reaction by TLC. Upon completion of the reaction, the solvent was distilled off at room temperature by rotary evaporation and the product was washed several times with methanol and dried. The yield was 95% (879 mg).

$^1$H NMR (400 MHz, $CDCl_3$) δ 9.55 (d, J=4.7 Hz, 4H), 8.69 (d, J=4.5 Hz, 4H), 7.29 (s, 4H), 2.64 (s, 6H), 1.82 (s, 12H), −2.55 (s, 2H). $^1$H NMR data was consistent with that reported in the literature (Vaz et al., 2001, Tetrahedron Lett. 42:7409).

Synthesis of the Porphyrin Monomer 5 (Scheme 7)

General procedure for the Negishi cross-coupling was followed for the preparation of the porphyrin monomer 9. To a solution of $ZnBr_2$ (164 mg, 0.73 mmol) and propynyl lithium (34.1 mg, 0.74 mmol) in THF (2 mL) was added the solution of [5,15-di-Mesityl-10,20-di-Br]P or H2 (130 mg, 0.185 mmol) in THF (3 mL), followed by addition of tetrakis(triphenylphosphine)palladium (0) (21 mg, 0.018 mmol). The solution was stirred for 12 h at room temperature. The reaction mixture was then poured into 2 N hydrochloric acid (70 mL) and the product was extracted with methylene chloride (3×100 mL). After drying ($Na_2SO_4$), the solvent was distilled off and the crude mixture was subjected to column chromatography over silica gel ($CH_2Cl_2$/hexanes, 1/3, v/v) to give pure product as a green solid (105 mg, 85%).

$^1$H NMR (500 MHz, $CDCl_3$) δ 9.62 (d, J=4.5 Hz, 4H), 8.74 (d, J=4.5 Hz, 4H), 2.66 (s, 6H), 2.65 (s, 6H), 1.83 (s, 12H). $^{13}$C NMR (101 MHz, $CDCl_3$) δ 147.0, 145.7, 139.7, 138.1, 137.9, 132.1, 130.3, 128.1, 117.5, 104.8, 22.0, 21.8; HR-MS (ESI): calcd. for $C_{44}H_{36}N_4Zn$ [M$^+$]: 684.2226. Found: 684.2228.

Synthesis of the Porphyrin Monomer 6 (Scheme 7)

An oven-dried Schlenk tube containing a magnetic stir bar was evacuated and backfilled with nitrogen three times. The Schlenk tube was charged with 4-bromopropynylbenzene (80.0 mmol, 0.41 mmol, 7.0 equiv) and dry THF (3 mL). The resulting solution was cooled to −78° C., then 1.6 M n-butyllithium in hexane (0.256 mL, 0.41 mmol) was added drop wise via syringe through the septum, and the resulting solution was stirred at −78° C. for 1 h. $ZnCl_2$ (68 mg, 0.5 mmol) was added in one solid portion by removal of the septum and continued the stirring. After 30 min at −78° C., the Schlenk tube was removed from the cooling bath and the resulting solution was stirred at room temperature for 1 h. The Schlenk tube is then taken into the glove box and added $Pd(PPh_3)_4$ (8.1 mg, 0.007 mmol) and [5,15-di-Mesityl-10,20-di-Br]P or H2 (100 mg, 0.058 mmol), with the aid of THF (3 mL). The solution was then stirred for 12 h at room temperature. The reaction mixture was poured into distilled water (100 mL) and the product was extracted with methylene chloride (3×100 mL). After drying ($Na_2SO_4$), the solvent was distilled off and the crude mixture was subjected to column chromatography over silica gel ($CH_2Cl_2$/hexanes, 1/3, v/v) to give pure product as a red solid (65 mg, 62%).

$^1$H NMR (400 MHz, $CDCl_3$) δ 8.90 (d, J=4.6 Hz, 4H), 8.80 (d, J=4.6 Hz, 4H), 8.21-8.15 (d, J=8.1 Hz, 4H), 7.79 (d, J=8.1 Hz, 4H), 7.29 (s, 4H), 2.64 (s, 6H), 2.23 (s, 6H), 1.84 (s, 12H). $^{13}$C NMR (101 MHz, $CDCl_3$) δ 150.2, 150.1, 142.4, 139.7, 139.20, 137.7, 134.6, 132.4, 131.1, 129.9, 127.9, 123.4, 119.9, 119.6, 87.2, 80.1, 21.9, 21.7, 4.8. HR-MS (ESI): calcd. for $C_{56}H_{44}N_4Zn$ [M$^+$]: 836.2853. Found: 836.2857.

Synthesis of 5,15-Di-[2,4,6-tris(decyloxy)phenyl]porphyrin

A 500 mL flask with a magnetic stirrer was charged with dipyrromethane (529.6 g, 3.62 mmol), 2,4,6-tris(decyloxy)benzaldehyde (2.08 g. 3.62 mmol), and 360 ml freshly distilled $CHCl_3$. The solution was bubbled with nitrogen for 10 min. $BF_3.Et_2O$ (0.148 ml. 1.17 mmol) was added drop by drop under vigorous stirring. The solution was stirred for one hour upon which DDQ (620 mg, 2.71 mmol) was added in toluene, and the solution was stirred for one more hour. The reaction mixture was then passed through a sufficiently long silica gel column packed in hexane. This enabled the isolation of the desired porphyrin in reasonably high purity. To obtain an analytically pure sample, this was further purified by column chromatography on silica gel. Porphyrin was separated by means of gradient elution ($CH_2Cl_2$/hexanes, 2/3, v/v). The yield was 32% (808.5 mg).

$^1$H NMR (500 MHz, Toluene-$d_8$) δ 9.90 (s, 2H), 9.24 (d, J=4.4 Hz, 4H), 9.11 (d, J=4.5 Hz, 4H), 6.80 (s, 4H), 4.26-4.08 (m, 4H), 3.73 (t, J=6.2 Hz, 8H), 1.96 (s, 4H), 1.66 (s, 4H), 1.56-0.68 (m, H), 0.59-0.46 (m, 8H), 0.42-0.24 (m, 6H), −2.54 (s, 2H). $^{13}$C NMR (101 MHz, $CDCl_3$) δ 161.5, 160.9, 148.4, 145.1, 130.9, 130.8, 113.0, 111.8, 104.1, 92.7, 68.9, 68.6, 32.3, 32.0, 31.9, 30.0, 30.0, 29.9, 29.7, 29.4, 29.4, 29.4, 29.0, 28.8, 26.6, 25.6, 23.1, 23.0, 22.9, 14.5, 14.44, 14.4. HR-MS (ESI): calcd. for $C_{92}H_{142}N_4O_6$ [M+H$^+$]: 1400.1002. Found: 1400.0950.

Bromination of 5,15-Di-[2,4,6-tris(decyloxy)phenyl]porphyrin 5,15-Di-[2,4,6-tris(decyl-oxy)phenyl]porphyrin (280 mg, 0.20 mmol) was dissolved in 20 ml CHCl$_3$ and cooled to −20° C. In order to neutralize the acid formed, pyridine (0.16 ml, 1.99 mmol) was added, and NBS (249 mg, 1.4 mmol, 7.0 equiv) was introduced in two solid portions and stirred for 15 min with regular monitoring of the reaction by TLC. Then, 7 ml of acetone was added and the solvent was distilled off at room temperature by rotary evaporation. The crude mixture was subjected to column chromatography over silica gel. Porphyrin was separated by means of gradient elution (CH$_2$Cl$_2$/Hexanes, 1/3, v/v). The yield was 85% (290 mg).

$^1$H NMR (500 MHz, Toluene-d$_8$) δ 9.55 (d, J=4.8 Hz, 1H), 8.93 (d, J=2.3 Hz, 4H), 8.92 (d, J=2.3 Hz, 4H), 6.67 (s, 1H), 6.66 (s, 1H), 4.08 (td, J=6.2, 2.8 Hz, 4H), 3.67 (mm 4H), 3.52 (t, J=6.2 Hz, 4H), 1.79-1.64 (m, 4H), 1.56-0.67 (m, 60H), 0.64-0.48 (m, 12), 0.48-0.14 (m, 16H), 0.14-0.01 (m, 2H), 0.01--0.15 (m, 2H), −0.26--0.42 (m, 4H), −0.42--0.70 (m, 8H), −2.24 (s, 1H), −2.29 (s, 1H). $^{13}$C NMR (101 MHz, CDCl$_3$) δ 159.5, 157.9, 157.9, 157.8, 118.9, 118.8, 113.1, 113.0, 103.1, 103.1, 99.4, 94.4, 73.4, 69.8, 69.1, 32.2, 31.9, 31.8, 31.8, 31.7, 29.8, 29.8, 29.6, 29.6, 29.5, 29.3, 29.3, 29.2, 29.2, 29.0, 28.9, 28.8, 28.7, 28.6, 28.5, 28.4, 28.3, 28.2, 26.4, 25.5, 24.6, 24.6, 22.9, 22.7, 22.7, 14.3, 14.3, 14.2. HR-MS (ESI): calcd. for $C_{92}H_{138}N_4O_6$ [M+H$^+$]: 1715.7406. Found: 1715.7346.

Synthesis of the Porphyrin Monomer 7 (Scheme 7)

An oven-dried Schlenk tube containing a magnetic stir bar was evacuated and backfilled with nitrogen three times. The Schlenk tube was charged with the 4-bromopropynylbenzene (450 mg, 2.32 mmol, 8.0 equiv) and dry THF (5 mL). The resulting solution was cooled to −78° C., then 1.6 M n-butyllithium in hexane (1.50 mL, 2.32 mmol, 8 equiv) was added dropwise via syringe through the septum, and the resulting solution was stirred at −78° C. for 1 h. ZnCl$_2$ (361 mg, 2.65 mmol) was added in one solid portion by removal of the septum and continued the stirring. After 30 min at −78° C., the Schlenk tube was removed from the cooling bath and the resulting solution stirred at room temperature for 1 h. The Schlenk tube was then taken into the glove box and added Pd(PPh$_3$)$_4$ (40 mg, 12 mol %) and 3b (500 mg, 0.29 mmol), with the aid of THF (3 mL). The solution was then stirred for 12 h at room temperature. The reaction mixture was then poured into distilled water (100 mL) and the product was extracted with methylene chloride (3×100 mL). After drying (Na$_2$SO$_4$), the solvent was distilled off and the crude mixture was subjected to column chromatography over silica gel (CH$_2$Cl$_2$/Hexanes, 1/3, v/v) to give pure product as a red solid (393.5 mg, 73%).

$^1$H NMR (500 MHz, toluene-d$_8$) δ 9.20 (d, J=4.6 Hz, 4H), 9.03 (d, J=4.6 Hz, 4H), 8.26-8.12 (m, 4H), 7.86 (t, J=7.6 Hz, 4H), 6.76 (s, 1H), 6.72 (s, 1H), 4.14-4.03 (m, 4H), 3.84 (t, J=6.2 Hz, 2H), 3.74 (t, J=6.2 Hz, 2H), 3.64 (t, J=6.3 Hz, 2H), 3.47 (t, J=6.0 Hz, 2H), 2.11 (m, 2H), 1.95 (m, 4H), 1.78-1.60 (m, 4H), 1.53-0.33 (m, 92H), 0.26-0.11 (m, 4H), −0.00--0.13 (m, 2H), −0.18 (m, 2H), −0.27 (m, 4H), −0.39--0.57 (m, 4H). $^{13}$C NMR (101 MHz, toluene-d$_8$) δ 159.8, 159.6, 158.9, 158.7, 157.9, 157.8, 151.4, 151.4, 150.1, 150.0, 142.9, 142.8, 134.7, 132.0, 132.0, 130.0, 123.9, 120.7, 120.5, 120.1, 120.0, 113.1, 113.0, 100.0, 94.4, 94.1, 86.7, 80.5, 73.6, 73.3, 69.4, 68.9, 68.8, 32.4, 32.1, 32.0, 32.0, 30.1, 30.1, 29.9, 29.9, 29.8, 29.7, 29.5, 29.5, 29.2, 29.2, 29.1, 29.0, 28.9, 28.7, 26.6, 25.9, 25.6, 25.1, 25.1, 23.1, 23.0, 22.9, 22.9, 14.4, 14.2, 14.2, 4.1, 1.3. HR-MS (ESI): calcd. for $C_{110}H_{150}N_4O_6Zn$ [M$^+$]: 1848.9205. Found: 1848.9164.

Synthesis of Porphyrin Polymer from 7

The triphenolammonium ligand L4 (5.9 mg, 0.0097 mmol) and the Mo(VI) triamide precursor (6.4 mg, 0.0097 mmol) were premixed in dry carbon tetrachloride 2.5 mL for 3 minutes to generate the catalyst in situ. The monomer 7 dissolved in 7 mL dry carbon tetrachloride was added to 100 mL Schlenck tube followed by transferring catalyst solution to the tube. The reaction mixture was stirred at 40° C. and monitored by GPC. During the reaction, the solution was exposed to vacuum 4 times, 1 min each time, to remove the 2-butyne byproduct. After 4 hours, the reaction showed no more change on GPC. The reaction was stopped by removal of solvent by rotavap and the residue was redissolved in diethyl ether and precipitated from MeOH to remove unreacted monomers and low molecular weight molecules. After centrifuge, the dark red solids (110 mg, 63%) were collected.

$^1$H NMR (500 MHz, C$_6$D$_6$) δ 9.42-9.25 (4H, m), 9.23-9.07 (4H, m), 8.42-7.86 (8H, m), 6.84-6.64 (2H, m), 4.09 (4, s), 3.88-3.55 (8H, m), 1.98 (4H, s), 1.72 (4H, s), 1.56-0.36 (90H, m), 0.21 (4H, s), 0.05-(−0.12) (m, 4H), −0.19 (4H, s), −0.36 (4H, s). $^{13}$C NMR (75 MHz, C$_6$D$_6$) δ 160.64, 160.46, 159.76, 159.67, 158.73, 152.27, 152.21, 150.77, 144.61, 135.78, 132.88, 130.96, 123.87, 121.59, 121.45, 120.72, 114.05, 113.93, 113.81, 100.91, 95.35, 95.11, 91.99, 74.57, 74.28, 70.24, 69.60, 33.01, 32.83, 32.79, 32.69, 32.63, 30.75, 30.72, 30.54, 30.48, 30.39, 30.35, 30.31, 30.20, 30.16, 29.91, 29.84, 29.78, 29.73, 29.60, 29.33, 27.34, 26.52, 26.31, 25.90, 25.83, 23.79, 23.70, 23.65, 23.62, 23.58, 15.04, 15.01, 14.95, 14.91.

Scheme 8: Syntheses of multidentate ligands (L7a-L7c) and their coordinated molybdenum (VI) propylidyne catalysts.

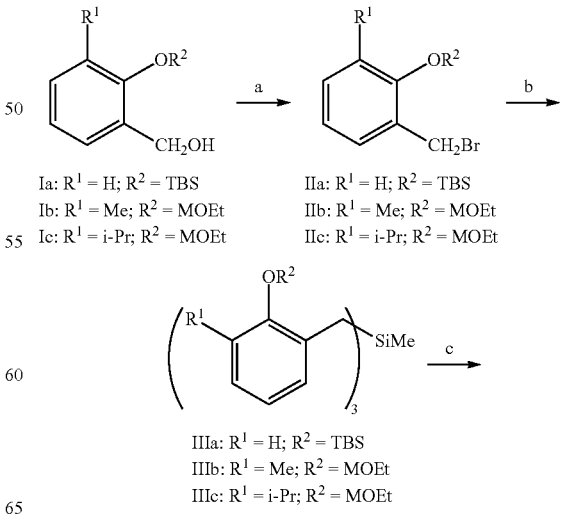

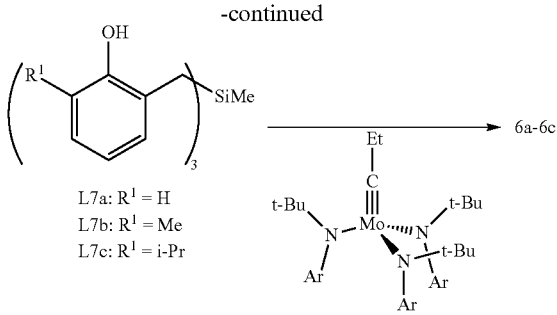

Conditions: a) PPh₃, Br₂, imidazole, CH₃CN, Et₂O (67%) for 1a; NBS, PPh₃, CH₂Cl₂ (77-86%) for 1b and 1c; b) Mg, THF, rt, then MeSiCl₃ (72-90%); c) Et₃N·HF, THF (39%) for L7a; PPTS, i-PrOH (63%-66%) for L7b and L7c.

Example 5

Synthesis and Metathesis Reactions of Novel Multidentate Triphenolsilane-Based

Synthesis of ligand L7a
(tris(2-hydroxybenzyl)methylsilane)

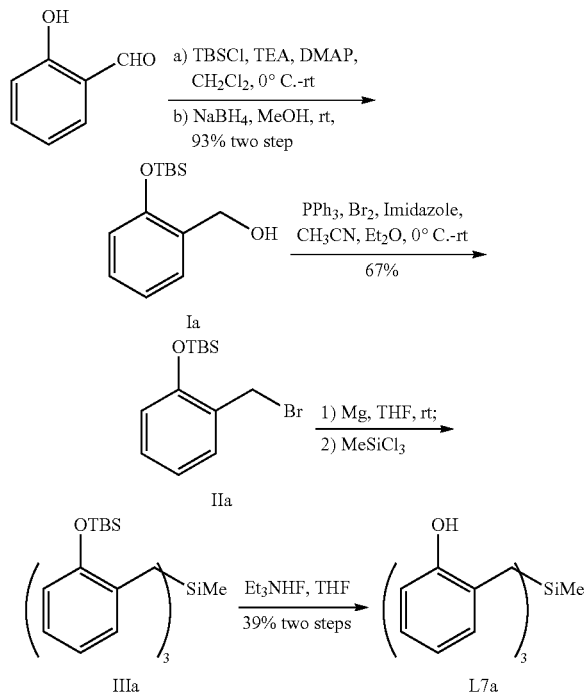

Scheme 9: Synthesis of ligand L7a

Preparation of (2-((tert-butyldimethylsilyl)oxy)phenyl)methanol (Ia)

To a stirred solution of salicylaldehyde (5.33 mL, 50 mmol), triethylamine (8.35 mL, 60 mmol), and 4-(dimethylamino)pyridine (100 mg, 0.8 mmol) in dichloromethane (200 mL) was added tert-butyldimethylsilyl chloride (9.04 g, 60 mmol) in portions at 0° C. The reaction mixture was then warmed to room temperature, and stirred for 26 h. The reaction was quenched by the addition of water (50 mL). The organic layer was washed with water (50 mL) and brine (50 mL), dried over anhydrous Na₂SO₄, and concentrated under reduced pressure. The crude product (12.9 g, 109%) was used for next step without further purification. The ¹H NMR data is consistent with the literature report (Kobayashi et al., 2008, Tetrahedron 64:9705-9716).

To a solution of the above obtained crude aldehyde (12.9 g) in methanol (100 mL) was added sodium borohydride (2.01 g, 53 mmol) in portions with stirring. After stirring at RT for 45 min, the solvent was removed under vacuum, and then water (100 mL) was added. The mixture was extracted with hexanes (3×100 mL). The combined organic extracts were dried over anhydrous Na₂SO₄ and concentrated under reduced pressure. Purification of the residue by flash column chromatography (hexane/ethyl acetate=5:1, v/v) yielded the compound Ia (11.13 g, 93%) as a colorless oil.

¹H NMR (500 MHz, CDCl₃) δ 7.31 (dd, J=7.5, 1.7 Hz, 1H), 7.19 (td, J=7.8, 1.8 Hz, 1H), 6.97 (td, J=7.4, 1.0 Hz, 1H), 6.83 (dd, J=8.1, 0.8 Hz, 1H), 4.69 (s, 2H), 1.03 (s, 9H), 0.27 (s, 6H). The ¹H NMR data is consistent with the literature report (Barrero et al., 2006, Tetrahedron 62:6012-6017).

Preparation of 2-((tert-butyldimethylsilyl)oxy)benzyl bromide (IIa)

To a solution of triphenylphosphine (39.5 g, 0.15 mol), (2-((tert-butyldimethylsilyl)-oxy)phenyl)methanol (Ia) (12.23 g, 0.05 mol) and imidazole (10.5 g, 0.15 mol) in acetonitrile and diethyl ether (500 ml, CH₃CN/Et₂O=1:3, v/v) was added bromine (7.7 mL, 0.15 mol) dropwise at 0° C. with stirring. The reaction mixture was stirred at 0° C. for 20 minutes, during which time a white solid precipitated. The solution was carefully decanted and washed with brine (100 mL). The remaining solid was washed with diethyl ether (2×160 mL). All of the organic solutions were combined and concentrated. Hexane (200 ml) was added to the residue, and the solid was removed by filtration. The hexane solution was concentrated to provide the crude product. The product was purified by vacuum distillation (66-68° C. 0.093 Torr) reduced distillation to provide compound IIa (10.4 g, 67%) as a colorless oil.

¹H NMR (400 MHz, CDCl₃) δ 7.33 (dd, J=7.6, 1.8 Hz, 1H), 7.18 (ddd, J=8.1, 7.5, 1.8 Hz, 1H), 6.92 (td, J=7.5, 1.1 Hz, 1H), 6.81 (dd, J=8.2, 1.1 Hz, 1H), 4.54 (s, 2H), 1.05 (s, 9H), 0.29 (s, 6H). The ¹H NMR data is consistent with the literature report (Stern & Swenton, 1989, J. Org. Chem. 54:2953-2958).

Preparation of tris(2-((tert-butyldimethylsilyl)oxy) benzyl)methylsilane (IIa)

A mixture of trichloromethylsilane (0.12 ml, 1.0 mmol) and Grignard reagent, which was prepared from 2-((tert-butyldimethylsilyl)oxy)benzyl bromide (IIa) (1.54 g, 5.0 mmol) and magnesium (1.2 g, 50 mmol) in tetrahydrofuran (12 mL), was stirred for 3 days. The reaction was quenched with satd. ammonium chloride (50 mL). The mixture was extracted with hexanes (3×50 mL). Purification by flash column chromatography (hexane/ethyl acetate=50:1, v/v) provided compound Ma (0.51 g, 72%) as a colorless oil.

¹H NMR (400 MHz, CDCl₃) δ 6.96-6.88 (m, 6H), 6.81-6.75 (m, 3H), 6.72 (dd, J=7.9, 1.2 Hz, 3H), 2.12 (s, 6H), 0.89 (s, 27H), 0.13 (s, 18H), -0.18 (s, 3H); ¹³C NMR (101 MHz, CDCl₃) δ 152.6, 130.5, 130.1, 124.8, 120.8, 118.6, 25.9, 18.2, 17.6, −4.1, −5.6. HR-MS (ESI): calcd. for $C_{40}H_{65}O_3Si_4Na^+$ [M+Na$^+$]: 729.3987. Found: 729.3975.

Preparation of tris(2-(hydroxy)benzyl)methylsilane (L7a)

Preparation of Desilylation Reagent Et$_3$N.HF

48% HF (1.0 mL) was diluted with water (1.0 mL), and the solution was neutralized with triethylamine to pH 7 to give the reagent.

A mixture of tris(2-((tert-butyldimethylsilyl)oxy)benzyl)methylsilane (Ma) (0.61 g, 0.86 mmol) and the above desilylation reagent (2.1 ml) in tetrahydrofuran (9 mL) was heated at 70° C. for 80 min. Then most of the solvent was removed, and CH$_2$Cl$_2$ (35 mL) was added. The resultant mixture was washed with water (8 mL), dried over anhydrous Na$_2$SO$_4$ and concentrated under reduced pressure. Purification of the residue by flash column chromatography (hexanes/ethyl acetate=4:1, v/v) provided the ligand L7a (143 mg, 39%) as a white solid.

$^1$H NMR (400 MHz, CDCl$_3$) δ 7.01 (ddd, J=7.8, 7.2, 1.8 Hz, 3H), 6.88 (dd, J=7.6, 1.8 Hz, 3H), 6.85-6.76 (m, 6H), 6.04 (s, 3H), 2.14 (s, 6H), −0.08 (s, 3H); $^{13}$C NMR (101 MHz, CDCl$_3$) δ 152.1, 130.5, 125.9, 125.7, 121.1, 115.4, 17.8, −4.0. HR-MS (ESI): calcd. for $C_{22}H_{24}O_3SiNa^+$ [M+Na$^+$]: 387.1392 Found: 387.1393.

Synthesis of ligand L7b
(tris(2-hydroxy-3-methylbenzyl)methylsilane)

Scheme 10: Synthesis of ligand L7b

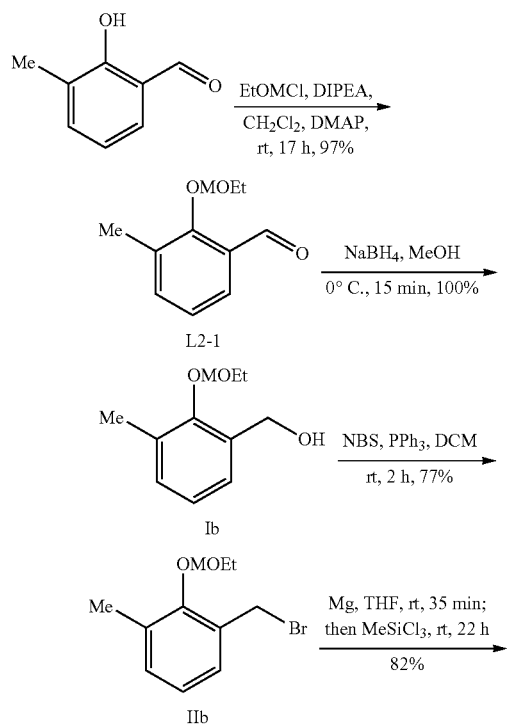

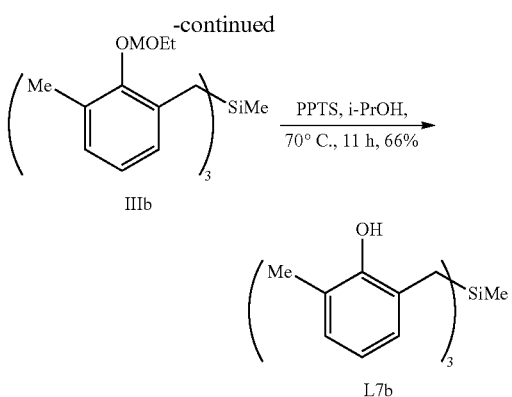

Preparation of
2-(ethoxymethoxy)-3-methylbenzaldehyde

To a stirred solution of 2-hydroxyl-3-methylbenzaldehyde (1.46 g, 10.7 mol), diisopropyl ethylamine (3.3 mL, 20.0 mmol) and 4-(dimethylamino)pyridine (122 mg, 1.0 mmol) in dichloromethane (35 mL) was added ethoxymethoxyl chloride (1.85 mL, 20.0 mmol) at RT. The mixture was stirred at RT for 17 h. The reaction was quenched with water (30 mL). The product was extracted with CH$_2$Cl$_2$ (3×40 mL). The combined organic extracts were washed with water (50 mL), and brine (50 mL), dried over anhydride Na$_2$SO$_4$. The residue was purified by flash column chromatography (hexanes/ethyl acetate=5:1, v/v) to provide the title compound (2.02 g, 97%) as a colorless oil.

$^1$H NMR (400 MHz, CDCl$_3$) δ 10.32 (d, J=0.8 Hz, 1H), 7.69 (ddd, J=7.8, 1.8, 0.7 Hz, 1H), 7.45 (ddt, J=7.5, 1.8, 0.8 Hz, 1H), 7.16 (td, J=7.7, 0.9 Hz, 1H), 5.12 (s, 2H), 3.83 (q, J=7.0 Hz, 2H), 2.35 (s, 3H), 1.26 (t, J=7.1 Hz, 3H); $^{13}$C NMR (101 MHz, CDCl$_3$) δ 190.8, 158.8, 137.3, 132.2, 129.7, 126.5, 124.5, 99.2, 66.1, 16.4, 15.1. HR-MS (ESI): calcd. for $C_{11}H_{13}O_3Na^+$ [M+Na$^+$]: 217.0841 Found: 217.0849.

Preparation of 2-(ethoxymethoxy)-3-methylbenzyl alcohol (Ib)

To a stirred solution of 2-(ethoxymethoxy)-3-methylbenzaldehyde (2.0 g, 10.3 mmol) in methanol (25 mL) was added sodium borohydride (0.42 g, 11.1 mmol) at 0° C. The mixture was stirred at 0° C. for 15 min. The solvent was then removed and the residue was purified by flash column chromatography (hexanes/ethyl acetate=4:1, v/v) to provide the title compound (2.02 g, 100%) as a colorless oil.

$^1$H NMR (400 MHz, CDCl$_3$) δ 7.20 (ddd, J=7.4, 1.6, 0.6 Hz, 1H), 7.15 (ddd, J=7.6, 1.9, 0.8 Hz, 1H), 7.04 (dd, J=7.5 Hz, 1H), 5.06 (s, 2H), 4.61 (s, 2H), 3.86 (q, J=7.1 Hz, 2H), 2.28 (s, 3H), 1.31 (t, J=7.1 Hz, 3H); $^{13}$C NMR (101 MHz, CDCl$_3$) δ 155.1, 134.5, 131.1, 130.8, 127.9, 124.7, 97.8, 65.8, 61.2, 16.8, 15.0. HR-MS (ESI): calcd. for $C_{11}H_{16}O_3Na^+$ [M+Na$^+$]: 219.0997 Found: 219.1005.

Preparation of 2-(ethoxymethoxy)-3-methylbenzyl bromide (IM)

To a stirred solution of 2-(ethoxymethoxy)-3-methylbenzyl alcohol (Ib) (2.67 g, 13.6 mmol) and triphenylphosphine (5.35 g, 20.4 mmol) in CH$_2$Cl$_2$ (70 mL) was added NBS (3.63 g, 20.4 mmol) at RT. The reaction was stirred at RT for 2 h, and quenched with water (15 mL). The product was extracted with CH$_2$Cl$_2$ (3×30 mL). The combined organic extracts were washed with water (30 mL), brine (30 mL), dried over Na$_2$SO$_4$, and concentrated under reduced pressure. Purification of the residue by flash column chromatography (hexane/ethyl acetate=10:1, v/v) yielded the compound IIb as a colorless oil (1.56 g, 77%).

$^1$H NMR (500 MHz, CDCl$_3$) δ 7.25 (dd, J=7.6, 1.3 Hz, 1H), 7.19-7.13 (m, 1H), 7.04 (t, J=7.6 Hz, 1H), 5.14 (s, 2H), 4.63 (s, 2H), 3.91 (q, J=7.1 Hz, 2H), 2.32 (s, 3H), 1.31 (t, J=7.1 Hz, 3H); $^{13}$C NMR (101 MHz, CDCl$_3$) δ 154.6, 132.0, 131.8, 131.4, 128.9, 124.6, 98.0, 65.7, 29.2, 16.9, 15.2.

Preparation of tris(2-(ethoxymethoxy)-3-methylbenzyl)(methyl)silane (IIIb)

To a stirred suspension of magnesium (2.13 g, 87.6 mmol) in tetrahydrofuran (16 mL) was added a solution of 2-(ethoxymethoxy)-3-methylbenzyl bromide (2.26 g, 8.76 mmol) in tetrahydrofuran (8 mL) at RT. The mixture was stirred at RT for 35 min. The supernatant solution was carefully transferred into another reaction flask, and methyltrichlorosilane (0.305 g, 2.04 mmol) was added. The resultant mixture was stirred at RT for 21 h. The reaction was quenched with satd. NH$_4$Cl (25 mL). The product was extracted with CH$_2$Cl$_2$ (3×25 mL). The combined organic extracts were washed with water (25 mL), brine (25 mL), dried over Na$_2$SO$_4$ and concentrated under reduced pressure. Purification of the residue by flash column chromatography (hexanes/ethyl acetate=10:1, v/v) provided the title compound (0.978 g, 82%) as a colorless oil.

$^1$H NMR (500 MHz, CDCl$_3$) δ 6.91 (ddd, J=7.5, 2.1, 0.9 Hz, 3H), 6.87 (t, J=7.3 Hz, 3H), 6.83-6.80 (m, 3H), 4.86 (s, 6H), 3.71 (q, J=7.0 Hz, 6H), 2.28 (s, 9H), 2.14 (s, 6H), 1.24 (t, J=7.1 Hz, 9H), −0.13 (s, 3H); $^{13}$C NMR (101 MHz, CDCl$_3$) δ 153.6, 133.1, 131.1, 127.8, 127.3, 123.9, 97.3, 65.3, 18.0, 17.1, 15.3, −4.8; HR-MS (ESI): calcd. for C$_{34}$H$_{48}$O$_6$SiNa$^+$ [M+Na$^+$]: 603.3118. Found: 603.3113.

Preparation of tris(2-hydroxy-3-methylbenzyl)methylsilane (L7b)

A solution of tris(2-(ethoxymethoxy)-3-methylbenzyl)(methyl)silane (Mb) (0.975 g, 1.68 mmol) and pyridinium p-toluenesulfonate (84 mg, 0.34 mmol) in isopropanol (16 mL) was heated at 70° C. for 11 h. Then the solvent was removed and the residue was purified by flash column chromatography (hexanes/ethyl acetate=5:1, v/v) to afford the compound L7b (0.448 g, 66%) as a colorless oil.

$^1$H NMR (400 MHz, CDCl$_3$) δ 6.90 (dd, J=6.6, 2.5 Hz, 3H), 6.82-6.64 (m, 6H), 5.29 (s, 3H), 2.25 (s, 9H), 2.11 (s, 6H), −0.07 (s, 3H); $^{13}$C NMR (101 MHz, CDCl$_3$) δ 150.7, 128.1, 127.2, 125.3, 123.2, 120.5, 17.9, 16.2, −3.7. HR-MS (ESI): calcd. for C$_{25}$H$_{30}$O$_3$SiNa$^+$ [M+Na$^+$]: 429.1862. Found: 429.1861.

Synthesis of ligand L7c
(tris(2-hydroxy-3-isopropylbenzyl)methylsilane)

Scheme 11: Synthesis of ligand L7c

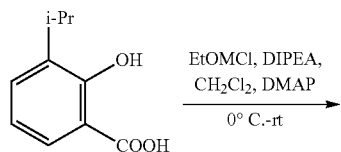

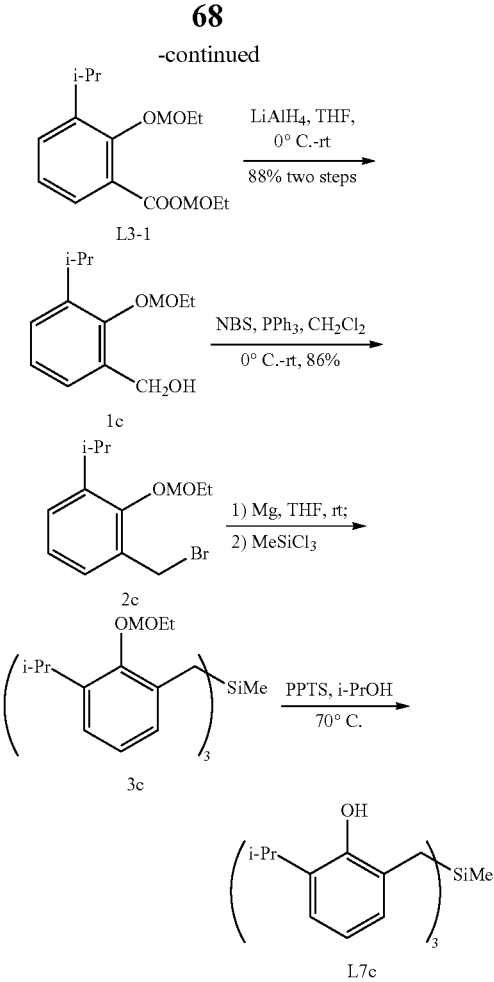

Preparation of ethoxymethyl 2-(ethoxymethoxy)-3-isopropylbenzoate (L3-1)

To a solution of 2-hydroxy-3-isopropylbenzoic acid (2.0 g, 11 mmol) and chloromethyl ethyl ether (3.1 mL, 3.3 g, 25.5 mmol) was added N,N-diisopropylethyl amine (5.5 mL, 4.3 g, 45.5 mmol) at RT. The reaction mixture was stirred at rt for 15 h, and at 35° C. for additional 12 h. The reaction was quenched with water (20 mL). The product was extracted with CH$_2$Cl$_2$ (3×20 mL). The combined organic extracts were washed with water (20 mL), and brine (20 mL), dried over Na$_2$SO$_4$, and concentrated under reduced pressure. The crude product was used for the next step without further purification.

The physical data for L3-1: $^1$H NMR (400 MHz, CDCl$_3$) δ 7.70 (ddd, J=7.7, 1.8, 0.5 Hz, 1H), 7.46 (dd, J=7.8, 1.8 Hz, 1H), 7.15 (td, J=7.7, 0.5 Hz, 1H), 5.50 (d, J=0.5 Hz, 2H), 5.10 (d, J=0.5 Hz, 2H), 3.87-3.73 (m, 4H), 3.54 (hept, J=6.9 Hz, 1H), 1.31-1.13 (m, 12H); $^{13}$C NMR (101 MHz, CDCl$_3$) δ 165.7, 155.2, 143.6, 131.0, 129.0, 124.0, 100.1, 89.6, 66.1, 65.6, 26.2, 23.5, 15.10, 15.07. HR-MS (ESI): calcd. for C$_{16}$H$_{24}$O$_5$SiNa$^+$ [M+Na$^+$]: 319.1521. Found: 319.1517.

Preparation of 2-(ethoxymethoxy)-3-isopropylbenzyl alcohol (Ic)

To a stirred suspension of LiAlH$_4$ (0.42 g, 11.1 mmol) in THF (10 mL) was added a solution of the above crude benzoate (L3-1) in THF (30 mL) dropwise at 0° C. The mixture was stirred at RT for 2 h. Water (2 mL) was added carefully to quench the reaction. The mixture was dried over anhydrous Na$_2$SO$_4$. The organic solution was decanted, and concentrated under reduced pressure. Purification of the residue by flash column chromatography (hexanes/ethyl acetate=5:1, v/v) provided the title compound (2.04 g, 88%) as a colorless oil.

$^1$H NMR (400 MHz, CDCl$_3$) δ 7.26-7.23 (m, 1H), 7.20 (dd, J=7.5, 1.9 Hz, 1H), 7.13 (t, J=7.5 Hz, 1H), 5.05 (s, 2H), 4.62 (s, 2H), 3.89 (q, J=7.1 Hz, 2H), 3.33 (s, 1H), 3.22 (p, J=6.9 Hz, 1H), 1.32 (t, J=7.1 Hz, 3H), 1.22 (d, J=6.9 Hz, 6H); $^{13}$C NMR (101 MHz, CDCl$_3$) δ 154.0, 141.7, 134.6, 127.9, 126.7, 125.2, 98.8, 65.8, 61.5, 26.8, 23.8, 14.9; HR-MS (ESI): calcd. for C$_{13}$H$_{20}$O$_3$Na$^+$ [M+Na$^+$]: 247.1310. Found: 247.1320.

Preparation of 2-(ethoxymethoxy)-3-isopropylbenzyl bromide (IIc)

To a stirred solution of 2-(ethoxymethoxy)-3-isopropylbenzyl alcohol (Ic) (2.04 g, 9.09 mmol) and PPh$_3$ (3.82 g, 14.6 mmol) in dichloromethane (45 mL) was added NBS (2.59 g, 14.6 mmol) in portions at 0° C. The reaction was stirred at 0° C. for 30 min. The reaction was quenched by the addition of water (50 mL). The product was extracted with CH$_2$Cl$_2$ (3×50 mL). The combined organic extracts were washed with water (50 mL), and brine (50 mL), dried over anhydrous Na$_2$SO$_4$, and concentrated under reduced pressure. Purification of the crude product by flash column chromatography (hexanes/ethyl acetate=10:1, v/v) provided the title compound (2.27 g, 86%) as a colorless oil.

$^1$H NMR (400 MHz, CDCl$_3$) δ 7.25-7.20 (m, 2H), 7.12-7.06 (m, 1H), 5.11 (s, 2H), 4.62 (s, 2H), 3.89 (q, J=7.1 Hz, 2H), 3.34 (hept, J=6.9 Hz, 1H), 1.30 (t, J=7.1 Hz, 3H), 1.20 (d, J=6.9 Hz, 6H). $^{13}$C NMR (101 MHz, CDCl$_3$) δ 153.2, 142.7, 131.3, 128.8, 127.5, 125.1, 98.8, 65.7, 29.4, 26.6, 23.8, 15.2. HR-MS (ESI): calcd. for C$_{13}$H$_{19}$O$_2$Na$^+$ [M+Na$^+$]: 309.0466 Found: 309.0477.

Preparation of tris(2-(ethoxymethoxy)-3-isopropylbenzyl)(methyl)silane (IIIc)

To a stirred suspension of Mg (0.61 g, 25 mmol) in THF (3.4 mL) was added a solution of 2-(ethoxymethoxy)-3-isopropylbenzyl bromide (5c) (0.58 g, 2.0 mmol) in THF (3.0 mL) dropwise at RT. The mixture was stirred at rt for 40 min. The supernatant solution was then transferred into another reaction flask, and methyltrichlorosilane (64 mg, 0.42 mmol) was added. The resultant mixture was stirred at rt for 40 h. The reaction was quenched with satd. NH$_4$Cl (25 mL). The product was extracted with CH$_2$Cl$_2$ (3×25 mL). The combined organic extracts were washed with water (25 mL), brine (25 mL), dried over Na$_2$SO$_4$ and concentrated under reduced pressure. Purification by flash column chromatography (hexanes/dichloromethane=1:4, v/v) afforded the title compound (0.255 g, 90%) as a yellow oil.

$^1$H NMR (500 MHz, CDCl$_3$) δ 7.01 (dd, J=7.7, 1.8 Hz, 3H), 6.96 (dd, J=7.6 Hz, 3H), 6.80 (dd, J=7.4, 1.8 Hz, 3H), 4.82 (s, 6H), (q, J=7.1 Hz, 6H), 3.36 (hept, J=6.8 Hz, 4H), 2.13 (s, 6H), 1.25 (t, J=7.1 Hz, 9H), 1.21 (d, J=7.0 Hz, 18H), −0.14 (s, 3H). $^{13}$C NMR (101 MHz, CDCl$_3$) δ 152.3, 142.1, 133.1, 127.5, 124.3, 122.5, 97.9, 65.3, 26.7, 23.7, 18.2, 15.2, −4.9. HR-MS (ESI): calcd. for C$_{40}$H$_{60}$O$_6$SiNa$^+$ [M+Na$^+$]: 687.4057 Found: 687.4056.

Preparation of tris(2-hydroxyl-3-isopropylbenzyl)(methyl)silane (L7c)

A solution of tris(2-(ethoxymethoxy)-3-isopropylbenzyl)(methyl)silane (IIIc) (1.01 g, 1.52 mmol) and pyridinium p-toluenesulfonate (0.24 g, 0.955 mmol) in isopropanol (17 mL) was heated at 70° C. for 11 h. The solvent was removed and the residue was purified by flash column chromatography (hexanes/ethyl acetate=5:1, v/v) to afford the title compound (0.47 g, 63%) as a colorless oil.

$^1$H NMR (400 MHz, CDCl$_3$) δ 7.02 (dd, J=7.6, 1.7 Hz, 3H), 6.83 (t, J=7.5 Hz, 3H), 6.76 (dd, J=7.5, 1.7 Hz, 3H), 5.38 (s, 3H), 3.29-3.09 (m, 3H), 2.13 (s, 6H), 1.30 (d, J=6.8 Hz, 18H), −0.05 (s, 3H); $^{13}$C NMR (101 MHz, CDCl$_3$) δ 149.6, 133.9, 127.6, 125.5, 122.4, 120.7, 27.2, 22.7, 18.0, −3.8. HR-MS (ESI): calcd. for C$_{31}$H$_{42}$O$_3$Na$^+$ [M+Na$^+$]: 513.2801. Found: 513.2802.

Synthesis of Metathesis Substrates:

The substrates for entries 1-5 and 7, Table 6 were obtained by standard Negishi and Sonogashira coupling reactions following reported procedures (Zhang et al., 2004, J. Am. Chem. Soc. 126:329-335; Bindl et al., 2009, J. Am. Chem. Soc. 131:9468). The substrate for entry 6, Table 1 was made by the diesterification of adipic acid with 3-pentyn-1-ol (Fürstner et al., 1999, J. Am. Chem. Soc. 121:11108-11113). The substrate for entry 5, Table 6 was prepared from carbazole (Zhao et al., 2006, J. Org. Chem. 71:7422-7432). The substrate for entry 9, Table 6 was prepared following reported procedure in Jyothish & Zhang, 2011, Angew. Chem., Int. Ed. 50:3435-3438).

Preparation of 9-octyl-3,6-di(prop-1-yn-1-yl)-9H-carbazole (substrate entry 5, Table 6)

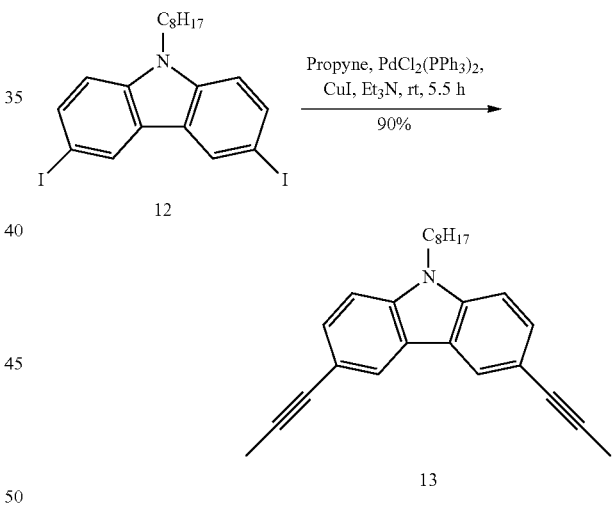

Propyne was bubbled through a degassed solution of diiodide 12 (0.328 g, 0.62 mmol), PdCl$_2$(PPh$_3$)$_4$ (0.049 g, 0.075 mmol), and CuI (0.012 g, 0.05 mmol) in a schlenk tube for 1 min at RT. Then the tube was sealed, and the reaction was stirred at RT for 5 h. The solvent was removed under reduced pressure, and the residue was dissolved in CH$_2$Cl$_2$ (50 mL). Water (15 mL) was added and the organic phase was separated. The aqueous phase was extracted with CH$_2$Cl$_2$ (50 mL). The combined organic layers were washed with water (20 mL), dried over Na$_2$SO$_4$, and concentrated under reduced pressure. Purification of the crude product by flash column chromatography (hexanes/DCM=10:1, then 5:1, v/v) afforded the title compound (196 mg, 90%).

$^1$H NMR (400 MHz, CDCl$_3$) δ 8.09 (d, J=1.3 Hz, 2H), 7.49 (dd, J=8.5, 1.6 Hz, 2H), 7.28 (d, J=8.5 Hz, 2H), 4.23 (t, J=7.3 Hz, 2H), 2.10 (s, 6H), 1.82 (d, J=7.3 Hz, 2H), 1.39-1.13 (m,

10H), 0.86 (t, J=7.0 Hz, 3H); $^{13}$C NMR (75 MHz, CDCl$_3$) δ 134.0, 129.5, 123.8, 122.4, 114.4, 108.7, 83.6, 80.5, 43.3, 31.8, 29.3, 29.1, 28.9, 27.3, 22.6, 14.1, 4.4. HR-MS (ESI): calcd. for $C_{26}H_{30}N^+$ [M+NH$^+$]: 356.2378. Found: 356.2375.

Preparation of 4,5-di((tert-butyldimethylsilyl)oxy)-1, 2-di(prop-1-yn-1-yl)benzene (substrate entry 6, Table 6)

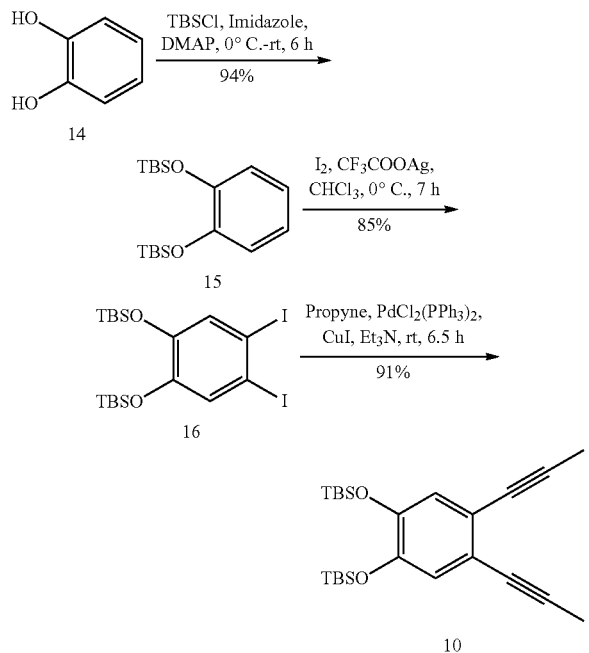

Compound 15:
To a solution of 1,2-dihydroxybenzene (1.08 g, 10 mmol), tert-butyldimethylsilyl chloride (4.59 g, 30 mmol) and 4-(dimethylamino)pyridine (126 mg, 1.0 mmol) in dimethylformamide (10 mL) was added imidazole (4.98 g, 40.6 mmol) in portions at 0° C. The reaction mixture was then warmed to RT and stirred at RT for 6 h. The reaction was quenched by the addition of water (50 mL). The product was extracted with hexanes/ethyl acetate (100 mL, 1:1, v/v). The organic extract was washed with water (2×50 mL), dried over Na$_2$SO$_4$, and concentrated under reduced pressure. The crude product was purified by passing through a short silica column with hexanes as the eluent to afford compound 15 (3.13 g, 94%) as a colorless oil.

$^1$H NMR (500 MHz, CDCl$_3$) δ 6.94-6.75 (m, 4H), 1.01 (s, 18H), 0.21 (s, 12H). The $^1$H NMR data is consistent with the literature report (Tanaka et al., 2001, Eur. J. Pharm. Sci. 13:77-83).

Compound 16:
To a stirred solution of the tert-butyldimethylsilyl ether (1.07 g, 2.95 mmol) in chloroform (25 ml) were added silver trifluoroacetate (1.44 g, 6.50 mmol) and iodine (1.66 g, 6.50 mmol) sequentially at 0° C. The reaction mixture was stirred at 0° C. for 7 h. The reaction was quenched with satd. Na$_2$S$_2$O$_3$ (30 mL). The solid was removed by filtration. The organic solution was dried over anhydrous Na$_2$SO$_4$ and concentrated under reduced pressure. Purification of the product by flash column chromatography (hexanes) provided diiodide 16 (1.48 g, 85%) as a colorless oil.

$^1$H NMR (500 MHz, CDCl$_3$) δ 7.28 (s, 2H), 0.97 (s, 18H), 0.19 (s, 12H). The $^1$H NMR data is consistent with the literature report (Kinder & Youngs, 1996, Organometallics 15:460-463).

Compound 10:
Propyne was bubbled through a degassed solution of diiodide 16 (1.29 g, 2.2 mmol), PdCl$_2$(PPh$_3$)$_4$ (0.23 g, 0.33 mmol), and CuI (0.045 g, 0.22 mmol) in a schlenk tube for 1 min at RT. Then the tube was sealed, and the reaction was stirred at RT for 6.5 h. The reaction mixture was diluted with hexanes (100 mL), washed with aq. NH$_4$Cl (2×15 mL), dried over Na$_2$SO$_4$ and concentrated under reduced pressure. Purification of the crude product by flash column chromatography (hexanes/DCM=10:1, then 5:1) provided compound 10 (0.832 g, 91%).

$^1$H NMR (500 MHz, CDCl$_3$) δ 6.82 (s, 2H), 2.10 (s, 6H), 0.97 (s, 18H), 0.20 (s, 12H); $^{13}$C NMR (75 MHz, CDCl$_3$) δ 146.7, 124.2, 119.6, 87.5, 78.4, 25.9, 18.4, 4.6, -4.1. HR-MS (ESI): calcd. for $C_{24}H_{38}NaO_2Si_2^+$ [M+Na$^+$]: 437.2308. Found: 437.2310.

General Procedure for Metathesis Experiments:
For the Vacuum-Driven Alkyne Metathesis Reactions (Method a):
The ligand (L7a-L7c) (0.003 mmol) and the precursor (2.0 mg, 0.003 mmol) were premixed in dry carbon tetrachloride (3 mL for all entries except entry 8, table 6, where the solvent volume was doubled to ensure ring closing alkyne metathesis) for 5 minutes to generate the catalyst in situ. Subsequently, the substrate (0.1 mmol) was added with internal standard and the stirring was continued for 3.5-5 h for entries 1-4 and 7-8 and 10-19 h for entries 5-6 with regular monitoring of the reaction by NMR. During the reaction, the solution was exposed to vacuum with 30 min interval to remove the metathesis byproduct 2-butyne and the loss of solvent during the application of vacuum was compensated by adding fresh solvent each time.

For 5 Å Molecular Sieves-Driven Closed-System Alkyne Metathesis Reactions (Method B):
The ligand (L7b-L7c) (0.003 mmol) and the precursor (2.0 mg, 0.003 mmol) were premixed in dry carbon tetrachloride for 5 minutes to generate the catalyst in situ. Subsequently, the substrate (0.1 mmol) was added with 5 Å molecular sieves (150 mg for entries 1-4 and 300 mg for entries 4-5) and internal standard. The stirring was continued for 5-7 h for entries 4 and 5 and 16-20 h for entries 1-3 and 6 in a closed system with regular monitoring of the reaction by NMR.

Yields were determined by $^1$H NMR with 1,4-dimethoxybenzene as an internal reference. For characterization of all known metathesis substrates and products, the analytical and spectroscopic data were compared with those of literature reported values.

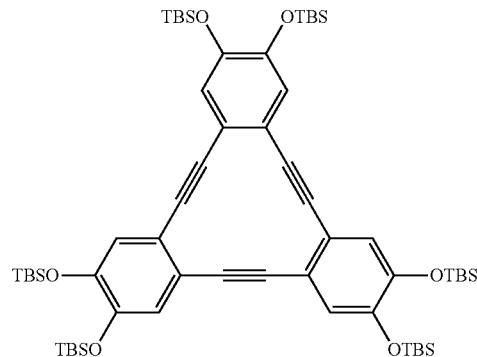 [SMILES: CC(C)(C)[Si](C)(C)Oc1cc2c(cc1O[Si](C)(C)C(C)(C)C)C#Cc1cc(O[Si](C)(C)C(C)(C)C)c(O[Si](C)(C)C(C)(C)C)cc1C#Cc1cc(O[Si](C)(C)C(C)(C)C)c(O[Si](C)(C)C(C)(C)C)cc1C#C2]

$^1$H NMR (500 MHz, CDCl$_3$) δ 6.73 (s, 6H), 0.99 (s, 54H), 0.22 (s, 36H); $^{13}$C NMR (101 MHz, CDCl$_3$) δ 147.5, 124.1, 120.3, 91.4, 25.9, 18.4, -4.0. HR-MS (ESI): calcd. for $C_{60}H_{96}NaO_6Si_6^+$ [M+Na$^+$]: 1103.5720. Found: 1103.5680.

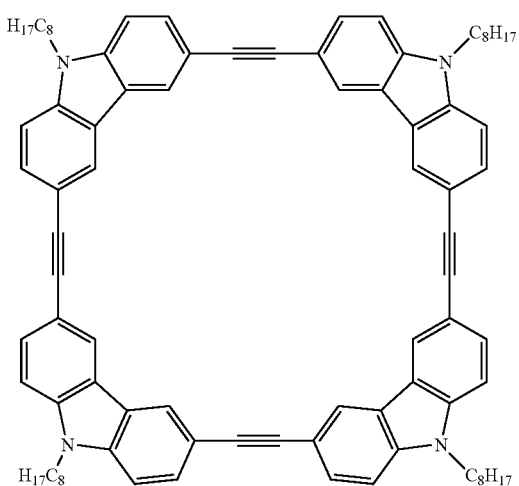

$^1$H NMR (400 MHz, CDCl$_3$) δ 8.44 (dd, J=1.6, 0.6 Hz, 8H), 7.72 (dd, J=8.5, 1.6 Hz, 8H), 7.40 (d, J=8.4 Hz, 8H), 4.32 (t, J=7.3 Hz, 8H), 1.97-1.84 (m, 8H), 1.47-1.14 (m, 40H), 0.92-0.81 (m, 12H). $^{13}$C NMR (101 MHz, Toluene-d8) δ 140.8, 129.8, 127.5, 123.6, 115.9, 109.2, 90.0, 45.6, 32.3, 29.7, 29.6, 29.3, 27.6, 23.0, 14.2. MALDI-TOF(m/z): calcd. for C$_{88}$H$_{93}$N$_4{}^+$ [M+H$^+$]: 1205.74. Found: 1205.72.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (III) or a salt thereof:

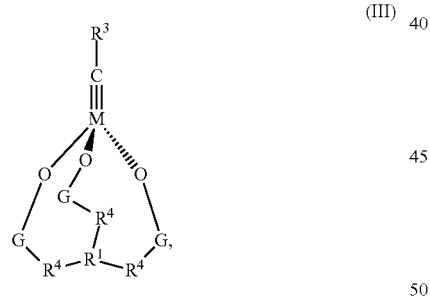

(III)

wherein:
each G is independently alkyl, aryl or heteroaryl, wherein the alkyl, aryl or heteroaryl is optionally and independently substituted with alkyl, halogen or electron-withdrawing substituents;
R$^1$ is selected from the group consisting of N$^+$R(A$^-$), B, CH, CR, SiR and a 1,3,5-trivalent phenyl moiety, wherein R is optionally substituted alkyl or aryl, and A$^-$ is an anion;
R$^3$ is selected from the group consisting of alkyl, alkyl(aryl) and aryl, all of which are optionally substituted;
R$^4$ is a single bond, heteroatom, or an optionally substituted C$_1$-C$_3$ alkyl chain; and,
M is a metal.

2. The compound of claim 1, wherein M is a transition metal.

3. The compound of claim 2, wherein M is selected from the group consisting of Mo, W, Re and Ta.

4. The compound of claim 1, wherein G is phenyl, naphthyl or anthracenyl.

5. The compound of claim 1, wherein the compound of formula (III) is the compound of formula (IV) or a salt thereof:

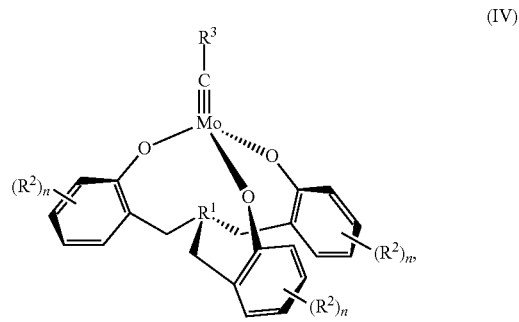

(IV)

wherein:
each occurrence of n is independently 0, 1, 2, 3, or 4;
R$^1$ is selected from the group consisting of N$^+$R(A$^-$), B, CH, CR, SiR and a 1,3,5-trivalent phenyl moiety, wherein R is optionally substituted alkyl or aryl, and A$^-$ is an anion;
each occurrence of R$^2$ is independently selected from the group consisting of alkyl, alkoxy, halogen, nitro, cyano, trifluoromethyl, trichloromethyl, carboxy, formyl, lower alkanoyl, carboxyamido and aryl lower alkanoyl;
R$^3$ is alkyl, alkyl(aryl) or aryl, all of which are optionally substituted; and
M is selected from the group consisting of Mo, W, Re and Ta.

6. The compound of claim 5, wherein R$^1$ is N$^+$(R)(A$^-$), R is optionally substituted alkyl or aryl, and A$^-$ is an anion.

7. The compound of claim 5, wherein the compound of formula (III) is selected from the group consisting of:

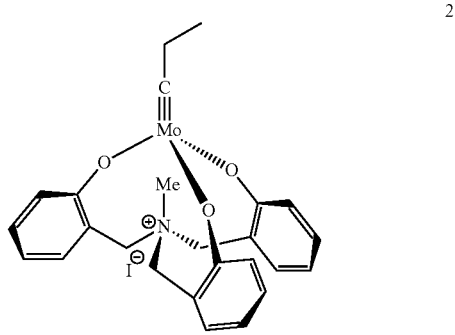

2

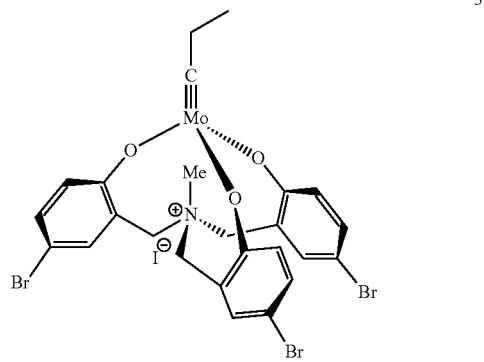

3

-continued

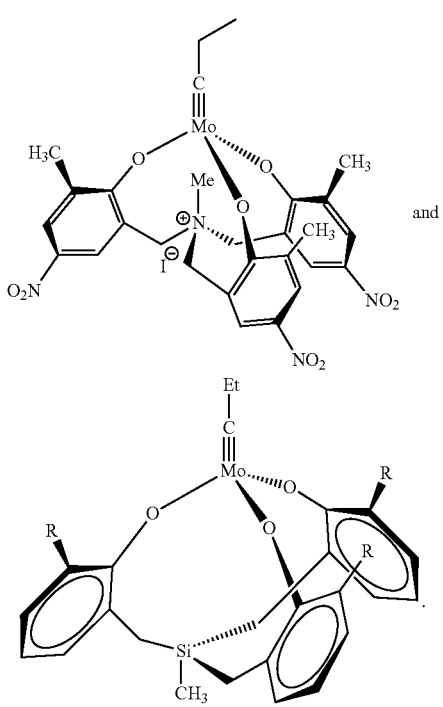

6a: R = H
6b: R = Me
6c: R = i-Pr

8. A method of preparing a compound of formula (IV), comprising reacting a compound of formula (II) with a metal alkylidyne compound with exchangeable ligands:

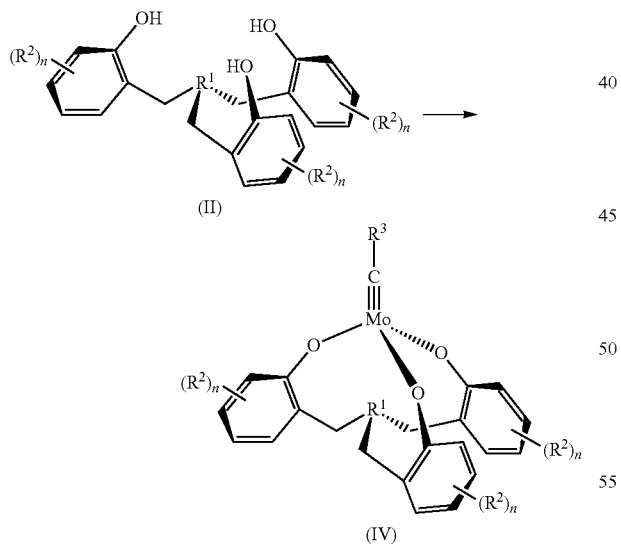

wherein:
R$^1$ is selected from the group consisting of N$^+$R(A$^-$), B, CH, CR, SiR and a 1,3,5-trivalent phenyl moiety, wherein R is optionally substituted alkyl or aryl, and A$^-$ is an anion;
each occurrence of n is independently 0, 1, 2, 3 or 4;
each occurrence of R$^2$ is independently alkyl, halogen or an electron-withdrawing group;
R$^3$ is alkyl, alkyl(aryl) or aryl, all of which are optionally substituted;
M is selected from the group consisting of Mo, W, Re and Ta.

9. A method of preparing an alkyne-containing metathesis product, comprising contacting a first alkyne-containing substrate with a second alkyne-containing substrate in the presence of a compound of formula (IV) or a salt thereof, whereby the metathesis product of the first and second alkyne-containing substrates is formed:

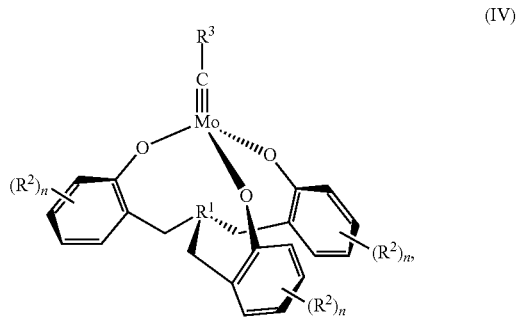

wherein:
each occurrence of n is independently 0, 1, 2, 3, or 4;
R$^1$ is selected from the group consisting of N$^+$R(A$^-$), B, CH, CR, SiR and a 1,3,5-trivalent phenyl moiety, wherein R is optionally substituted alkyl or aryl, and A$^-$ is an anion;
each occurrence of R$^2$ is independently selected from the group consisting of alkyl, halogen, nitro, cyano, trifluoromethyl, trichloromethyl, carboxy, formyl, lower alkanoyl, carboxyamido and aryl lower alkanoyl;
R$^3$ is alkyl, alkyl(aryl) or aryl, all of which are optionally substituted; and
M is selected from the group consisting of Mo, W, Re and Ta.

10. The method of claim 9, wherein the compound of formula (IV) is selected from the group consisting of:

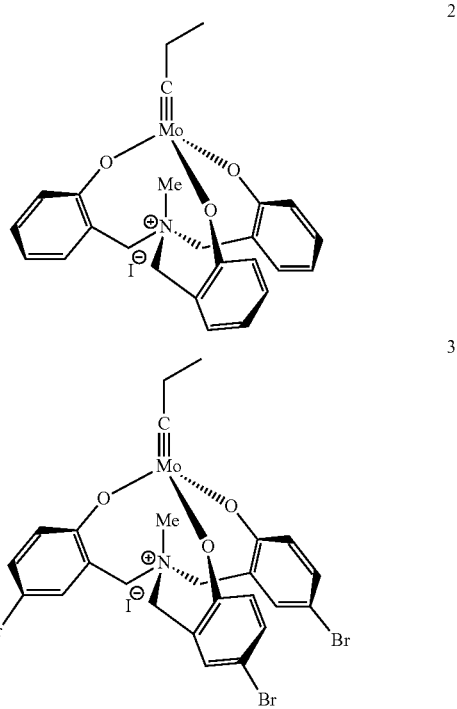

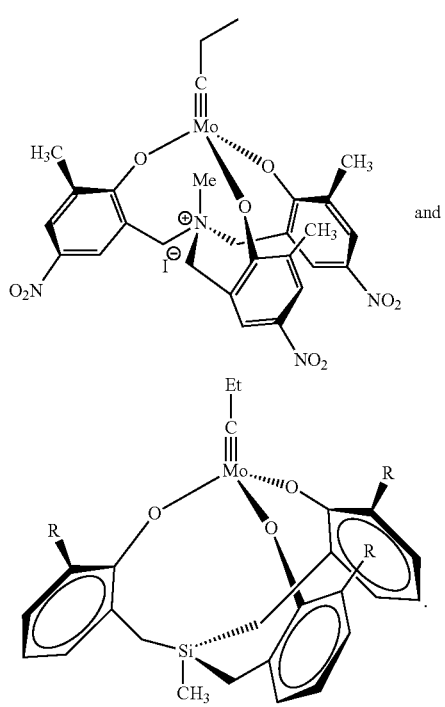
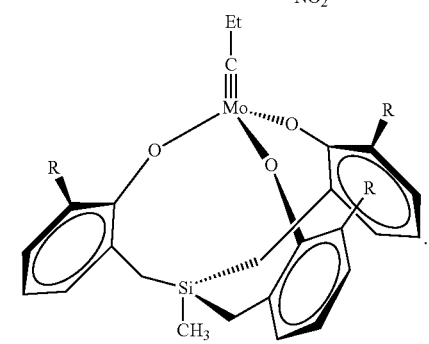
6a: R = H
6b: R = Me
6c: R = i-Pr
* * * * *